(12) United States Patent
Sherman et al.

(10) Patent No.: US 6,524,812 B1
(45) Date of Patent: *Feb. 25, 2003

(54) GENES ENCODING RESISTANCE TO DNA ALKYLATING AGENTS

(75) Inventors: David H. Sherman, St. Louis Park, MN (US); Paul R. August, Redmond, WA (US); Michael C. Flickinger, St. Paul, MN (US)

(73) Assignee: Regents of the University of Minnesota, Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/624,447

(22) PCT Filed: Oct. 6, 1994

(86) PCT No.: PCT/US94/11279

§ 371 (c)(1),
(2), (4) Date: Aug. 19, 1996

(87) PCT Pub. No.: WO95/09926

PCT Pub. Date: Apr. 13, 1995

Related U.S. Application Data

(63) Continuation-in-part of application No. 08/133,963, filed on Oct. 7, 1993, now abandoned.

(51) Int. Cl.$^7$ .................. C12P 21/06; C07H 21/02; C07H 21/04
(52) U.S. Cl. .................. 435/69.1; 435/91.4; 435/252.3; 435/320.1; 536/23.1; 536/23.7; 536/24.32
(58) Field of Search .............. 435/69.1, 91.4, 435/252.3, 320.1; 536/23.1, 23.7, 24.32

(56) References Cited

U.S. PATENT DOCUMENTS

| | | | |
|---|---|---|---|
| 3,214,440 A | 10/1965 | Cosulich et al. | |
| 3,219,530 A | 11/1965 | Bohonos et al. | |
| 3,272,696 A | 9/1966 | O'Connell | |
| 3,306,821 A | 2/1967 | Scroeder | |
| 3,332,944 A | 7/1967 | Cosulich et al. | |
| 4,395,558 A | 7/1983 | Kasai et al. | 548/422 |
| 4,843,002 A | 6/1989 | Rao et al. | 435/172.3 |
| 4,885,251 A | 12/1989 | Ingolia et al. | 435/183 |
| 4,886,757 A | 12/1989 | Richardson | 435/252.3 |
| 4,892,819 A | 1/1990 | Carr et al. | 435/69.1 |
| 4,935,340 A | 6/1990 | Baltz et al. | 435/6 |
| 4,975,278 A | 12/1990 | Senter et al. | 424/94.3 |
| 5,023,253 A | 6/1991 | Remers et al. | 514/228.2 |
| 5,032,512 A | 7/1991 | Witholt et al. | 435/123 |
| 5,108,918 A | 4/1992 | Groenen et al. | 435/172.3 |
| 5,140,013 A | 8/1992 | Gaudreault et al. | 514/21 |
| 5,252,673 A | 10/1993 | Hirano et al. | 525/183 |
| 5,256,685 A | 10/1993 | Arai et al. | 514/410 |
| 5,334,611 A | 8/1994 | Arai et al. | 514/410 |
| 5,352,798 A | 10/1994 | Benigni et al. | 548/422 |
| 5,374,739 A | 12/1994 | Kaneko et al. | 548/422 |
| 5,462,862 A | 10/1995 | Groenen et al. | 435/69.1 |
| 5,514,544 A | 5/1996 | Rao et al. | 435/6 |
| 5,545,553 A | 8/1996 | Gotschlich | 435/252.33 |
| 5,554,638 A | 9/1996 | Dewhirst et al. | 514/398 |
| 5,589,385 A | 12/1996 | Ryan et al. | 435/258.35 |
| 5,629,427 A | 5/1997 | Peterson | 546/276.7 |
| 5,665,564 A | 9/1997 | Caruso et al. | 435/69.1 |
| 5,672,497 A | 9/1997 | Cox et al. | 435/320.1 |
| 5,747,469 A | 5/1998 | Roth et al. | 514/44 |
| 5,788,958 A | 8/1998 | Dewhirst et al. | 424/78.38 |
| 5,824,513 A | 10/1998 | Katz et al. | 435/76 |
| 5,866,410 A | 2/1999 | Ryan et al. | 435/320.1 |

FOREIGN PATENT DOCUMENTS

| | | |
|---|---|---|
| EP | 0 238 323 | 9/1987 |
| EP | 0 468 217 | 1/1992 |
| EP | 0 468 220 | 1/1992 |
| FR | 2 696 189 | 4/1994 |
| JP | 61205484 | 9/1986 |
| JP | 63313589 | 12/1988 |
| JP | 9268190 | 10/1997 |
| WO | 96/01901 | 1/1996 |
| WO | 96/10084 | 4/1996 |

OTHER PUBLICATIONS

Aquino, Univ. California, Los Angeles, Calif. 1976, pp182, pp Diss. Abstr. Int.B, 37(4), 1545, 1976.*

August et al. (1992) Abstract B19 from Fifth ASM conference on Genetics and Molecular Biology of Industrial Microorganisms, Bloomington, In, 1992.*

August et al. (Aug., 1993) Draft of Abstract for submission to Combined Canadian Society for Microbiology and Society for Industrial Microorganism Meeting, 1993.*

August et al. (1993) 205th ACS National Meeting Abstract, 1993.*

August, et al. "Cloning and Expression of the *Streptomyces lavendulae* Mitomycin C Resistance Genes in *Streptomyces lividans*", Abstract 0–12 at p. 31, General Meeting of the Microbiology Society, Abstract, (May 20–26, 1992).

Beijnen, et al., "Mitomycin Antitumour Agents: A Review of Their Physico–Chemical and Analytical Properties and Stability", *J. Pharm. Biochem. Anal.*, 4:275–295 (1986).

Brandsch, et al. "6–Hydroxy–D–nicotine Oxidase of *Arthrobacter oxidans*: Gene Structure of the Flavoenzyme and its Relationship to 6–hydroxy–L–nicotine Oxidase", *Eur. J. Biochem.*, 167:315–320 (1987).

(List continued on next page.)

Primary Examiner—Christopher S. F. Low
Assistant Examiner—Rita Mitra
(74) Attorney, Agent, or Firm—Schwegman, Lundberg, Woessner & Kluth, P.A.

(57) ABSTRACT

The invention provides genes encoding resistance to DNA bioreductive alkylating or cleaving agents and methods of identifying and using those genes.

24 Claims, 20 Drawing Sheets

OTHER PUBLICATIONS

Cera, et al. "Modulation of Mitomycin Cross–Linking by DNA Bending in the *Escherichia coli* CAP Protein–DNA Complex", *Biochemistry*, 28:3908–3911 (1989).

Claridge, et al. "New Mitomycin Analogs Produced by Directed Biosynthesis", *J. Antibiotics*, 39:436–446 (1986).

Davies "A New Look at Antibiotic Resistance", *FEMS Microbiology Reviews*, 39:363–371 (1986).

Herr, et al. "Porfiromycin, A New Antibiotic: II. Isolation and Characterization", *Antimicrobial Agents Annual*, Plenum Press, NY at pp 23–26 (1990).

Hoey, et al. "Reductive Activation of Mitomycin C", *Biochemistry*, 27:2608–2614 (1988).

Hopwood, et al. "Genetic Manipulation of Streptomyces" (1985), pp 77–78, 292–293, 214–224.

Iyer, et al. "Mitomycins and Porfiromycin: Chemical Mechanism of Activation and Cross–Linking of DNA", *Science*, 145:55–58 (1964).

Kasai, et al. "Studies on the Chemistry of Mitomycins", *SynLett*, 10:778–790 (1992).

Kiyoto, et al. "A New Antitumor Antibiotic, FR–900482: II. Production, Isolation, Characterization and Biological Activity", *J. Antibiotics*, 40:594–599 (1987).

Kumar, et al. "Orientation Isomers of the Mitomycin C Interstrand Cross–Link in Non–Self–Complementary DNA. Differential Effect of the Two Isomers on Restriction Endonuclease Cleavage at a Nearby Site", *Biochemistry*, 32:1364–1372 (1993).

Masuda, et al. Interstrand DNA–DNA and DNA–Protein Cross–Links by a New Antitumor Antibiotic, FK973, in L1210 Cells:, *Cancer Research*, 48:5172–5177 (1988).

Mohler, et al *Eur. J. Biochem.*, 29:152–155(1972).

Moscow, et al. *Multidrug Resistance. Cancer Chemotherapy and Biological Response Modifiers Annual 11*. Elsevier Science Publishers B.V., 97–114 (1990).

Nicolaou, et al. "Chemistry and Biology of the Enediyne Anticancer Antibiotics", *Angewandte Chemie Int. Ed. Engl.*, 30:1387–1416 (1991).

Nielsen, et al. "Regulated Overproduction and Secretion of Yeast Carboxypeptidase Y", *Appl. Microbiol. Biotech.*, 33:307–312 (1990).

Pan, et al. *Cancer Chemother. Pharmacol*, 31:23–31 (1992).

Schwartz, et al. "Mitomycin C: Chemical and Biological Studies on Alkylation", *Science*, 142:1181–1183 (1963).

Teng, et al., "DNA Sequence Specificity on Mitomycin Cross–Linking", *Biochemistry*, 28:3901–3907 (1989).

Tomasz, et al. "Isolation and Structure of a Covalent Cross–Link Adduct Between Mitomycin C and DNA", *Science*, 235:1204–1208 (1987).

Uchida, et al. "Structure of FR 900482, a Novel Antitumor Antibiotic from a Streptomyces", *J. Am. Chem. Soc.*, 109:4108–4109 (1987).

Witt, et al. Unification of the Genera Streptoverticillum and Streptomyces, and Amendation of *Streptomyces waksman* and Henrici 1943, $339^{AL}$, *System. Appl. Microbiol.*, 13:361–371 (1990).

Woo, et al. "DNA Interstrand Cross–Linking by Reductively Activated FR900482 and FR66979", *J. Am. Chem. Soc.*, 115:1199–1200 (1993).

August, et al., "Cloning and Expression of the *Streptomyces lavendulae* Mitomycin C Resistance Genes in *Streptomyces lividans*", *92nd General Meeting of the American Society for Microbiology*, New Orleans, Louisiana, Abstract No. B19, 16 (1992).

August, P.R., et al., "Cloning and Analysis of a Locus (mcr) Involved in Mitomycin C Resistance in *Streptomyces lavendulae*", *Journal of Bacteriology*, 176(14), 4448–4454 (1994).

Becker, A.M., et al., "3–Amino–5–Hydroxybenzoic Acid in Antibiotic Biosynthesis VI.* Directed Biosynthesis Studies with Ansamycin Antibiotics", *The Journal of Antibiotics*, 36(10), 1323–1328 (1983).

Bevitt, D.J., et al., "6–Deoxyerythronolide–B synthase 2 from *Saccharopolyspora erythraea*: cloning of the structural gene, sequence analysis and inferred domain structure of the multifunctional enzyme", *European Journal of Biochemistry*, 204, 39–49 (1992).

Byrom, D., "Polymer synthesis by micro–organisms: technology and economics", *Tibtech*, 5, 246–250 (1987).

Donadio, S., et al., "An erythromycin analog produced by reprogramming of polyketide synthesis", *Proceedings of the National Academy of Sciences*, 90, 7119–7123 (1993).

Donadio, S., et al., "Modular Organization of Genes Required for Complex Polyketide Biosynthesis", *Science*, 252, 675–679 (1991).

Donadio, S., et al., "Organization of the enzymatic domains in the multifunctional polyketide synthase involved in erythromycin formation in *Saccharopolyspora erythraea*", *Gene*, 111(1), 51–60 (1992).

Han, L., et al., "Cloning and Characterization of Polyketide Synthase Genes for Jadomycin B Biosynthesis in *Streptomyces venezuelae* ISP5230", *Microbiology*, 140, 3379–3389 (1994).

Kao, C.M., et al., "Engineered Biosynthesis of a Complete Macrolactone in a Heterologous Host", *Science*, 265, 509–512 (1994).

Shen, B., et al., "Tetracenomycin F2 Cyclase and Tetracenomycin F1 Monooxygenase: Key Enzymes in the Early Steps of the Biosynthesis of Tetracenomycin C", *Fifth ASM Conference on Genetics and Molecular Biology of Industrial Microorganisms*, Bloomington, IN, Abstract No. A4, 9 (Oct. 12, 1992).

Stassi, D., et al., "Identification of a *Saccharopolyspora erythraea* Gene Required for the Final Hydroxylation Step in Erythromycin Biosynthesis", *Journal of Bacteriology*, 175, 182–189 (1993).

Bierman et al., "Plasmid Cloning Vectors for the Conjugal Transfer of DNA from *Escherichia coli* to Streptomyces spp.", *Gene*, 116, 43–49 (1992).

* cited by examiner

```
CGTCGTCATG GAGAGAAGGA GTCCGGGTGA CCTCATCCGA CGGATCGGAC CTCACCACTC   1560
           MCRA2 ⟶  V  T    S  S  D    G  S  D    L  T  T  L
TGGTCAACGT GGGCCGGTCC GTGGCGAGGT ACTTCGAGCG CATCGGCATC ACCGAGATCG   1620
 V  N  V    G  R  S    V  A  R  Y   F  E  R   I  G  I   T  E  I  A
CGCAACTGCG GGACCGCGAT CCGGTCGAGT TGTACGAGCG GATGTCAGCC GCCTTCGGGC   1680
 Q  L  R    D  R  D    P  V  E  L   Y  E  R   M  S  A    A  F  G  Q
AGCGCCTCGA TCCCTGCCTG CTCGACACCG TCATGTCGGC GGTGGACCAG GCCGAAGGCC   1740
 R  L  D    P  C  L    L  D  T  V   M  S  A   V  D  Q   A  E  G  L
TGCCCGCTCG CCCCTGGTGG CACTACACCC CGGAGCGCAA GCGGTTGCTG GCAGGCGAAG   1800
 P  A  R    P  W  W    H  Y  T  P   E  R  K   R  L  L    A  G  E  G
GCCATGACCG GGCCGGTGGA ACCGCGGGGG AGGGGACAGC GTAGAGACAC AGCCGTGAGT   1860
 H  D  R    A  G  G    T  A  G  E   G  T  A  .
GAAGGGGAAA CGGCAGGAGA GGGCCGGCCC GGCACGGAGT GGCCCGTCAG CAATGGCCGG   1920
ACGGGTTCAC ACCGCCGGTG TACGCGAGCG GCCGGGTCAC CTCTCCACCA GTTCGCTCAG   1980
TGCCCAAGTG TGGCGGCCAC ATGCGCTCGC CGGCCCAGTG GAGAGGTGGT CAAGCGAGTC
                                     .         R  E  V   L  E  S  L
GCTTGAGGGG CGGTAGAGGG CATGTAGTGC GCGGTCTACT CGGACCAGGC GCTTCGGGCG   2040
 S  S  G    A  M  E    R  V  D    A  L  H    A  Q  D    A  F  G  A
GTCGCAGCGG CAGAGGCGCT TCCCCTGTGG CCGCGCCCGG TCCGCGTCCC GCGCGACGTA   2100
 L  T  A    T  E  A    F  P  V  G   A  R  A   L  R  L   A  R  Q  M
CGCGTCCTGT GCCCGGTCCC AGAACCCAGG CATCGGCTTC CGCCGGTCCC TTGCCGCCAC   2160
 R  L  V    R  A  L    T  K  P  G   Y  G  F   A  A  L    S  R  R  H
CTCGACGGCG CGCGGCTCTG GGTGGCTCAG CCGCCAGCGA CACTGCCTCG CTGGCCGAAG   2220
 L  Q  R    A  G  L    G  V  S  D   A  T  A    T  V  S    R  G  A  E
CTCCCTGTGG TGCTGACGAG CGTCCTCGCC CAGCTGCCCA AGGCGCAGCC GGCGCTGCGG   2280
 L  S  V    V  V  A    R  L  L  P   D  V  P    E  A  D    A  A  V  G
CGTTACGGTC TAGGAGCTCC CGCCGCCGGC CCAGGCCGGC GGCGGCAGCT GCGCAAGCCA   2340
 C  H  W    I  R  S    P  P  P  R   T  G  G    G  D  V   R  E  T
CTCTGCCGCG CAGGGCCGCG GCCCGGTCTC CAGCCGCTCT AGCTGAGCGA CCAGGGCGTC   2400
 L  R  R    T  G  A    G  P  W  L   D  A  L    D  V  R    Q  D  R  L
GAGTACGCGC CCCTACGGCT CGTCCCGCCC CCGCTACGGC CCCCTCTTCG CCTGTGGGTG   2460
 E  H  A    P  I  G    L  L  A  P   A  I  G   P  S  F   R  V  G  V
GGTCTTCGGG GCCACTCACG ACATCCGCGA ACATAGCCCG GGCCTCTGCT CCTCGGCCGG   2520
 W  F  G    R  H  T    S  Y  A  S   T  D  P    G  S  V    L  L  R  G
ACGGCAGGTG TCGTCCAGCT ACGTCGGCAG TCCATTGTGC CAGCAGCAGA GCGGCGGTGG   2580
 A  T  W    L  L  D    I  C  G  D   P  L  V   T  T   E  G  G
CCATGTGGGC CCGCGAGGGA CGTGGGTCGG CTAGCGCGGG CCGTCGGCCC TGCACGCGAG   2640
 T  C  G    P  A  G    Q  V  W  G   I  A  G   P  L  R    S  T  R  E
AAGCATGAGC CCCCTGTGCG ACACTTAAAA TGCGGAGCGC CTGTCTACGA GTACTCCACC   2700
 E  Y  E    P  S  V    S  H  I  K   R  R  A    S  L  H    E  H  P  P
GCGGGGGCCA AGACCACGGC AGCACGCGGT CCCGTTCCCG ACTCACGGCG TCCGCCGCAC   2760
 A  G  P    E  P  A    T  T  R  W   P  L  P    Q  T  G   C  A  A  H
AGCCTTCACG GCTACAACTG TGTGCGAGGG CGTGCCGGCG TAGGAGCCTA TCTCGATTAC   2820
 R  F  H    R  H  Q    C  V  S    G  C  P  R   M ⟵ ORF3
GACAAAACAC CTATATCTGT GGGCAAAATG GAGTAGTAGT CGCCATACGG CCTCGGCCCT   2880
AGTCCATAAG GCAGGCGTAC GGTCACTCCT CGCAGTACCG CATGGTTGCC CTTTGCAGGT   2940
GCCTA                                                              2945
```

FIG. 2B

```
Nicotine Oxidase   VSSKLATPLS IQGEVIYPDD SGFDAIANIW DGRHLQRPSL IARCLSAGDV   50
MCRA1(P1)          MSTQWGWALE ------PDQ PGYDDARLGL NRAAESRPAY VVEAADEQEV   43
Consensus          .S......L. ......PD. .G.D...... ......RP.. .........V   50

Nicotine Oxidase   AKSVRYACDN GLEISVRSGG HNPNGYATND GGIVLDLRLM NSIHIDTAGS  100
MCRA1(P1)          AAAVRLAAEQ KRPVGYMATG HGPS--VSAD DAVLVNTRRM EGVSVDAARA   91
Consensus          A..VR.A... ......V... .G.H.P.... D......R.M ......D.A.  100

Nicotine Oxidase   RARIGGGVIS GDLVKEAAKF GLAAVTMHP KVGFCGLALN GGVGFLTPKY  150
MCRA1(P1)          TAWIEAGARW RKVLEHTAPH GLAPLNGSSP NYGAVGYLVG GGAGLLGRRF  141
Consensus          .A.I..G... ......A... GLA..G.P.. .VG..G.... GG.G.L....  150

Nicotine Oxidase   GLASDNILGA TLVTATGDVI YCSDDERPEL FWAVRGAGPN FGVVTEVEVQ  200
MCRA1(P1)          GYAADHVRRL RLVTADGRLR DVTAGTDPDL FVAVRGKDN FGLVVGMEVD  191
Consensus          G.A.D..... LVTA.G... ......P.L F.AVRG... NFG.V...EV.  200

Nicotine Oxidase   LYELPRKMLA GFITWAPSVS ELAGLLTSLL DALNEMADHI YPSVFVGVDE  250
MCRA1(P1)          LFPVTR-LYG GGLYFAGEAT --AEVLHAYA EWVRHVPEEM ASSVLLVHNP  238
Consensus          L...R... G....A.... ..A.L..... .......... ........SV....  250

Nicotine Oxidase   NRAPSVTVCV GH-LGGLDIA -ERDIARLRG LGRTVSDSIA VRSYDEVVAL  298
MCRA1(P1)          DLPDVPEPLR GRFITHLRIA YSGEPADGEH LVRPLRELGP ILLDTVRDMP  288
Consensus          .......... G....L.IA ....A..... L.R.......  ..........  300

Nicotine Oxidase   NAEVGSFEDG MSNLWIDREI AMPNARFAEA IAGNLDKFVS EPASGGSVKL  348
MCRA1(P1)          YAEVGTIHHE PTSM--PYVA YDRNVLLSDL TDDAVDIIVA LAGPDAGAPF  336
Consensus          .AEVG..... .......... ....N..... .....D..V. ..........  350

Nicotine Oxidase   EIEGMPFGNP KRTPARHRDA MGVLALAEWS GAAPGSEKYP ELARELDAAL  398
MCRA1(P1)          VTELRHFGGA YARPPKVPNC VGGRDAAFSL FTGAVPEAEG LRRRDQLLDR  386
Consensus          ..E..FG... .P........ .G....A... ......E... ......R...  400

Nicotine Oxidase   LRAGVTTSGF GLLNNNSEVT AEMVAEVYKP EVYCRLAAVK REYDPENRFR  448
MCRA1(P1)          LRPWSTGGTN LNFAGVEDIS PASVEAAYTP ADFARLRAVK AQYDPQNMFR  436
Consensus          LR...T.... .......... ...V...Y.P ....RL.AVK ..YDP.N.FR  450

Nicotine Oxidase   HNYNIDPEGS --                                          458
MCRA1(P1)          VNFNIPPAES WT                                          448
Consensus          .N.N.P..S.                                             462
```

FIG. 3

Probe = 6.7 Kb BclI insert of pDHS3000 (mcr A)

Probe = 4.2 Kb BcII insert of pDHS3001 (mcr B)

*Streptomyces lavendulae* DNA fragment conferring low level resistance to mitomycin C mrd - 4052 bp    8/24/94

```
ACCTATCCGATGTATGCCACCCTCCACGCCTGCCACCCGCGCAGCCTCCAGCG
CACCCTGGCGAAGAAGGGCATCCGTCCGGTCCACGACGTGTCGATCTTCTGGA
CCGGGCAGGACCGCGACGAGCTGCTGCCTTCCCTGCTGGAGGCGGACGTGCA
GCGCGGGCGCGCGGCATTGGCTCTGCTGGAGGAGTCCGATGTCGTGATCGTC
AACCTCACGAGCATCGACCGCTGTTCGCACATCTACTGGCAGGAGCTGGAGCA
CGGCCCCGAGCACGAGCGGAGAGCGCCGTCTTCGCCGCCTACCGCACCTGCG
ACCAGGTCATCCAGGACGCCCTGCGGGCGGCCGACGACCGCACCAGTGTCGT
GGCCTTCTCGGAGATAGGCTTCGGGCCGCTGCGCAACTACTGTTCCATCAACG
ACGAGATGGAGCAGGCGGGTTTCCTGGCCACCGCCGAGGACGGCCGCGTCGA
GTGGGCCGGCAGCGCGGCCTTCGAGGCGGTGCAGGGCACGCACGGGGTGAA
CATCAACCTGCGCGACCGCTACAAGCACGGCCTGGTCCCGGAGCGCGACTAC
GAGAAGGTCCGCACCGACGTCGCGGCCGCCTGCTGGAGCGGCGCAACCCCCG
TACCGGCAGCTGTTCTTCGACGCGGTGCGCCGCCGGGAGGAGGTCTATCCGG
CGAGGCCACCCAGCACGCCCCCGACCTCATCCTGGAGCCGGCGGACTGGCGC
TATCTTCCGCTGGGCGACCCGCACTGGGCCTCGCACGTCCACCGCGACTGGCA
GAGCGGCTGGCACCGCCGGGAGTCCTACTGGTCGGCCGTCGGCCCCGGCTTC
ACCGGTGGGCGCGGCAGACCCGCACCGCCGCCCCGTCGATATTCCCGCGAC
CGTATGCGCTCTGCTCGGGCGTGACGTGCCGAACGACTGGGACGGCGTGCCG
CTGTCCTGAAATCGTTGTCCTGTCAGCGGCGTTGACTCCGGCGGGGATACCC
CGATTGGCCAAAGTCAGCGCGCAGTCACTAGCGTACGGCGCGTCCAGCACATT
CGGACTTCGTGGTCCGGCCGGCCCCGGAGAATTCAGACGGCCCGGCACCGGA
GACCAATTTAAAAGTGCAAGAGAGGAACGCGCATGTCAGCAAGGATTTCCCTC
TTCGCGTGGTGGTCGAGGACATGGCCAAGTCGCTGGAGTTCTACCGGAAGCTG
GGCGTCGAGATCCCCGCCGAGGCCGACTCCGCGCCGCACACGGAGGCCGTGC
TCGACGGCGGCATCCGGCTCGCCTGGGACACCGTGGAGACGGTGCGCAGCTA
CGACCCCGAGTGGCAGGCCCCCACCGGCGGCCACCGCTTCGCCATCGCGTTC
GAGTTCCCCGACACCGCGAGCGTGGACAAGAAGTACGCCGAGCTCGTCGACG
CCGGCTACGAGGGCCACCTCAAGCCGTGGAACGCCGTGTGGGTCAGCGCTA
CGCCATCGTCAAGGACCCCGACGGCAACGTGGTGGACCTCTTCGCGCCCCTCC
CGTAACACCCTGGGCGGGGCCCGGACGCACGCCGCGTCGGCCGGTGCGCCA
GCTCACCGGCACGTTCCCCGAAAGGCGGACATCATGGTCCTACGAGCGCCCG
GGCCGCGCCGCGAGCCACGTCGCGCGATCGCGCCACTGCCCGACCGCAGCGA
ACGGGAAGAACTCTGCGGGCGGGTGACATTCGCCCGCCGGGAATACGGCCCG
GCCCCGGCCGATCTGCTCGCCGTGCCCGGTTCCCTGTCGGCCGCCCCGCTGG
GCACCCTCCGTTCAGGGATCCGCACCGGATTCCTCGGCGGTCCCTGGCAGGAC
GGCTTCCCGCGCTATGTCTGGCACCGGTCCGGTACTCCGTCGTGGAATTCCGG
CTGACGGCCGTGCGCCGGGCGAATACACCGGATACGAACTCCACCCGAGCGA
ATGGCCGGAAGGGGTGGCGGACCATGCTTCCTGAGTTCCAATTGCAGTGGAAT
TGGCTCGACGCCCCGGCCGGCGGCGGAGGCGAGCTGCAAGCGACCTGGGCC
CGGCTGCGCATCGCCGTGGGCGCCGAGACCGTCACACTCGTCCAGGAGCCCG
GGCAGGGGACCTTCCGGGAGCACACGACCGGCTCGCTCTACCCCCTGGCCGA
GTGGATCGCCTTCAACTGGTGGTCGCTGGTGGCCGACGCGCGGCCCGGCACC
CAGATATCCCAGCTGCGCTTCGCCTACCGCCACGGTGTGGGCGACAACCGCGG
TTCGTGGTGGATGCGTTCGCGCCGTCACATCCTGCGCGCCGCCTGCGACGGCT
TCCGCTGGCCGGACATGCTCTTCGTGCCCGAGGGCCGGGAGACCCGGATCGT
ATGGATGCCGGACATGGGCCCCGACGTACGACCCGGGAACCGCTTCGCGAGC
CGGGGCAACTCCTGTGTGGAGAGCGCCGCGTTCACCGCCACACTGGCCTCGTT
CGTCGACGCGGTGACCGAGCGCCTCACGGACCAGGGCATCACCGGCACCCCG
CTCCAGGAGGAGTGGGCCGCCGTCCGCGCCACCGACGAGGACGAGGCCGCCT
TCTGCCGCATCGGACGGCTGGGCCTGGACCCCTACGCCGAGGCCGAGCCGTA
```

FIG. 11A

```
CGAGGCGGACATGCCTCAAGGCCGCCGAGCAGTTGGCGGAACCGTCGCCAGT
GACTTCTTCAACGGGGTGCGGCCTGAGCGGATAGCCGACCAGCTCCAGTGGAT
CGCGCGCGTCCGCACCCTGATGGGCACCGCGCCCGCGGATACCCCGCTCCCT
CCCGCCTTGGTGGAACTGCGCAAGGACTGCGCCGACTTGAGCGAGAAGTTCTT
CCGCTCCGGGGCGACTCGACAACCCCTGGGACCTCGGCTACGAGGTGCGCAC
CGGGTGCGCGCGTGGGCGGGTCTGGACGACACCGCGCCCTTCGACCCGGCCC
CCCTGATGGGCTACCGCACCGAGCAGGTCCCCTATATGGACCGGGGCCTGGTC
GCCCTCGGCACCCGCAGGGGCGCGGACGGGCCGGTCCTGGTCTCCTCCCGGC
GCTTCACCGACCGCCCGCGCCGCTTCCTCCAGGCCCGCGCGCTGTGGCATCTG
ATCTGCGACCCCGACGACACCTTCCTGATTCGCGGCGGCGCACACCCACCGCC
AGCACGTGGCCCGCGCTTCGCCCTGGAGGTCCTGGCCCCCGCCAAGGGCGTG
GCGACCCTGCTGGCCGACCCCGGACACCTGGTGTCCGCCGAGGACGTCGAGG
TCATCGCCGACGACTACGGCTGCGGCAACATCGTCGTGGAACACCAGCTGGAC
AACCGCGTCCTGGCGAAGGACTTCACCTGGCCCGGGCCACGCGCCGCCGGCG
CGCCGGCCGGTGAGAGGAGCCGGGGCGCATGACCTCAGCCGCCCCGCCCGC
CTTTCCCTTCCCGCCCGGCCCCGGCGGCACGGTGCCGCCCGAGTACGCGCGG
CTGCTCACCGATGACCCGGTCGCCGAGGTGCGCCTGGCGGACGGCTCGCGCA
TCTGGCTGGTGACCCGGCACGAGGACGTGCGCACGGTGCTCACCGACGGCCG
CTTCAGCCGCCATCGCGCCGCCATGCTGCCGGGCTCGGGCTTCGGCCGGTCCC
AGGGCTCGGGCATCGTGGACCTCGACCCGCCGGAGCACGGCCGGCTGGCGC
GGTCCGGTGGTGGCCGCGTTCGGTGCCTGCGCACGGCGCGGTTCGCACCCCG
CATCGAGGCGGCCGCCGAGGCGGCCCTGGACCGGCTGCCCGCCGGCAGCGG
CACGGTGGACCTCGTCGCGGCGTACACCGCCCCTTCGCCGGCCCGCGTCACA
GCCGAGTTCCTCGGGCTGCCCGGGGACCGTGGCAGGACGTCACCTCCGACGT
CGAGCTGCTGCTGCTTCCGCGCGGTGCCACCGAGCAGGCGCTGGAAGGAGGC
CCTGCGGCAGGCTCGGCCAGGTGCTGGACGAACTGCTCGCGGCCCGCAGGGC
CGAGCCGGGCGACAGCGTCACCGACACGCTGCTGGACGCGGAGGAGCTCACC
GACGACGACCGGCGCCTGCTGCTCCACGGCC
```

FIG. 11B

SEQUENCE LISTING

<160> NUMBER OF SEQ ID NOS: 18

<210> SEQ ID NO 1
<211> LENGTH: 1474
<212> TYPE: DNA
<213> ORGANISM: Streptomyces lavendulae
<220> FEATURE:
<221> NAME/KEY: CDS
<222> LOCATION: (131)...(1474)

<400> SEQUENCE: 1

```
gatcttcctc gttttgggga ggtgctgacg agccggcctt cgcgccgggc ttccccgcgg       60
gcaggcgctc ccacaaccat gtccgattcc ttcaagatgc cgccttgagc tgcttgatta      120
catggcgcgc atg agc acg caa tgg gga tgg gcc ctt gag ccg gac cag         169
            Met Ser Thr Gln Trp Gly Trp Ala Leu Glu Pro Asp Gln
              1               5                  10 ccg gga tac gac gac gcc cgg ctg gga ctg aac cgg gcg gcc gaa tcg        217
Pro Gly Tyr Asp Asp Ala Arg Leu Gly Leu Asn Arg Ala Ala Glu Ser
 15                  20                  25 cgg ccg gcc tac gtg gtc gag gcg gcc gac gag cag gag gtg gcc gcc        265
Arg Pro Ala Tyr Val Val Glu Ala Ala Asp Glu Gln Glu Val Ala Ala
 30                  35                  40                  45 gcg gtg agg ctg gcc gcc gag cag aaa cgg ccc gtg ggt gtg atg gcc        313
Ala Val Arg Leu Ala Ala Glu Gln Lys Arg Pro Val Gly Val Met Ala
                 50                  55                  60 acc ggt cac gga ccg tcc gtg tcg gcc gac gac gcc gtg ctg gtc aac        361
Thr Gly His Gly Pro Ser Val Ser Ala Asp Asp Ala Val Leu Val Asn
                 65                  70                  75 acg cgg cgg atg gaa ggt gtg agc gtt gac gcg gcc cgc gcg acg gca        409
Thr Arg Arg Met Glu Gly Val Ser Val Asp Ala Ala Arg Ala Thr Ala
     80                  85                  90 tgg atc gaa gcc ggg gca cgc tgg cgg aag gtg ctg gaa cac acc gct        457
Trp Ile Glu Ala Gly Ala Arg Trp Arg Lys Val Leu Glu His Thr Ala
     95                 100                 105 ccg cac ggg ctc gcg ccg ctg aac ggc tcg agc ccc aac gtg ggc gct        505
```

```
Pro His Gly Leu Ala Pro Leu Asn Gly Ser Ser Pro Asn Val Gly Ala
110             115                 120                 125 gtc ggc tat ctg gtc ggc ggc gcg gga ctg ctg ggc cgc cgg ttc         553
Val Gly Tyr Leu Val Gly Gly Ala Gly Leu Leu Gly Arg Arg Phe
            130                 135                 140 ggc tac gcc gcc gac cac gta cgg cgg ctg cgc ctg gtc acc gcc gac     601
Gly Tyr Ala Ala Asp His Val Arg Arg Leu Arg Leu Val Thr Ala Asp
                145                 150                 155 ggc cgc ttg cgc gac gtg acg gcc ggg acc gac ccc gac ctg ttc tgg     649
Gly Arg Leu Arg Asp Val Thr Ala Gly Thr Asp Pro Asp Leu Phe Trp
        160                 165                 170 gcg gtc cgc ggc ggc aag gac aac ttc ggc ctg gtc gtg ggc atg gag     697
Ala Val Arg Gly Gly Lys Asp Asn Phe Gly Leu Val Val Gly Met Glu
        175                 180                 185 gtc gac ctg ttc ccg gtc acc cgg ctc tac ggc gga ggg ctc tac ttc     745
Val Asp Leu Phe Pro Val Thr Arg Leu Tyr Gly Gly Gly Leu Tyr Phe
190             195                 200                 205 gcg ggc gag gcc acc gcc gag gtg ctg cac gcc tac gcc gag tgg gtc     793
Ala Gly Glu Ala Thr Ala Glu Val Leu His Ala Tyr Ala Glu Trp Val
                210                 215                 220 cgg cac gtg ccc gag gag atg gcg tcc tcc gtg ctg ctc gtc cac aac     841
Arg His Val Pro Glu Glu Met Ala Ser Ser Val Leu Leu Val His Asn
                225                 230                 235 ccc gac ctg ccc gac gtc ccg gaa ccg ctg cgc gga cgc ttc atc acc     889
Pro Asp Leu Pro Asp Val Pro Glu Pro Leu Arg Gly Arg Phe Ile Thr
        240                 245                 250 cac ctc cgc atc gcc tac agc ggc gaa ccg gca gac ggc gag cac ttg     937
His Leu Arg Ile Ala Tyr Ser Gly Glu Pro Ala Asp Gly Glu His Leu
        255                 260                 265 gtg cgg ccg cta cgc gaa ctc gga ccc atc ctc ctc gac acc gtg cgg     985
Val Arg Pro Leu Arg Glu Leu Gly Pro Ile Leu Leu Asp Thr Val Arg
270             275                 280                 285 gac atg ccc tac gcc gag gtc ggc acg att cat cac gag ccc acg tcc    1033
Asp Met Pro Tyr Ala Glu Val Gly Thr Ile His His Glu Pro Thr Ser
                290                 295                 300 atg ccg tac gtc gcg tac gac cgc aac gtg ttg ctg agc gac ctg acc    1081
Met Pro Tyr Val Ala Tyr Asp Arg Asn Val Leu Leu Ser Asp Leu Thr
                305                 310                 315 gac gat gcc gtc gac atc atc gtc gcc ctg gcc gga ccg gac gca ggg    1129
Asp Asp Ala Val Asp Ile Ile Val Ala Leu Ala Gly Pro Asp Ala Gly
        320                 325                 330 gcg ccg ttc gtc acc gaa ctg cgg cac ttc ggc ggc gcg tac gcc cgt    1177
Ala Pro Phe Val Thr Glu Leu Arg His Phe Gly Gly Ala Tyr Ala Arg
        335                 340                 345 ccg ccg aag gtc ccc aac tgc gtg ggc ggg cgc gac gcg gcc ttc tcg    1225
Pro Pro Lys Val Pro Asn Cys Val Gly Gly Arg Asp Ala Ala Phe Ser
350             355                 360                 365 ctc ttc acg ggc gcc gtc ccg gaa gcc gag ggt ctc cgg cgc cgt gat    1273
Leu Phe Thr Gly Ala Val Pro Glu Ala Glu Gly Leu Arg Arg Arg Asp
        370                 375                 380 gac ctg ctc gac cgg ctg cgc cca tgg agc acc ggc ggc acg aac ctc    1321
Asp Leu Leu Asp Arg Leu Arg Pro Trp Ser Thr Gly Gly Thr Asn Leu
        385                 390                 395 aat ttc gcc ggt gtc gag gac atc agc ccg gcg agc gtg gaa gcc gcc    1369
Asn Phe Ala Gly Val Glu Asp Ile Ser Pro Ala Ser Val Glu Ala Ala
                400                 405                 410 tac act ccg gct gat ttc gcc cgg ttg agg gct gtc aag gcc caa tac    1417
Tyr Thr Pro Ala Asp Phe Ala Arg Leu Arg Ala Val Lys Ala Gln Tyr
        415                 420                 425
```

```
gac ccg gac aac atg ttc cga gtc aac ttc aac att ccg ccg gcg gag    1465
Asp Pro Asp Asn Met Phe Arg Val Asn Phe Asn Ile Pro Pro Ala Glu
430                 435                 440                 445 tct tgg acg                                                         1474
Ser Trp Thr
```

<210> SEQ ID NO 2
<211> LENGTH: 386
<212> TYPE: DNA
<213> ORGANISM: Streptomyces lavendulae
<220> FEATURE:
<221> NAME/KEY: CDS
<222> LOCATION: (53)...(367)

<400> SEQUENCE: 2

```
tgagcgtagc gaccgagcct gtccggcgtc gtcatggaga gaaggagtcc gg gtg acc    58
                                                         Val Thr
                                                           1 tca tcc gac gga tcg gac ctc acc act ctg gtc aac gtg ggc cgg tcc    106
Ser Ser Asp Gly Ser Asp Leu Thr Thr Leu Val Asn Val Gly Arg Ser
        5                  10                  15 gtg gcg agg tac ttc gag cgc atc ggc atc acc gag atc gcg caa ctg    154
Val Ala Arg Tyr Phe Glu Arg Ile Gly Ile Thr Glu Ile Ala Gln Leu
 20                  25                  30 cgg gac cgc gat ccg gtc gag ttg tac gag cgg atg tca gcc gcc ttc    202
Arg Asp Arg Asp Pro Val Glu Leu Tyr Glu Arg Met Ser Ala Ala Phe
 35                  40                  45                  50 ggg cag cgc ctc gat ccc tgc ctg ctc gac acc gtc atg tcg gcg gtg    250
Gly Gln Arg Leu Asp Pro Cys Leu Leu Asp Thr Val Met Ser Ala Val
                 55                  60                  65 gac cag gcc gaa ggc ctg ccc gct cgc ccc tgg tgg cac tac acc ccg    298
Asp Gln Ala Glu Gly Leu Pro Ala Arg Pro Trp Trp His Tyr Thr Pro
             70                  75                  80 gag cgc aag cgg ttg ctg gca ggc gaa ggc cat gac cgg gcc ggt gga    346
Glu Arg Lys Arg Leu Leu Ala Gly Glu Gly His Asp Arg Ala Gly Gly
         85                  90                  95 acc gcg ggg gag ggg aca gcg tagagacaca gccgtgagt                    386
Thr Ala Gly Glu Gly Thr Ala
    100             105
```

<210> SEQ ID NO 3
<211> LENGTH: 1085
<212> TYPE: DNA
<213> ORGANISM: Streptomyces lavendulae

<400> SEQUENCE: 3

```
gaagggaaa cggcaggaga gggccggccc ggcacggagt ggcccgtcag caatggccgg     60
acgggttcac accgccggtg tacgcgagcg gccgggtcac ctctccacca gttcgctcag   120
gcttgagggg cggtagaggg catgtagtgc cggtctact cggaccaggc gcttcgggcg    180
gtcgcagcgg cagaggcgct tccctgtgg ccgcgcccgg tccgcgtccc gcgcgacgta    240
cgcgtcctgt gccggtccc agaacccagg catcggcttc cgccggtccc ttgccgccac    300
ctcgacggcg cgcggctctg gtggctcag ccgccagcga cactgcctcg ctggccgaag    360
ctccctgtgg tgctgacgag cgtcctgccc cagctgccca aggcgcagcc ggcgctgcgg    420
cgttacggtc taggagctcc cgccgccggc ccaggccggc ggcggcagct gcgcaagcca    480
ctctgccgcg cagggccgcg gcccggtctc agccgctct agctgagcga ccagggcgtc    540
gagtacgcgc ccctacggc cgtcccgccc cgctacggc cccctcttcg cctgtgggtg     600
ggtcttcggg gccactcacg acatccgcga acatagcccg ggcctctgct cctcggccgg    660
```

-continued

```
acggcaggtg tcgtccagct acgtcggcag tccattgtgc cagcagcaga gcggcggtgg    720
ccatgtgggc cgcgaggga cgtgggtcgg ctagcgcggg ccgtcggccc tgcacgcgag    780
aagcatgagc ccctgtgcg acacttaaaa tgcggagcgc ctgtctacga gtactccacc    840
gcggggccca agaccacggc agcacgcggt cccgttcccg actcacggcg tccgccgcac    900
agccttcacg gctacaactg tgtgcgaggg cgtgccggcg taggagccta tctcgattac    960
gacaaaacac ctatatctgt gggcaaaatg gagtagtagt cgccatacgg cctcggccct   1020
agtccataag gcaggcgtac ggtcactcct cgcagtaccg catggttgcc ctttgcaggt   1080
gccta                                                               1085
```

<210> SEQ ID NO 4
<211> LENGTH: 458
<212> TYPE: PRT
<213> ORGANISM: Arthrobacter oxidans

<400> SEQUENCE: 4

```
Val Ser Ser Lys Leu Ala Thr Pro Leu Ser Ile Gln Gly Glu Val Ile
  1               5                  10                  15

Tyr Pro Gln Asp Ser Gly Phe Asp Ala Ile Ala Asn Ile Trp Asp Gly
             20                  25                  30

Arg His Leu Gln Arg Pro Ser Leu Ile Ala Arg Cys Leu Ser Ala Gly
         35                  40                  45

Asp Val Ala Lys Ser Val Arg Tyr Ala Cys Asp Asn Gly Leu Glu Ile
     50                  55                  60

Ser Val Arg Ser Gly Gly His Asn Pro Asn Gly Tyr Ala Thr Asn Asp
 65                  70                  75                  80

Gly Gly Ile Val Leu Asp Leu Arg Leu Met Asn Ser Ile His Ile Asp
                 85                  90                  95

Thr Ala Gly Ser Arg Ala Arg Ile Gly Gly Val Ile Ser Gly Asp
            100                 105                 110

Leu Val Lys Glu Ala Ala Lys Phe Gly Leu Ala Ala Val Thr Gly Met
        115                 120                 125

His Pro Lys Val Gly Phe Cys Gly Leu Ala Leu Asn Gly Gly Val Gly
    130                 135                 140

Phe Leu Thr Pro Lys Tyr Gly Leu Ala Ser Asp Asn Ile Leu Gly Ala
145                 150                 155                 160

Thr Leu Val Thr Ala Thr Gly Asp Val Ile Tyr Cys Ser Asp Asp Glu
                165                 170                 175

Arg Pro Glu Leu Phe Trp Ala Val Arg Gly Ala Gly Pro Asn Phe Gly
            180                 185                 190

Val Val Thr Glu Val Glu Val Gln Leu Tyr Glu Leu Pro Arg Lys Met
        195                 200                 205

Leu Ala Gly Phe Ile Thr Trp Ala Pro Ser Val Ser Glu Leu Ala Gly
    210                 215                 220

Leu Leu Thr Ser Leu Leu Asp Ala Leu Asn Glu Met Ala Asp His Ile
225                 230                 235                 240

Tyr Pro Ser Val Phe Val Gly Val Asp Glu Asn Arg Ala Pro Ser Val
                245                 250                 255

Thr Val Cys Val Gly His Leu Gly Gly Leu Asp Ile Ala Glu Arg Asp
            260                 265                 270

Ile Ala Arg Leu Arg Gly Leu Gly Arg Thr Val Ser Asp Ser Ile Ala
        275                 280                 285
```

-continued

```
Val Arg Ser Tyr Asp Glu Val Ala Leu Asn Ala Glu Val Gly Ser
    290                 295                 300

Phe Glu Asp Gly Met Ser Asn Leu Trp Ile Asp Arg Glu Ile Ala Met
305                 310                 315                 320

Pro Asn Ala Arg Phe Ala Glu Ala Ile Ala Gly Asn Leu Asp Lys Phe
                325                 330                 335

Val Ser Glu Pro Ala Ser Gly Gly Ser Val Lys Leu Glu Ile Glu Gly
                340                 345                 350

Met Pro Phe Gly Asn Pro Lys Arg Thr Pro Ala Arg His Arg Asp Ala
            355                 360                 365

Met Gly Val Leu Ala Leu Ala Glu Trp Ser Gly Ala Ala Pro Gly Ser
    370                 375                 380

Glu Lys Tyr Pro Glu Leu Ala Arg Glu Leu Asp Ala Ala Leu Leu Arg
385                 390                 395                 400

Ala Gly Val Thr Thr Ser Gly Phe Gly Leu Leu Asn Asn Asn Ser Glu
                405                 410                 415

Val Thr Ala Glu Met Val Ala Glu Val Tyr Lys Pro Glu Val Tyr Cys
                420                 425                 430

Arg Leu Ala Ala Tyr Lys Arg Glu Tyr Asp Pro Glu Asn Arg Phe Arg
            435                 440                 445

His Asn Tyr Asn Ile Asp Pro Glu Gly Ser
    450                 455

<210> SEQ ID NO 5
<211> LENGTH: 448
<212> TYPE: PRT
<213> ORGANISM: Streptomyces lavendulae

<400> SEQUENCE: 5

Met Ser Thr Gln Trp Gly Trp Ala Leu Glu Pro Asp Gln Pro Gly Tyr
1               5                   10                  15

Asp Asp Ala Arg Leu Gly Leu Asn Arg Ala Ala Glu Ser Arg Pro Ala
                20                  25                  30

Tyr Val Glu Ala Ala Asp Glu Gln Glu Val Ala Ala Ala Val Arg
            35                  40                  45

Leu Ala Ala Glu Gln Lys Arg Pro Val Gly Val Met Ala Thr Gly His
    50                  55                  60

Gly Pro Ser Val Ser Ala Asp Ala Val Leu Val Asn Thr Arg Arg
65                  70                  75                  80

Met Glu Gly Val Ser Val Asp Ala Ala Arg Ala Thr Ala Trp Ile Glu
                85                  90                  95

Ala Gly Ala Arg Trp Arg Lys Val Leu Glu His Thr Ala Pro His Gly
            100                 105                 110

Leu Ala Pro Leu Asn Gly Ser Ser Pro Asn Val Gly Ala Val Gly Tyr
        115                 120                 125

Leu Val Gly Gly Gly Ala Gly Leu Leu Gly Arg Arg Phe Gly Tyr Ala
    130                 135                 140

Ala Asp His Val Arg Arg Leu Arg Leu Val Thr Ala Asp Gly Arg Leu
145                 150                 155                 160

Arg Asp Val Thr Ala Gly Thr Asp Pro Asp Leu Phe Trp Ala Val Arg
                165                 170                 175

Gly Gly Lys Asp Asn Phe Gly Leu Val Val Gly Met Glu Val Asp Leu
            180                 185                 190

Phe Pro Val Thr Arg Leu Tyr Gly Gly Leu Tyr Phe Ala Gly Glu
        195                 200                 205
```

Ala Thr Ala Glu Val Leu His Ala Tyr Ala Glu Trp Val Arg His Val
    210                 215                 220

Pro Glu Glu Met Ala Ser Ser Val Leu Leu Val His Asn Pro Asp Leu
225                 230                 235                 240

Pro Asp Val Pro Glu Pro Leu Arg Gly Arg Phe Ile Thr His Leu Arg
                245                 250                 255

Ile Ala Tyr Ser Gly Glu Pro Ala Asp Gly Glu His Leu Val Arg Pro
                260                 265                 270

Leu Arg Glu Leu Gly Pro Ile Leu Leu Asp Thr Val Arg Asp Met Pro
            275                 280                 285

Tyr Ala Glu Val Gly Thr Ile His His Glu Pro Thr Ser Met Pro Tyr
    290                 295                 300

Val Ala Tyr Asp Arg Asn Val Leu Leu Ser Asp Leu Thr Asp Asp Ala
305                 310                 315                 320

Val Asp Ile Ile Val Ala Leu Ala Gly Pro Asp Ala Gly Ala Pro Phe
                325                 330                 335

Val Thr Glu Leu Arg His Phe Gly Gly Ala Tyr Ala Arg Pro Pro Lys
            340                 345                 350

Val Pro Asn Cys Val Gly Gly Arg Asp Ala Ala Phe Ser Leu Phe Thr
            355                 360                 365

Gly Ala Val Pro Glu Ala Glu Gly Leu Arg Arg Arg Asp Asp Leu Leu
    370                 375                 380

Asp Arg Leu Arg Pro Trp Ser Thr Gly Gly Thr Asn Leu Asn Phe Ala
385                 390                 395                 400

Gly Val Glu Asp Ile Ser Pro Ala Ser Val Glu Ala Ala Tyr Thr Pro
                405                 410                 415

Ala Asp Phe Ala Arg Leu Arg Ala Val Lys Ala Gln Tyr Asp Pro Asp
            420                 425                 430

Asn Met Phe Arg Val Asn Phe Asn Ile Pro Pro Ala Glu Ser Trp Thr
    435                 440                 445

<210> SEQ ID NO 6
<211> LENGTH: 12
<212> TYPE: PRT
<213> ORGANISM: Artificial Sequence
<220> FEATURE:
<221> NAME/KEY: UNSURE
<222> LOCATION: (1)...(2)
<223> OTHER INFORMATION: Unsure
<220> FEATURE:
<221> NAME/KEY: UNSURE
<222> LOCATION: (11)...(11)
<223> OTHER INFORMATION: Unsure
<223> OTHER INFORMATION: A polypeptide

<400> SEQUENCE: 6

Xaa Xaa Thr Gln Trp Gly Trp Ala Leu Glu Xaa Asp
 1               5                  10

<210> SEQ ID NO 7
<211> LENGTH: 10
<212> TYPE: PRT
<213> ORGANISM: Artificial Sequence
<220> FEATURE:
<221> NAME/KEY: UNSURE
<222> LOCATION: (9)...(9)
<223> OTHER INFORMATION: Unsure
<223> OTHER INFORMATION: A polypeptide

<400> SEQUENCE: 7

Thr Gln Trp Gly Trp Ala Leu Glu Xaa Asp
 1               5                  10

<210> SEQ ID NO 8
<211> LENGTH: 21
<212> TYPE: DNA
<213> ORGANISM: Streptomyces lavendulae

<400> SEQUENCE: 8
cctgttctgg gcggtccgcg g                                             21

<210> SEQ ID NO 9
<211> LENGTH: 24
<212> TYPE: DNA
<213> ORGANISM: Streptomyces lavendulae

<400> SEQUENCE: 9
tacgacccgg acaacatgtt ccga                                          24

<210> SEQ ID NO 10
<211> LENGTH: 20
<212> TYPE: DNA
<213> ORGANISM: Streptomyces lavendulae

<400> SEQUENCE: 10
ccacctcctg ctcgtcggcc                                               20

<210> SEQ ID NO 11
<211> LENGTH: 4052
<212> TYPE: DNA
<213> ORGANISM: Streptomyces lavendulae

<400> SEQUENCE: 11
acctatccga tgtatgccac cctccacgcc tgccaccgc gcagcctcca gcgcaccctg      60
gcgaagaagg gcatccgtcc ggtccacgac gtgtcgatct tctggaccgg caggaccgc    120
gacgagctgc tgccttccct gctggaggcg gacgtgcagc gcgggcgcgc ggcattggct    180
ctgctggagg agtccgatgt cgtgatcgtc aacctcacga gcatcgaccg ctgttcgcac    240
atctactggc aggagctgga gcacggcccc gagcacgagc ggagagcgcc gtcttcgccg    300
cctaccgcac ctgcgaccag gtcatccagg acgccctgcg ggcggccgac gaccgcacca    360
gtgtcgtggc cttctcggag ataggcttcg ggccgctgcg caactactgt tccatcaacg    420
acgagatgga gcaggcgggt ttcctggcca ccgccgagga cggccgcgtc gagtgggccg    480
gcagcgcggc cttcgaggcg gtgcagggca cgcacgggt gaacatcaac ctgcgcgacc    540
gctacaagca cggcctggtc ccggagcgcg actacgagaa ggtccgcacc gacgtcgcgg    600
ccgcctgctg gagcggcgca accccgtac cggcagctgt tcttcgacgc ggtgcgccgc    660
cgggaggagg tctatccggc gaggccaccc agcacgcccc cgacctcatc ctggagccgg    720
cggactggcg ctatcttccg ctgggcgacc cgcactgggc ctcgcacgtc caccgcgact    780
ggcactggcg ctatcttccg ctgggcgacc cgcactgggc ctcgcacgtc caccgcgact    840
gtgggcgcgg cagacccgca ccgccgcccc cgtcgatatt cccgcgaccg tatgcgctct    900
gctcgggcgt gacgtgccga acgactggga cggcgtgccg ctgtcctgaa atcgttgtcc    960
tgtcagcggc gttgactccg gcgggggata ccccgattgg ccaaagtcag cgcgcagtca   1020
ctagcgtacg gcgcgtccag cacattcgga cttcgtggtc cggccggccc cggagaattc   1080
agacggcccg gcaccggaga ccaatttaaa agtgcaagag aggaacgcgc atgtcagcaa   1140

```
ggatttccct cttcgcgtgg tggtcgagga catggccaag tcgctggagt tctaccggaa    1200
gctgggcgtc gagatccccg ccgaggccga ctccgcgccg cacacggagg ccgtgctcga    1260
cggcggcatc cggctcgcct gggacaccgt ggagacggtg cgcagctacg accccgagtg    1320
gcaggccccc accggcggcc accgcttcgc catcgcgttc gagttccccg acaccgcgag    1380
cgtggacaag aagtacgccg agctcgtcga cgccggctac gagggccacc tcaagccgtg    1440
gaacgccgtg tggggtcagc gctacgccat cgtcaaggac cccgacggca cgtggtgga    1500 cctcttcgcg cccctcccgt aacaccctgg cggggcccg gacgcacgcc gcgtcggccg    1560
gtgcgccagc tcaccggcac gttccccgaa aggcggacat catggtccta cgagcgcccg    1620
ggccgcgccg cgagccacgt cgcgcgatcg cgccactgcc cgaccgcagc gaacgggaag    1680
aactctgcgg gcgggtgaca ttcgcccgcc gggaatacgg cccggccccg gccgatctgc    1740
tcgccgtgcc cggttccctg tcggccgccc cgctgggcac cctccgttca gggatccgca    1800
ccggattcct cggcggtccc tggcaggacg gcttcccgcg ctatgtctgg caccggtccg    1860
gtactccgtc gtggaattcc ggctgacggc cgtgcgccgg gcgaatacac cggatacgaa    1920
ctccacccga gcgaatggcc ggaagggtg gcggaccatg cttcctgagt tccaattgca    1980
gtggaattgg ctcgacgccc cggccggcgg cggaggcgag ctgcaagcga cctgggcccg    2040
gctgcgcatc gccgtgggcg ccgagaccgt cacactcgtc caggagcccg ggcaggggac    2100
cttccgggag cacacgaccg gctcgctcta cccctggcc gagtggatcg ccttcaactg    2160
gtggtcgctg gtggccgacg cgcggcccgg cacccagata tccagctgc gcttcgccta    2220 ccgccacggt gtgggcgaca accgcggttc gtggtggatg cgttcgcgcc gtcacatcct    2280
gcgcgccgcc tgcgacggct ccgctgccc ggacatgctc ttcgtgcccg agggccggga    2340
gacccggatc gtatggatgc cggacatggg ccccgacgta cgacccggga accgcttcgc    2400
gagccggggc aactcctgtg tggagagcgc cgcgttcacc gccacactgg cctcgttcgt    2460
cgacgcggtg accgagcgcc tcacggacca gggcatcacc ggcaccccgc tccaggagga    2520
gtgggccgcc gtccgcgcca ccgacgagga cgaggccgcc ttctgccgca tcggacggct    2580
gggcctggac ccctacgccg aggccgagcc gtacgaggcg acatgcctc aaggccgccg    2640 agcagttggc ggaaccgtcg ccagtgactt cttcaacggg gtgcggcctg agcggatagc    2700
cgaccagctc cagtggatcg cgcgcgtccg caccctgatg ggcaccgcgc ccgcggatac    2760
cccgctccct cccgccttgg tggaactgcg caaggactgc gcggacttga gcagaagtt    2820 cttccgctcc ggggcgactc gacaaccct gggacctcgg ctacgaggtg cgcaccgggt    2880
gcgcgcgtgg gcgggtctgg acgacaccgc gcccttcgac ccggcccccc tgatgggcta    2940
ccgcaccgag caggtcccct atatggaccg gggcctggtc gccctcggca cccgcagggg    3000
cgcggacggg ccggtcctgg tctcctcccg gcgcttcacc gaccgccgc gccgcttcct    3060 ccaggcccgc gcgctgtggc atctgatctg cgaccccgac gacaccttcc tgattcgcgg    3120
cggcgcacac ccaccgccag cacgtggccc gcgcttcgcc ctggaggtcc tggccccgc    3180 caagggcgtg gcgaccctgc tggccgaccc cggacacctg gtgtccgccg aggacgtcga    3240
ggtcatcgcc gacgactacg gctgcggcaa catcgtcgtg aacaccagc tggacaaccg    3300 cgtcctggcg aaggacttca cctggcccgg gccacgcgcc gccggcgcgc cggccggtga    3360
gaggagccgg ggcgcatgac ctcagccgcc ccgcccgcct ttcccttccc gcccggcccc    3420
ggcggcacgg tgccgcccga gtacgcgcgg ctgctcaccg atgacccggt cgccgaggtg    3480
cgcctggcgg acggctcgcg catctggctg gtgacccggc acgaggacgt gcgcacggtg    3540
```

```
ctcaccgacg gccgcttcag ccgccatcgc gccgccatgc tgccgggctc gggcttcggc    3600
cggtcccagg gctcgggcat cgtggacctc gacccgccgg agcacggccg gctggcgcgg    3660
tccggtggtg gccgcgttcg gtgcctgcgc acggcgcggt cgcacccccg catcgaggcg    3720
gccgccgagg cggccctgga ccggctgccc gccggcagcg gcacggtgga cctcgtcgcg    3780
gcgtacaccg cccttcgcc ggcccgcgtc acagccgact tcctcgggct gcccggggac    3840
cgtggcagga cgtcacctcc gacgtcgagc tgctgctgct ccgcgcggt gccaccgagc    3900 aggcgctgga aggaggccct gcggcaggct cggccaggt ctggacgaac tgctcgcggc    3960
ccgaggggcc gagccgggcg acagcgtcac cgacacgctg ctggacgcgg aggagctcac    4020
cgacgacgac cggcgcctgc tgctccacgg cc                                  4052
```

<210> SEQ ID NO 12
<211> LENGTH: 16
<212> TYPE: PRT
<213> ORGANISM: Streptomyces lavendulae

<400> SEQUENCE: 12

Met Ser Thr Gln Trp Gly Trp Ala Leu Glu Pro Asp Gln Pro Gly Tyr
1               5                   10                  15

<210> SEQ ID NO 13
<211> LENGTH: 11
<212> TYPE: PRT
<213> ORGANISM: Streptomyces lavendulae

<400> SEQUENCE: 13

Ser Thr Gln Trp Gly Trp Ala Leu Glu Pro Asp
1               5                   10

<210> SEQ ID NO 14
<211> LENGTH: 7
<212> TYPE: PRT
<213> ORGANISM: Streptomyces lavendulae

<400> SEQUENCE: 14

Leu Phe Trp Ala Val Arg Gly
1               5

<210> SEQ ID NO 15
<211> LENGTH: 8
<212> TYPE: PRT
<213> ORGANISM: Streptomyces lavendulae

<400> SEQUENCE: 15

Tyr Asp Pro Asp Asn Met Phe Arg
1               5

<210> SEQ ID NO 16
<211> LENGTH: 12
<212> TYPE: PRT
<213> ORGANISM: Streptomyces lavendulae

<400> SEQUENCE: 16

Met Ser Thr Gln Trp Gly Trp Ala Leu Glu Pro Asp
1               5                   10

<210> SEQ ID NO 17
<211> LENGTH: 105
<212> TYPE: PRT
<213> ORGANISM: Streptomyces lavendulae

<400> SEQUENCE: 17

Met Thr Ser Ser Asp Gly Ser Asp Leu Thr Thr Leu Val Asn Val Gly
1               5                   10                  15

Arg Ser Val Ala Arg Tyr Phe Glu Arg Ile Gly Ile Thr Glu Ile Ala
            20                  25                  30

Gln Leu Arg Asp Arg Asp Pro Val Glu Leu Tyr Glu Arg Met Ser Ala
        35                  40                  45

Ala Phe Gly Gln Arg Leu Asp Pro Cys Leu Leu Asp Thr Val Met Ser
50                  55                  60

Ala Val Asp Gln Ala Glu Gly Leu Pro Ala Arg Pro Trp Trp His Tyr
65                  70                  75                  80

Thr Pro Glu Arg Lys Arg Leu Leu Ala Gly Gly His Asp Arg Ala
            85                  90                  95

Gly Gly Thr Ala Gly Glu Gly Thr Ala
            100                 105

<210> SEQ ID NO 18
<211> LENGTH: 281
<212> TYPE: PRT
<213> ORGANISM: Streptomyces lavendulae

<400> SEQUENCE: 18

Met Arg Pro Cys Gly Ser Val Cys Gln His Arg His Phe Arg His Ala
1               5                   10                  15

Ala Cys Gly Thr Gln Pro Leu Pro Trp Arg Thr Thr Ala Pro Glu Pro
            20                  25                  30

Gly Ala Pro Pro His Glu His Leu Ser Ala Arg Arg Lys Ile His Ser
        35                  40                  45

Val Ser Pro Glu Tyr Glu Glu Arg Thr Ser Arg Leu Pro Gly Ala Ile
50                  55                  60

Gly Trp Val Gln Gly Ala Pro Gly Cys Thr Gly Gly Glu Thr Thr
65                  70                  75                  80

Thr Val Leu Pro Asp Gly Cys Ile Asp Leu Leu Trp Thr Ala Gly Arg
            85                  90                  95

Leu Leu Val Ser Gly Pro Asp Thr Ser Ala Tyr Ser Thr His Arg Gly
        100                 105                 110

Phe Trp Val Gly Val Arg Phe Ser Pro Gly Ile Ala Pro Ala Leu Leu
    115                 120                 125

Gly Ile Pro Ala His Glu Leu Arg Asp Gln Arg Val Asp Leu Ala Asp
130                 135                 140

Leu Trp Pro Gly Ala Gly Thr Arg Leu Thr Glu Arg Val Asp Gly
145                 150                 155                 160

Gly Gly Arg Thr Arg Pro Pro Ser Arg Ile Trp His Cys Gly Val
            165                 170                 175

Ala Ala Asp Ala Glu Pro Val Asp Pro Leu Leu Arg Ala Val Val Val
        180                 185                 190

Ser Leu Glu Ala Gly Arg Ser Val Thr Ala Thr Ala Asp Ser Val Gly
    195                 200                 205

Leu Gly Ala Arg Gln Leu His Arg Arg Ser Leu Ala Ala Phe Gly Tyr
210                 215                 220

Gly Pro Lys Thr Leu Ala Arg Val Leu Arg Met Gln Arg Ala Leu Arg
225                 230                 235                 240

Leu Ala Arg Ala Gly Val Pro Phe Ala Glu Thr Ala Thr Leu Ala Gly
            245                 250                 255

-continued

```
Phe Ala Asp Gln Ala His Leu Ala Arg Asp Val Arg Glu Met Ala Gly
            260                 265                 270
Ser Ser Leu Ser Glu Leu Val Glu Arg
            275             280
```

GENES ENCODING RESISTANCE TO DNA ALKYLATING AGENTS

This application is a continued provision of a national stage filing of international application PCT/US94/11279, filed Oct. 6, 1994, which is a continuation-in-part application of U.S. application Ser. No. 08/133,963, filed Oct. 7, 1993, now abandoned.

BACKGROUND OF THE INVENTION

Agents that act to damage DNA by alkylation, DNA-DNA crosslinking, DNA-protein crosslinking, and/or DNA cleavage have been used as potent chemotherapeutic agents. Some of these agents are reductively activated by electron transfer to a moiety such as semi-quinone. Agents which are thought to be reductively activated include the naturally occurring and synthetic mitomycins and the enediynes such as neocarzinostatin. Kasai et al., *SynLett*, 10:788 (1992) (mitomycins); and Nicolaou et al., *Angewandte Chemie*, 30:1387 (1991) (enediynes). Cellular resistance to these types of chemotherapeutic agents develop, especially in tumor cells. The mechanism of resistance of tumor cells and the organisms that produce the agents are not known.

Mitomycins are agents that are reductively activated and catalyze DNA alkylation and DNA-DNA crosslinks. Mitomycins are antitumor antibiotics produced by *Streptomyces lavendulae* and other Streptomyces species. Several mitomycins have been characterized including the naturally occurring mitomycin A, mitomycin B, mitomycin C (MMC), porfiromycin, and mitiromycin. The structural properties and biological activity of mitomycins have motivated a large number of studies to determine cellular target sites and mechanism of action. Complete structural characterization of MMC has been followed by studies showing the basis of its remarkable activity against mammalian tumor cells. Iyer et al., *Science*, 145:55 (1964); Schwartz et al., *Science*, 142:1181 (1963). The molecule has three important functional groups, which include a quinone ring system, carbamate moiety, and a highly strained aziridine group that contribute together to determine MMC target site specificity and ability to alkylate DNA. Significantly, the precise regions in DNA that undergo mono- and bifunctional alkylation by MMC, leading to inhibition of replication and subsequent cell death have also been determined. Cera et al., *Biochemistry*, 28:3908 (1989); Kumar et al., *Biochemistry*, 32:1364 (1993); Teng et al., *Biochemistry*, 28:3901 (1989); and Tomasz et al., *Science*, 235:1204 (1987).

Mitomycins are DNA bioreductive alkylating agents which present a difficult and unique challenge for cellular resistance in producing microorganisms. Beijnen et al., *J. Pharm. Biochem. Anal.*, 4:275 (1986); Kumar et al., supra. Evidence strongly supports the idea that the first step in biological activation of mitomycins occurs by catalytic electron transfer to the benza-quinone species to form a semi-quinone radical shared by mitomycins. Hoey et al., *Biochemistry*, 27:2608 (1988). In this form, the molecule would fit into the minor groove of DNA and undergo further reduction to the hydroquinone. Beijnen et al., supra.; Hoey et al., supra. The second electron transfer is presumed to occur with rapid kinetics, and is followed by DNA alkylation through activation of the two electrophilic centers in the mitomycin hydroquinone species. With this unique biological activity, it is clear that the two most common resistance mechanisms in bacteria, protection of the target site (methylation of ribosomal RNA) and modification of the antibiotic (phosphorylation or acetylation), are unlikely to be applicable to mitomycin. Davies, *FEMS Microbiology Reviews*, 39:363 (1986); Witt et al., *Appl. Microbiol.*, 13:361 (1990). Specifically, it would be impractical for the cellular DNA to be protected (e.g. modified by extensive methylation) because the GC content in *S. lavendulae* is ~70%, and the mitomycin target site for mitomycin C (MMC) has been shown specifically to be CpG residues. Teng et al., supra. Likewise, protection by drug modification through phosphorylation or acetylation would not prevent electron transfer or the activation of electrophilic centers in the molecule.

Although there is a wealth of knowledge about the structure, mode of action and mechanism of activation of mitomycin C, no studies have been conducted to determine the molecular basis for resistance in the producing organisms such as *S. lavendulae*. Indeed, resistance mechanisms are unknown for the entire class of bioreductive alkylating and cleaving agents like MMC, and other potent anti-tumor compounds that alkylate or cleave DNA following reductive activation. Beijnen et al., supra.; Hoey et al., supra.; and Woo et al., *J. Amer. Chem. Soc.*, 115:1199 (1993). Understanding resistance to these molecules in these producing microorganisms may provide insight into the problem of multidrug resistance (MDR) of cancer cells, and its effect on long term therapeutic efficacy of antineoplastic agents. Moscow et al., *Multidrug Resistance. Cancer Chemotherapy and Biological Response Modifiers Annual* 11, Elsevier Science Publishers B.V. (1990). Identification of additional mechanisms that contribute to broad spectrum drug resistance of tumors in mammalian systems may allow the development of strategies to identify and effectively control this complex problem.

Thus, there is a need to study cellular resistance to compounds that bioreductively alkylate or cleave DNA. There is a need to identify agents that inhibit resistance to compounds that bioreductively alkylate or cleave DNA. There is also a need to identify and modify DNA gene sequences that are responsible for drug resistance mechanisms in microorganisms and in animal and human tumor cells.

SUMMARY OF THE INVENTION

The invention provides for an expression cassette and vectors including the expression cassette. The expression cassette comprises a DNA sequence that provides resistance to a cell to a DNA bioreductive alkylating or cleaving agent operably linked to a promoter functional in the cell. The preferred DNA bioreductive alkylating or cleaving agent is a mitomycin. Preferred DNA sequences are those that substantially correspond to the mcr and mrd loci of *S. lavendulae* B619. The promoter is preferably functional in Streptomyces and provides for a sufficient level of gene expression so that resistance of the cell to the DNA bioreductive alkylating or cleaving agent can be detected.

Once a DNA sequence that provides resistance to a cell to a DNA bioreductive alkylating or cleaving agent is identified, it can be used to generate DNA probes. A DNA probe has sufficient complementarity to all or a portion of a known DNA or RNA sequence that provides resistance to the agent so that it can hybridize to the DNA or RNA sequence, preferably under low stringency conditions. Portions of a DNA or RNA sequence preferably are restriction endonuclease fragments of the mcr or mrd DNA sequence. The preferred probes are complementary to the 6.7 kb BclI fragment of pDHS3000 encoding mcr and the 4.2 kb BclI fragment of pDHS3001 encoding mrd.

Two loci have been identified that provide mitomycin resistance to mitomycin sensitive host cells. One locus found on a 6.2 kb BclI fragment from *S. lavendulae* has now been designated mcr and is the same as the locus designated mcrA in U.S. application Ser. No. 08/133,963. On the mcr locus, three open reading frames were identified and are now designated 1) mcrA which is the same as the DNA sequence identified as mcrA1; 2) mcrB which is the same as the DNA sequence identified as mcrA2; and 3) mcrORF3 which is the same as the DNA sequence previously identified as mcrAORF3 in U.S. application Ser. No. 08/133,963. The other locus is found on a 4.2 kb BclI fragment on plasmid pDHS3001 and is now referred to as mrd and is the same as the locus previously identified as mcrB in U.S. application Ser. No. 08/133,963. The identifiers of the gene loci and DNA sequences in this application have been changed from the parent application Ser. No. 08/133,963 as described above. Subject matter from the parent application that referred to the previous identifiers has been modified to the new identifiers, but the gene loci and DNA sequences remain the same as those disclosed in the parent application Ser. No. 08/133,963.

The invention also provides for polypeptides and antibodies specific for the polypeptides. A polypeptide can be encoded by a DNA sequence that provides resistance to a cell to a DNA bioreductive alkylating or cleaving agent such as the mcr DNA sequence. The preferred polypeptide is the MCRA polypeptide which is about a 56,000 dalton polypeptide encoded by mcrA.

The invention also provides transformed cells. Transformed cells comprise an expression cassette comprising a DNA sequence that substantially corresponds to a DNA sequence that provides resistance to the cell to a DNA bioreductive alkylating or cleaving agent operably linked to a promoter. The preferred cell is a cell sensitive to the DNA bioreductive alkylating or cleaving agent such as *Streptomyces lividans*. The preferred DNA sequence substantially corresponds to the DNA sequence of the mcrA and mcrB genes. The expression cassette preferably is expressed in an amount sufficient to confer resistance to the cell to the agent.

The invention also provides methods for identifying agents that inhibit the resistance of the cell to the DNA bioreductive alkylating or cleaving agent. One method involves using transformed cells. Transformed cells resistant to the agent comprise an expression cassette as described herein. The transformed cells are incubated with an effective amount of an agent suspected to inhibit resistance of the cell to the DNA bioreductive alkylating or cleaving agent and an effective amount of the DNA bioreductive alkylating or cleaving agent. After incubation for a suitable amount of time, it can be determined if the suspected agent inhibited the resistance of the cell to the DNA bioreductive alkylating or cleaving agent.

In an alternative version, an inhibitory agent can be identified by its ability to inhibit the function of a polypeptide encoded by the DNA sequence. A substantially pure polypeptide such as MCRA is incubated with a DNA sample and the DNA bioreductive alkylating or cleaving agent and the inhibitory agent. After incubation, it can be determined whether the inhibitory agent inhibited the function of MCRA polypeptide by measuring the binding of the DNA bioreductive alkylating or cleaving agent to the DNA sample or by determining whether DNA alkylation has occurred. If the suspected inhibitory agent inhibits the function of MCRA, binding and/or activity of the DNA bioreductive alkylating or cleaving agent is increased in the presence of the suspected inhibitory agent, preferably 2 to 20-fold.

The invention also provides a method for identifying sequences homologous to the mcr or mrd sequences in other cell types and/or organisms. Preferably, the cells are multidrug resistant or mitomycin C-resistant tumor cells. The method involves generating a DNA library and amplifying selected sequences in the library using polymerase chain reaction. Amplification of selected sequences is accomplished by selecting oligonucleotide primers that are complementary to a portion of the mcr or mrd loci. Once formed, the amplified products are isolated and screened for homology to mcr or mrd by hybridization to a DNA probe. Sequences that hybridize can be mapped using restriction enzymes and sequenced using standard methods.

BRIEF DESCRIPTION OF THE FIGURES

FIG. 3. Alignment of the mcrA (PI) [SEQ ID NO: 5] and 6-hydroxy-D-nicotine oxidase [SEQ ID NO: 4] deduced amino acid sequences. Identical amino acids are shaded. The histidine responsible for attachment of FAD to 6-hydroxy-D-nicotine oxidase and conserved in the deduced mcrA amino acid sequence is marked by a dot (·).

FIG. 11. DNA sequence of mrd locus derived from 4.2 kb BclI fragment from plasmid pDHS3001 [SEQ ID NO: 11].

DETAILED DESCRIPTION OF THE INVENTION

The invention provides for an expression cassette including a DNA sequence that provides resistance to a cell to a DNA bioreductive alkylating or cleaving agent as well as a polypeptide encoded by the DNA sequence. The invention also provides transformed cell lines and methods for identifying agents that inhibit the resistance of a cell to a DNA bioreductive alkylating or cleaving agents. DNA probes of the invention are substantially complementary to all or a portion of a DNA sequence that provides resistance to a cell to a DNA bioreductive alkylating or cleaving agent and are useful in a method for detecting homologous DNA sequences in other organisms.

DNA sequences providing for resistance to a cell to a DNA bioreductive alkylating or cleaving agent have been identified. A DNA sequence that provides resistance to a DNA bioreductive alkylating or cleaving agent can encode a polypeptide that imparts resistance to cells from these agents and/or protects DNA from these agents.

A bioreductive DNA alkylating or cleaving agent is an agent that has a moiety that is reductively activated by electron transfer and can catalyze cleavage or alkylation of DNA. Agents that have a moiety such as a benza-quinone which is reduced to a semiquinone and/or hydroquinone species to become bioreductively activated include mitomycins. While not meant to be a limitation of the invention, it is believed that once the DNA bioreductive alkylating or cleaving agent is reductively activated it binds to DNA and can catalyze one or more of the following reactions: DNA alkylation, DNA-DNA crosslinking, DNA-protein crosslinking, or DNA cleavage. It is further believed that one way that a polypeptide imparts resistance to cells from these agents is by binding to and deactivating the reduced active form of the agent. It is believed that deactivation occurs by oxidation.

Figure 1:
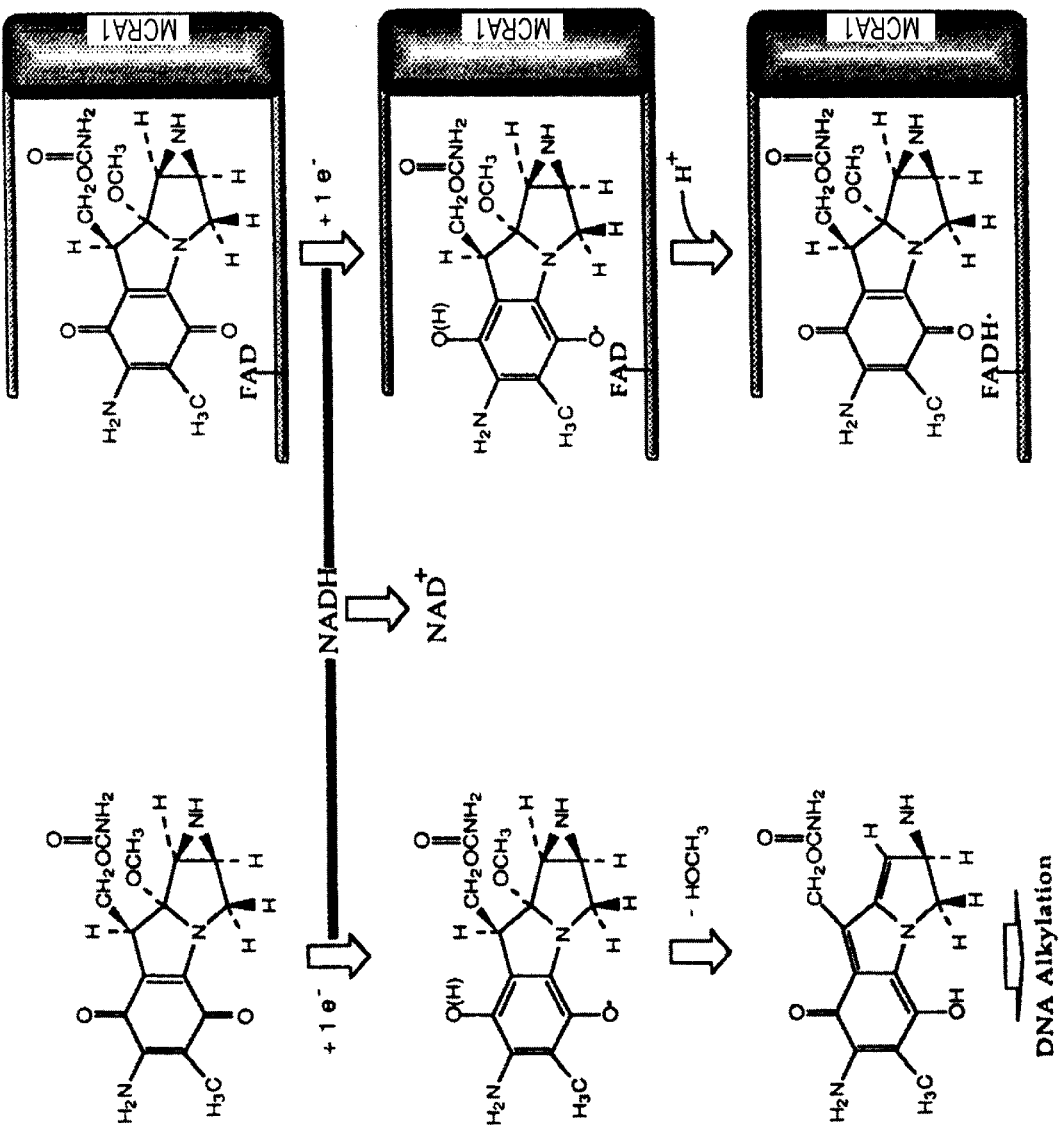
FIG. 1. Model of the mechanism whereby the MCRA polypeptide confers resistance against MMC. The left hand side of the figure demonstrates an activation cascade for MMC while the right side shows how MCRA can prevent MMC activation. After reduction of the quinone of MMC to the semi-quinone radical, an FAD bound to MCRA would remove a single electron to form FADH·. FADH· could again be reduced completely to $FADH_2$ or undergo reoxidation to FAD.

A specific example of one cellular resistance mechanism to DNA bioreductive alkylating or cleaving agents is shown in FIG. 1. The DNA bioreductive alkylating or cleaving agent shown in FIG. 1 is mitomycin C and a polypeptide that imparts resistance to mitomycin C (MMC) is designated MCRA. While not meant to be construed as a limitation of the invention, it is believed that the MCRA polypeptide includes a covalently bound cofactor, such as flavin adenine dinucleotide (FAD), that mediates the oxidation of MMC in the event that it undergoes sequential reduction through the semi-quinone radical. One electron reduction of MMC can result in immediate oxidation by MCRA bound FAD to the FADH· species. The FADH· species would be available to accommodate a second electron transfer from MMC to result in a non-reduced form of MMC that cannot bind to or catalyze alkylation or crosslinking of DNA.

Identification of DNA sequences that provide resistance to a cell to a DNA bioreductive alkylating or cleaving agent provides for polypeptides, DNA probes, and transformed cell lines. These DNA sequences can be used in methods to identify agents that inhibit resistance of cells to a DNA bioreductive alkylating or cleaving agent as well as to identify homologous DNA sequences that provide for resistance in other cells, such as tumor cells.

The invention also provides for antibodies to MCRA and methods for detecting expression of MCRA or related polypeptides in cells resistant to DNA bioreductive alkylating and/or cleaving agents.

A. Bioreductive Alkylating or Cleaving Agents

Agents that act to damage DNA by alkylation, DNA-DNA crosslinking, DNA-protein crosslinking, and/or DNA cleavage can be potent cancer chemotherapeutic agents. These agents are characterized by the ability to bind to and alter DNA. A DNA cleaving agent is one that binds DNA and creates single or double-stranded breaks. A DNA alkylating agent is an agent that binds to DNA and forms covalent bonds to the DNA molecule. DNA alkylation includes the formation of DNA-DNA and DNA-protein crosslinks.

Within this class of compounds are compounds referred to as DNA bioreductive alkylating or cleaving agents. A DNA bioreductive alkylating or cleaving agent is a compound that is reductively activated. Reductive activation can occur by electron transfer to a moiety in the agent such as a benza-quinone. Molecules containing moieties such as anthraquinone, aminoquinone, or enediyne can become reductively activated and then catalyze damage to DNA. Compounds that can be reductively activated preferably include the following structural component:

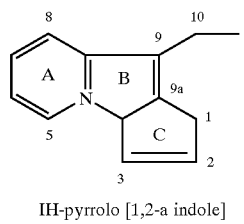

IH-pyrrolo [1,2-a indole]

Compounds that include both an aromatic ring as shown above and optionally include an aziridine nitrogen group at carbons 1 and 2 are also perferred DNA bioreductive alkylating or cleaving agents. While not meant to be a limitation of the invention, it is believed that once the agent is activated, it can bind to DNA and catalyze DNA alkylation, crosslinking or cleavage. An aromatic group can function as a site for reductive activation and an aziridine group is involved in creating DNA damage.

The DNA bioreductive alkylating and/or cleaving agents are also preferably those compounds that can induce expression of a DNA sequence that codes for resistance to the agent. A DNA bioreductive alkylating or cleaving agent can also be a compound that does not induce expression of a DNA sequence that encodes resistance but that is inactivated by a polypeptide encoded by a DNA sequence that provide resistance to a cell to the agent. While not meant to limit the invention, it is believed that inactivation of the DNA bioreductive alkylating or cleaving agent by a polypeptide occurs by binding of the agent to the polypeptide followed by deactivation by oxidation of the DNA bioreductive alkylating or cleaving agent.

Specific example of bioreductive DNA alkylating or cleavage agents include the mitomycins and related compounds. The structure of mitomycins is as follows:

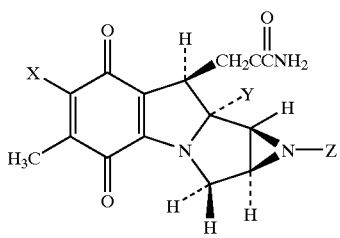

Mitomycins contain a benza-quinone moiety that can be reduced by electron transfer to form activated mitomycins. Activated mitomycins bind to DNA and catalyze DNA-DNA and DNA-protein crosslinks and DNA alkylation.

Mitomycins can be naturally occurring compounds produced by Streptomyces species and include mitomycin A, mitomycin B, mitomycin C, porfiromycin, and sit mitiromycin. Other mitomycins include mitomycins E, G. I, J, L, M, K, mitiromycin, albomitomycin A, A isomitomycin A, KW 2149, KW-2149 metabolites such as M-16 and M-18. Naturally occurring mitomycins can be isolated from growth media of Streptomyces species by known methods, as described Herr et al., *Antimicrobial Agents Annual*, at page 23, Plenum Press, NY (1960). Other Mitomycin derivatives have also been chemically synthesized as described Kasai et al. in *SynLett*, 10:777 (1992). Mitomycin analogs can also be obtained by directed biosynthesis as described by Claridge et al., *J. Antibiotics*, 39:437 (1986).

Another specific example of DNA bioreductive alkylating or cleaving agents are substituted dihydrobenzoxazines such as FR900482, as described in *J. Am. Chem. Soc.*, 109:4106 (1987). The structure of FR900482 is as follows:

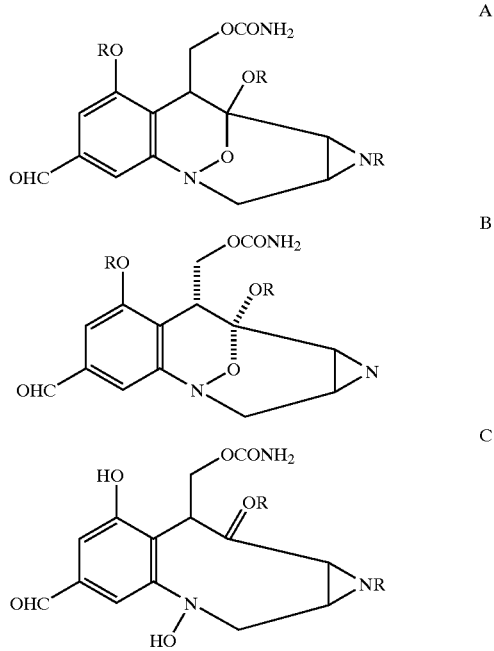

These compounds are known to catalyze DNA-DNA and DNA-protein crosslinks similar to mitomycin C. Masuda et al., *Cancer Research*, 48:5172, cited supra. The agent FR900482 can be obtained from growth medium of *Streptomyces sandaensis* 6897, as described by Kiyoto et al., *J. Antibiotics*, 40:594 (1987).

DNA bioreductive alkylating or cleaving agents can be produced by Streptomyces species. Because of their toxic and damaging effects on DNA, the producing microorganisms have resistance mechanisms that protect their DNA from these agents. DNA sequences that impart resistance to DNA bioreductive alkylating or cleaving agents are isolated as described herein.

B. Expression Cassettes Including a DNA Sequence that Provides Resistance to a Cell to a DNA Bioreductive Alkylating or Cleaving Agent The invention provides an expression cassette comprising a DNA sequence that provides resistance to a cell to a DNA bioreductive alkylating or cleaving agent operably linked to a promoter functional in the cell. The DNA sequence can contain one or more genes and/or portions of the genes or gene locus. The DNA sequence can encode a single polypeptide or more than one polypeptide. The DNA sequence can provide resistance to a DNA bioreductive alkylating or cleaving agent by encoding a polypeptide that provides resistance to the cell or protects DNA from the action of the DNA bioreductive alkylating or cleaving agent. The promoter is preferably a DNA sequence that provides for a sufficient level of expression of the gene or genes encoded on the DNA sequence in the cell so that resistance of the cell to the DNA bioreductive alkylating or cleavage agent can be detected.

The DNA sequence can encode a gene locus. A "gene locus", as used herein, encodes more than one gene or has more than one open reading frame. A "gene", as used herein, includes the DNA coding sequence and any intron DNA sequences. Untranslated sequences, such as promoters or enhancer sequences or 3' polyA sequences or other untranslated regulatory sequences that provide for gene expression in a cell, are not included in the term "gene" as used herein. A DNA sequence can also include portions of a gene locus or a gene. Portions of a gene or gene locus, as used herein, refer to restriction enzyme fragments of the gene or gene locus.

A cell is resistant to a DNA bioreductive alkylating or cleaving agent if it can grow in the presence of amounts of the agent that typically prevent growth of this type of cell. Growth preferably is about 2 to 1000-fold, and more preferably 2 to 100-fold increased over a sensitive cell. Those amounts can vary depending on the cell and the agent, but can be readily determined using standard dose response methods as described in Masuda et al., cited supra. Preferably the amount of DNA bioreductive alkylating or cleavage agent is in the range of about 1–1000 µg/ml, more preferably about 10–500 µg/ml, and most preferably about 25–100 µg/ml.

Alternatively, a cell is resistant to a DNA bioreductive alkylating or cleavage agent if the DNA from the cell does not develop interstrand DNA-DNA crosslinks or breaks in the DNA in the presence of the agent. DNA-DNA crosslinks can be determined by standard methods, such as the alkaline elution method or DNA renaturation method as described by Masuda et al., cited supra. Single strand DNA breaks in cells incubated in the presence of a DNA bioreductive alkylating or cleaving agent can be determined using a method such as the alkaline elution method described by Masuda et al., cited supra. Cells exhibiting resistance do not develop DNA-DNA crosslinks or breaks to any appreciable extent after exposure to amounts of the agent that cause DNA-DNA crosslinks or breaks in the DNA in sensitive cells. Preferably, resistant cells show a decrease in DNA-DNA crosslinks of about 2 to 20 fold compared to sensitive cells.

A DNA sequence that provides resistance to a DNA bioreductive alkylating or cleaving agent can encode a polypeptide that provides resistance to the cell or protects the DNA from the action of the agent. This polypeptide can act to prevent transport of the agent into the cell or nucleus or can act to inactivate the agent. While not in any way meant to be a limitation of the invention, a DNA sequence can also provide resistance to a cell by specifying a structural alteration of the agent, or modifying cellular target sites. Preferably the polypeptide inactivates the bioreductive DNA alkylating or cleaving agent by oxidation.

A DNA sequence that imparts resistance to a cell to a DNA bioreductive alkylating or cleaving agent can include one gene or more than one gene. Preferably, resistance is imparted by the mcrA and mcrB genes on the mcr locus providing for the expression of MCRA.

A DNA sequence that confers resistance to a cell to DNA bioreductive alkylating or cleavage agents can be isolated from the genome of the cell as follows. Preferably, the cell is a microorganism that produces a DNA bioreductive alkylating or cleaving agent. A DNA library can be generated from the cell using standard methods as described in Sambrook et al., cited supra. One such method includes digesting the total chromosomal DNA with the restriction enzyme and ligating the fragments into a vector, such as a plasmid. The vectors are then introduced into a host cell. The host cell is preferably a cell that does not grow in the presence of the DNA bioreductive alkylating or cleaving agent (i.e., is sensitive). Transformed cells are then selected for the ability to grow in the presence of different amounts of the DNA bioreductive alkylating or cleaving agent. An additional or alternative screening method that can be utilized optionally is to determine whether the transformed cells that can grow in the presence of the DNA bioreductive alkylating or cleaving agent develop DNA-DNA crosslinks or breaks as described herein.

Vectors from the transformed cells resistant to the agent are isolated and the DNA sequences conferring resistance are identified. The ability of the DNA sequences to impart resistance to the cell is confirmed by subcloning of the sequence and transfer of the sequence into a sensitive host cell. Analysis of the sequence of DNA is conducted by standard methods. The DNA sequence and/or the predicted amino acid sequence can then be compared to other known DNA sequences using a computer databank, such as the GenBank, and homologous sequences from other organisms identified.

Figure 6:
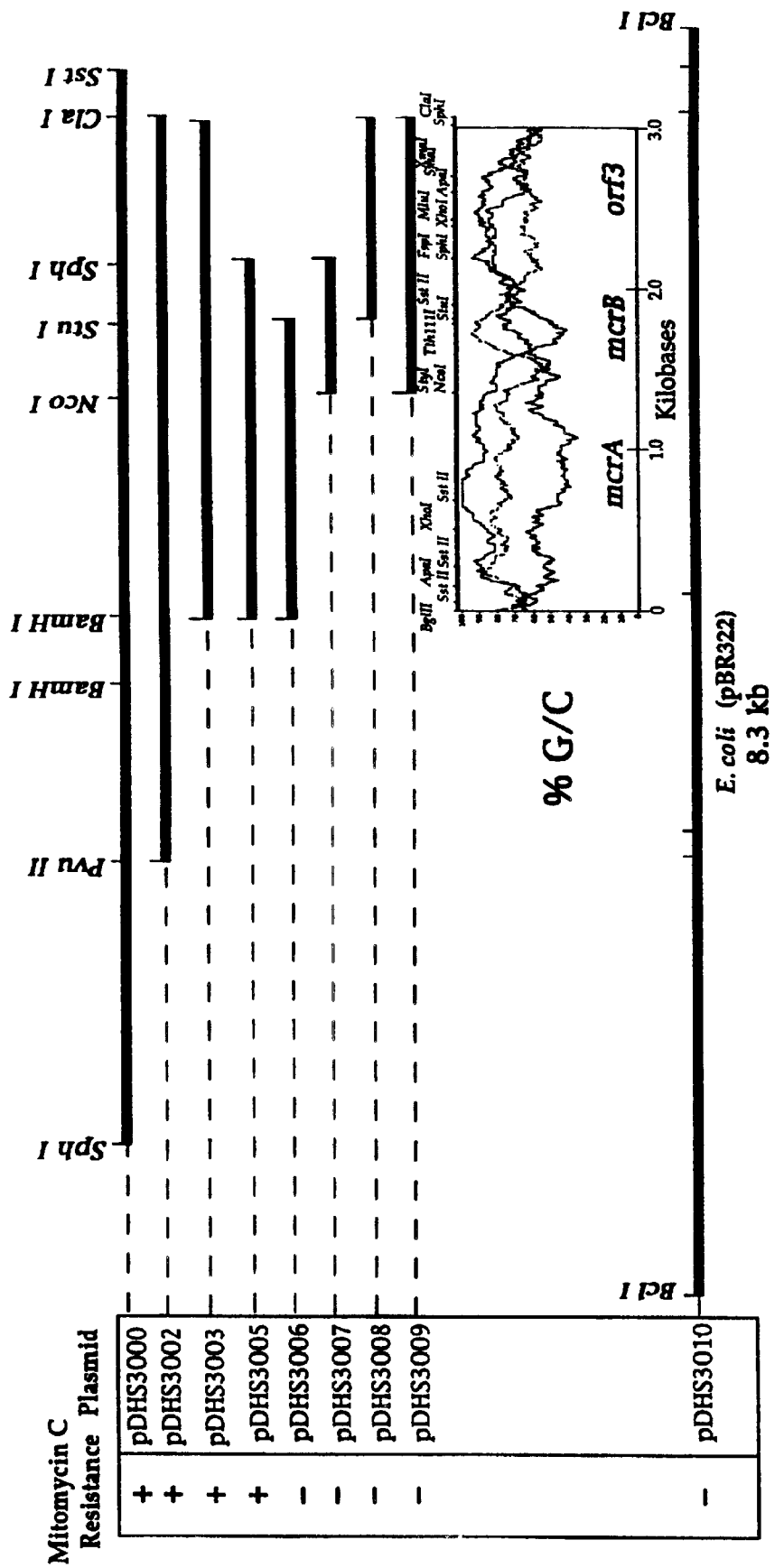
FIG. 6. Frame analysis of mcr, and restriction enzyme map of pDHS3000 illustrating subcloning performed to determine the DNA sequence necessary to confer MMC resistance to *S. lividans*. A (+) in the mitomycin C resistance column indicates that the vector to the right was able to confer MMC resistance, whilst a (−) indicates no resistance. Shaded areas represent DNA cloned from *S. lavendulae* B619, whereas dark areas represent vector DNA.
Figure 12:
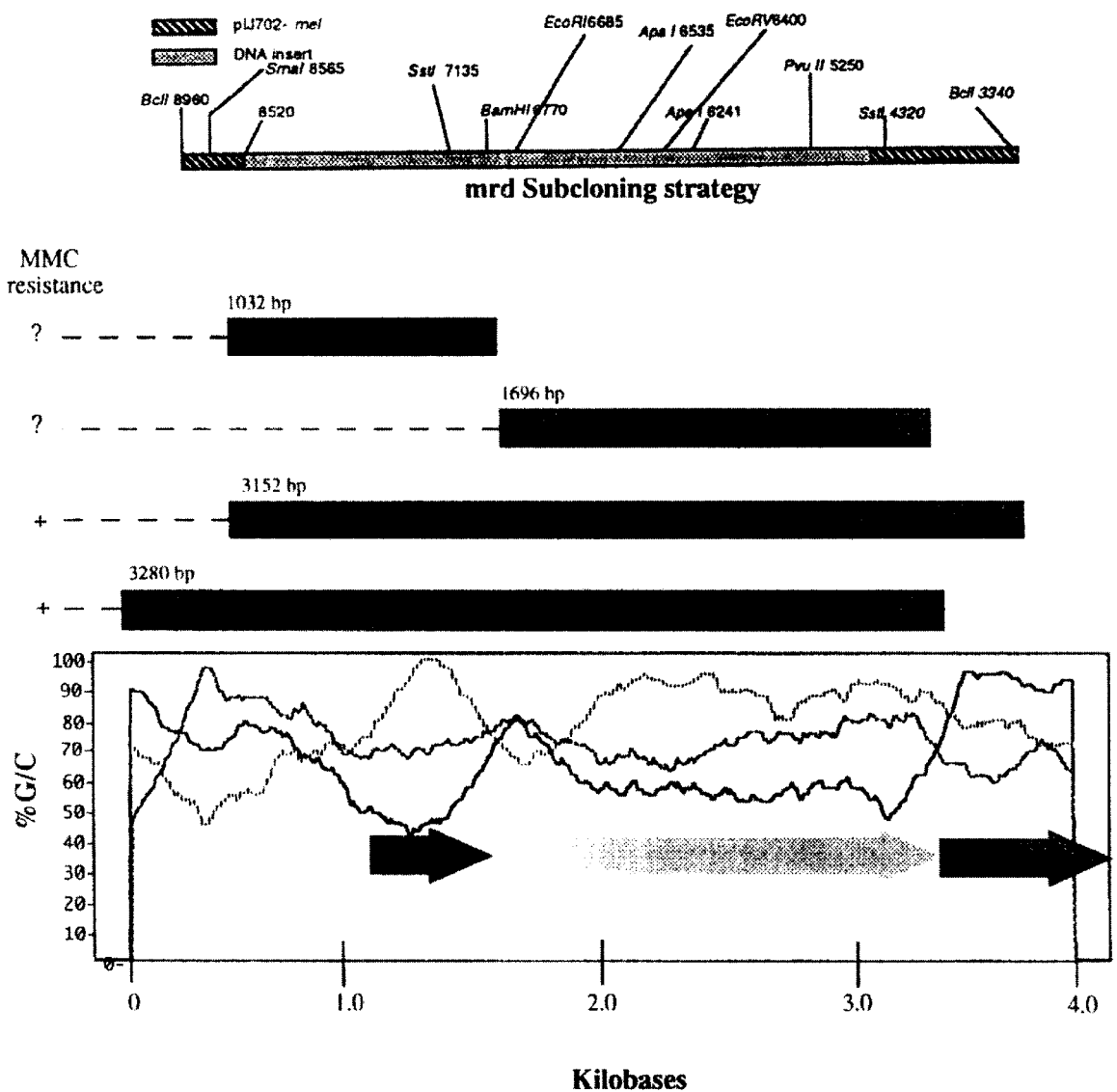
FIG. 12. Genetic map of mrd resistance locus from *Streptomyces lavendulae*. Shaded regions are defined as indicated. A putative MMC hydroxylase is located at the 3' end of mrd locus. Map of subclones of mrd locus and the ability of the subclones to confer resistance to MMC at 25 µg/ml to *S. lividans*.

Portions of a gene or gene locus can be obtained by digesting a DNA sequence encoding the gene or gene locus with one or more restriction enzymes such as shown in FIG. 6 and FIG. 12. The restriction enzyme fragments of the DNA sequence are those fragments of the DNA sequence that can confer resistance to a DNA bioreductive alkylating or cleaving agent to a cell. The fragments generated are ligated into a vector and the vector is introduced into a suitable sensitive host cell. The transformed cells are selected for the growth in the presence of the DNA bioreductive alkylating or cleaving agent. Fragments of the gene or gene locus are identified by standard methods including restriction endonuclease mapping.

Methods of transformation and suitable host cells are known to those of skill in the art. Methods of transformation include calcium chloride or phosphate precipitation, electroporation, polybrene, liposomes, and protoplast fusion with polyethylene glycol and the like. Suitable host cells are those that exhibit sensitivity (i.e., do not grow in the presence of the DNA bioreductive alkylating or cleaving agent). Specific examples of suitable host cells are sensitive Streptomyces species such as *Streptomyces lividans*, *Streptomyces coelicoler*, *Streptomyces parvulus*, and *Streptomyces griseus*.

Figure 2A:
FIG. 2. Nucleotide sequence and deduced amino acid sequence of mcrA [SEQ ID NO: 1], mcrB [SEQ ID NO: 2], and mcrORF3 [SEQ ID NO: 3] genes of *S. lavendulae* B619. Shaded circles with arrows represent the translational start point (TSP) for promoters P1 and P2 as determined by primer extension. The thin arrowed line labeled PE primer indicates the location of the oligonucleotides used for TSP determination. Potential –35 and –10 regions are labeled for both TSPs. The dark line labeled RBS indicates a potential RBS for a polypeptide translated from the shorter transcript originating from P2. The shaded valine proximal to the RBS indicates a potential start codon for the shortened mcrA polypeptide. Facing arrows reveal two divergent repeats, which may have roles in transcription termination, with ΔG values lower than –45 kcal/mol.

Preferred examples of DNA sequences that provide resistance to a DNA bioreductive alkylating or cleaving agent include DNA sequences that provide resistance to mitomycins such as the mcr gene locus and the mrd gene locus from *S. lavendulae* B619. These two gene loci provide for resistance of *S. lividans* to mitomycin C. The mcr locus confers resistance to >100 µg/ml mitomycin C, and the mrd locus confers resistance to about 25 µg/ml. The mcr locus includes three different coding sequences designated mcrA, mcrB, and mcrORF3 and has the DNA sequence as shown in FIG. 2. The mcr locus is contained on the 6.7 kb BclI fragment of pDHS3000. The mcrA and mcrB sequences are found on the 2.2 kb BglII-SphI fragment of pDHS3005.

The mrd locus is contained on the 4.2 kb BclI fragment of pDHS3001. The mrd locus is contained on the 4.2 kb BclI fragment of pDHS3001 and has the sequence shown in FIG. 11.

Preferred examples of portions of the DNA sequence are shown in FIG. 12. Subclones of the mrd locus are generated as follows. A 3280 bp subclone of pDHS3001 is generated with AflIII/AscI. A 3152 bp subclone of pDHS3001 was generated with NotI. These subclones confer resistance to a cell to 25 ug/ml mitomycin C.

Preferred examples of portions of DNA sequences include those shown in FIG. 6. Portions of the mcr locus were generated by digesting a 6.7 kilobase BclI fragment encoding the mcr locus with SphI, PuvII, BamHI, BglII, PstI, FspI, NcoI, StuI, and ClaI. The fragments are subcloned into plasmids, as shown in Table I. The subclones are tested for the ability to confer resistance to mitomycin C, as described herein. The minimum DNA sequence of the mcr locus identified that provides resistance to mitomycin C corresponds to the DNA sequence of the 2.2 kilobase BglII-SphI subclone of the plasmid designated pDHS3005.

DNA sequences can also substantially correspond to DNA sequences encoding the mcr gene locus, mcrA, mcrB, and mcrORF3, respectively. A DNA sequence that substantially corresponds is a DNA sequence that shares sufficient continuous DNA sequence identity to a DNA sequence encoding the mcr locus, mcrA gene, mcrB gene, or mcrORF3 gene or mrd locus so that the DNA sequence provides resistance to a cell to mitomycins, and can hybridize to a probe derived from mcr or mrd locus. A DNA sequence that substantially corresponds preferably shares about 75–100% DNA sequence identity, and more preferably about 90–100% DNA sequence identity. Once the sequence is known as shown in FIGS. 2 and 11, probes can readily be designed and synthesized using methods known two those of skill in the art. The sequence preferably hybridizes to a probe derived from the mcr or mrd loci under conditions of high stringency. One example of a DNA sequence that substantially corresponds to the DNA sequence of mcrA is a DNA that includes a CAT codon for His[64] rather than CAC. Changes in the nucleotide sequence that do not result in a change in the amino acids encoded by the DNA sequence are sequences that are likely to also provide resistance to a cell to mitomycins.

It would be understood by those of skill in the art that due to the degeneracy of the genetic code, there is a defined set of DNA sequences that can encode polypeptides encoded by mcr and mrd loci such as MCRA. These DNA sequences can vary in the DNA sequence due to changes in a codon for a particular amino acid, but still encode a polypeptide with an amino acid sequence such as that of MCRA. These DNA sequences are also those that impart resistance to a cell to a DNA bioreductive alkylating and/or cleaving agent.

Promoters

A DNA sequence that provides for resistance to a DNA bioreductive alkylating or cleaving agent to a cell functional in the cell in the expression cassette is operably linked to a promoter. A promoter is an untranslated DNA sequence that provides for expression of the DNA sequence and is preferably located immediately upstream from the DNA sequence. Preferably, the promoter provides for a level of expression of the DNA sequence in an amount effective to render the cell resistant to the DNA bioreductive alkylating or cleaving agent. The promoter can be a native promoter that is associated with and provides for expression of the DNA sequence in the source organism. The promoter can be a constitutive or inducible promoter. The promoter can also be a heterologous promoter obtained from a different gene and/or a different organism. The promoter is functional in the host cell carrying the expression cassette. The promoter can be derived from prokaryotic, viral, or eukaryotic sources.

Suitable examples of prokaryotic promoters include the $P_{Lac}$ promoter, the $P_{tac}$ promoter, mel promoter on pIJ702, tipA of *Streptomyces lividans* and ermE of *Saccharopolyspora erythrea*. Suitable examples of viral promoters include the SV40 early promoter, the Herpes Simplex thymidine kinase promoter, the Rous sarcoma LTR promoter, the bacteriophage T7 promoter, the bacteriophage $\lambda P_L$ promoter, and the like. Suitable examples of eukaryotic promoters include yeast promoters such as ADHI promoter, the TPI promoter, the GALI promoter, and the metalothionein promoter. The preferred promoters for an expression cassette are the $P_{tac}$ promoter and the SV40 early promoter. The especially preferred promoter is a promoter inducible by the DNA bioreductive alkylating or cleaving agent. Promoters are commercially available in vectors or can be obtained using known methods as described in Sambrook et al., cited supra., and Nielsen et al., *Appl. Microbiol. Biotech.*, 33:307 (1990).

The promoter sequence is combined with a DNA sequence that provides resistance to a DNA bioreductive alkylating or cleaving agent by standard methods to form an expression cassette. One such method involves digesting a plasmid containing the DNA sequence and a plasmid containing the promoter with the same restriction enzymes, and then ligating the fragments into a third vector. The third vector is then transformed into host cells and the host cells are selected for expression of the DNA sequence by selecting cells resistant to the DNA bioreductive alkylating or cleaving agent. Other methods utilizing subcloning of the DNA sequence into established expression vectors can be conducted as described by Sambrook et al., cited supra, for expression of cloned DNA sequences in mammalian or prokaryotic cells.

Once formed, an expression cassette can also be subcloned into a vector so that efficient transmission into sensitive host cells can be achieved. Vectors can include viral or plasmid vectors. Preferably, the vector is a known expression vector such as the SV40 vectors, the pSMG, the pSVT7, the pMT2, the p205, the pHeBo, the pBV-1MTHA, the PAS1, the pET-3A, and the pKK177-3 as described by Sambrook et al., at pages 16.17 to 16.27. The preferred expression vector is a high copy number plasmid from Streptomyces species such as the pIJ702. Many of the expression vectors are commercially available. pIJ702 can be obtained from the John Innes Institute, Norwich, England.

An expression cassette can also comprise a selectable marker gene. Selectable marker genes are known to those of skill in the art and are present in the commercially available expression vectors. Specific examples of selectable marker genes include thymidine kinase, dihydrofolate reductase, aminoglycoside phosphotransferase, hygromycin B phosphotransferase, adenosine deaminase, arginine synthetase, and antibiotic resistance genes.

A preferred plasmid comprising an expression cassette in accordance with the invention is the plasmid pDHS3000 with a 6.7 kb BclI DNA sequence from S. lavendulae B619 containing the mcr locus. This plasmid has been designated 1326/pDHS3000 and deposited in Streptomyces lividans with the American Type Culture Collection (10801 University Blvd., Manassas, Va. 20110-2209) and given Accession No. 69448. Another preferred plasmid is the pDHS3001 with a 4.2 kb BclI DNA sequence from S. lavendulae B619 that contains the mrd locus. This plasmid has been designated 1326/pDHS3001 and deposited in Streptomyces lividans with the American Type Culture Collection (10801 University Blvd., Manassas, Va. 20110-2209) and given Accession No. 69449.

Once an expression cassette is formed, it can be used to form transformed cells. The transformed cells can provide polypeptides encoded by the DNA sequence and that provide resistance to DNA bioreductive alkylating or cleaving agents. The transformed cells are also useful in methods for identifying agents that inhibit the resistance of cells to the DNA bioreductive alkylating or cleaving agents.

C. DNA Probes

Once a DNA sequence that provides resistance to a DNA bioreductive alkylating or cleaving agent is identified, the sequence can be used to develop DNA probes. DNA probes can be useful in a method for identifying homologous DNA sequences that provide resistance to a DNA bioreductive alkylating or cleaving agent in other cells such as drug-resistant tumor cells.

A DNA probe in accordance with the invention comprises a DNA sequence that has sufficient DNA sequence complementarity to all or a portion of a known DNA or RNA sequence that provides for resistance to a DNA bioreductive alkylating or cleaving agent so that the probe can detect the DNA or RNA sequence by hybridization under low stringency conditions. The probe preferably hybridizes to all or a portion of mcr or mrd locus under high stringency conditions. The DNA sequence can be as small as about 17 nucleotides and can be single or double stranded. Preferably, the DNA probe has a size of about 17–2500 nucleotides and more preferably about 50–220 nucleotides.

A preferred DNA probe includes a sequence complementary to nucleotides 310–330 of the mcrA sequence. This nucleotide sequence includes the codon for the histidine residue (His$^{64}$) believed to be important for binding of the FAD cofactor. Other preferred probes include DNA sequences complementary to the DNA sequence found at nucleotides 142 to 166 for amino acids 171 to 177, and nucleotides 646 to 663 for amino acids 429 to 436 of the mcrA gene. As shown in FIG. 3, these regions share amino acid homology with the 6-hydroxy-D-nicotine oxidase. While not in any way meant to limit the invention, it is believed that the polypeptides that provide resistance to mitomycins and other DNA bioreductive alkylating or cleaving agents have a similar mechanism of action as 6-hydroxy-D-nicotine oxidase. Region of the DNA sequence that encode amino acids that share homology with the DNA sequence for the 6-hydroxy-D-nicotine oxidase are selected to develop DNA probes.

Figure 5A:
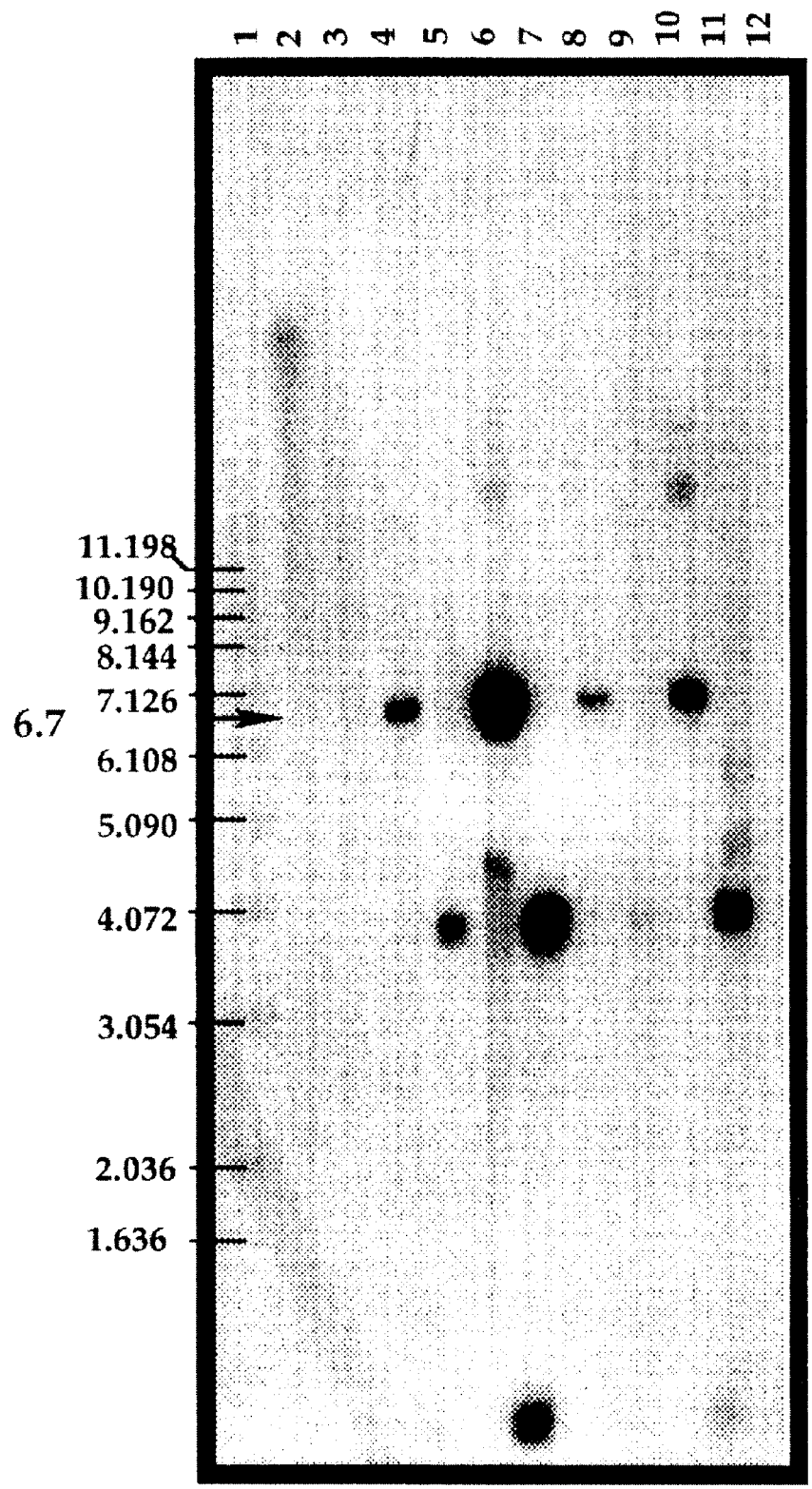
FIG. 5A: *Streptomyces lavendulae* strains which produce MMC, probed with a 6.7 kb BclI insert of pDHS3000 encoding mcr. Lanes: 1, 1 kb ladder; 2, BclI *S. lividans* 1326; 3, BamHI *S. lividans* 1326; 4, BclI *S. lavendulae* B619; 5, BamHI *S. lavendulae* B619; 6, BclI *S. lavendulae* PB1000; 7, BamHI *S. lavendulae* PB1000; 8, BclI *S. lavendulae* NRRL 2564; 9, BamHI *S. lavendulae* NRRL 2564; 10, BclI *S. lavendulae* KY681; 11, BamHI *S. lavendulae* KY681; and 12, λHindIII DNA ladder.

Preferred DNA probes also include probes that are complementary to all or a portion of the DNA sequence for the mcr and mrd gene locus. These probes include sequences complementary to the DNA sequence of 6.7 kb BclI fragment of pDHS3000 encoding the mcr locus and the 4.2 kb BclI fragment of pDHS3001 encoding the mrd locus. These probes have been used to identify DNA sequences in the genome of resistant Streptomyces spp. by hybridization as shown in FIG. 5. Portions of the DNA sequence can include restriction enzyme fragments, preferably those shown in FIG. 6 or FIG. 12.

DNA probes can be prepared by standard methods such as automated DNA synthesis or as restriction endonuclease fragments. DNA probes are preferably labelled with a detectable agent such as a radioactively labelled nucleotide. Once a sequence is selected, a DNA probe labelled with the detectable agent can be prepared by automated DNA synthesis, polymerase chain reaction, nick translation, and other methods as described in Sambrook et al.

DNA probes are used to detect homologous sequences by hybridization. A DNA probe according to the invention has sufficient complementarity to a DNA or RNA sequence so that it can hybridize to a DNA or RNA sequence under either low or high stringency conditions. Sufficient complementarity depends on the length of the probe, whether any mismatches are present on the probe, and the stringency conditions and the effect of these factors on hybridization are known to those of skill in the art. Typically, in hybridizations conducted under lower stringency conditions, the probe can be smaller in length and have some mismatches in sequences. Methods of DNA-DNA and DNA-RNA hybridization as well as high and low conditions of stringency are known to those of skill in the art and are described in Sambrook et al.

D. Transformed Cells

Once an expression cassette is formed in accordance with the invention, it can be used to form transformed cells. Transformed cells carrying a expression cassette can be used in method to identify agents that inhibit resistance of the cell to the DNA bioreductive alkylating or cleaving agent. Transformed cells include an expression cassette comprising a DNA sequence that provides resistance to a cell to a DNA bioreductive alkylating or cleaving agent operably linked to a promoter functional in the cell. The preferred DNA sequence substantially corresponds to the DNA sequence for the mcrA and mcrB genes. The expression cassette provides the cell with resistance to the DNA bioreductive alkylating or cleaving agent.

A transformed cell can be formed by standard methods using an expression cassette of the invention prepared as described herein. Briefly, a preferred expression cassette comprising a DNA sequence that substantially corresponds to a DNA sequence of mcrA and mcrB genes operably linked to a promoter is combined with a vector such as the plasmid pIJ702. A plasmid carrying the expression cassette is introduced into a suitable host by transformation methods such as calcium phosphate or calcium chloride precipitation, liposomes, electroporation, and the like. Transformants are selected for growth in the presence of the DNA bioreductive alkylating or cleaving agent. Transformed cells that are selected for growth in the presence of the agent are considered to be resistant to the agent.

Preferred host cells are those cells whose growth is inhibited in the presence of the DNA bioreductive alkylating or cleaving agent in the absence of the expression cassette (i.e., are sensitive). Specific examples of sensitive cells include Streptomyces species such as *Streptomyces lividans*, tumor cells such as the L1210, the EMT6, HG-29, BE human carcinoma, and the L5178Y. The preferred host cell is *Streptomyces lividans*. Specific examples of a DNA bioreductive alkylating or cleaving agent include mitomycin A, mitomycin B, mitomycin C, profiromycin, mitiromycin, and FR900147. The preferred DNA bioreductive alkylating or cleaving agents are mitomycin compounds.

In a preferred version, the plasmid pDHS3005 is introduced into protoplasts of *S. lividans* by polyethylene glycol transformation. Plasmid pDHS3005 comprises the 2.2 kb BalII-SphI DNA sequence including the mcrA and mcrB gene sequences. *S. lividans* transformants are selected for growth in the presence of about 10 to 100 µg/ml of mitomycin C. Transformed cells that can grow in the presence of at least about 10 µg/ml of mitomycin C are considered resistant to mitomycin C.

A transformed cell can also be a transformed cell line. A transformed cell line can be formed by amplifying the transformed cells selected for resistance to the agent. Methods of amplification and subculturing of cells to form homogeneous cell lines are known to those of skill in the art. A preferred sensitive cell line is a tumor cell line sensitive to mitomycins such as the L1210 cell line. A transformed cell line can exhibit transient expression of resistance of about 48 to 72 hours or can exhibit stable expression of resistance over several generations of growth (i.e., about 50–100 generations) in the presence of the DNA bioreductive alkylating or cleaving agent.

E. Polypeptides that are Encoded by DNA Sequences that Provide Resistance to a Cell to a DNA Alkylating or Cleaving Agent and Antibodies Thereto The invention also provides polypeptides that are encoded by DNA sequences that provide resistance to a cell to a DNA bioreductive alkylating or cleaving agent. While not meant to be a limitation of the invention, polypeptides can provide resistance to the cell to a DNA bioreductive alkylating or cleaving agent by inhibiting transport of the agent, deactivating the agent, inhibiting binding of the agent to DNA, or inhibiting the crosslinking or cleaving of DNA by the agent.

A polypeptide encoded by the DNA sequence that provides resistance to a cell to the agent can be identified by its presence in cell lysates of transformed cells compared with its absence in non-transformed cells using standard methods. A polypeptide can also be identified by determining whether the polypeptide can inhibit the binding to or activity of the DNA bioreductive alkylating or cleaving agent with a DNA sample by standard methods. Development of DNA-DNA crosslinks or breaks in the presence of the polypeptide and the agent can be assayed by the alkaline elution method or the DNA renaturation method as described by Masuda et al., cited supra. Once identified, polypeptides can be isolated from transformed cell lysates using standard methods. Preferred polypeptides are encoded by the mcr locus can have a molecular weight within the range of about 10 to 60 kD as measured by SDS-PAGE.

An especially preferred example of a polypeptide that is encoded by a DNA sequence that provides resistance to a DNA alkylating or cleaving agent is the MCRA polypeptide. The MCRA polypeptide is about a 56,000 dalton molecular weight polypeptide as determined by SDS-PAGE that can be isolated from a transformed cell such as *S. lividans* carrying the plasmid pDHS3000. A portion of the N-terminal sequence of the MCRA polypeptide isolated from transformed cell lysates is identical to that of the predicted amino acid sequence for the polypeptide encoded by the mcrA gene as shown below:

Predicted MCRA Sequence: MSTQWGWALEPDQPGY (SEQ ID NO: 12)

N-terminal Sequence of isolated MCRA: STQWG-WALEPD (SEQ ID NO: 13)

The predicted amino acid sequence of the MCRA polypeptide shares amino acid homology with the 6-hydroxy-D-nicotine oxidase and L-gulono-lactone oxidase. Both of these enzymes catalyze reactions using FAD cofactor-mediated oxidation.

It is believed that a cofactor such as FAD binds to the His$^{64}$ residue of MCRA and mediates oxidative deactivation of a DNA bioreductive alkylating or cleaving agent such as mitomycin compounds. The UV spectrum of purified MCRA and electrospray spectrometry indicates that FAD is covalently bound to MCRA as a cofactor.

MCRA and other polypeptides that are encoded by DNA sequences that impart resistance to DNA bioreductive alkylating or cleaving agents can be analyzed by inhibition of DNA or binding to alkylating or cleaving agents that are radiolabeled. This inhibition can be assessed by binding of the polypeptide to a radiolabeled agent or by inhibition of activation of the agent in the presence of a reducing agent. The polypeptides preferably have oxidase activity and prevent reductive activation of the alkylating and/or cleaving agents.

The invention also includes antibodies to polypeptides encoded by DNA sequences that provide resistance to a cell to a DNA alkylating or cleaving agent. Once such polypeptides are identified, antibodies specific for the polypeptides can be prepared by standard methods known to those of skill in the art.

The antibodies can be used in assays to detect expression of polypeptides, to isolate and purify polypeptides and DNA sequences encoding them, and to identify and isolate related polypeptides in other resistant cells.

Polyclonal antibodies can be formed by injecting an animal such as a mouse several times intravenously with a polypeptide such as MCRA polypeptide. Typically about 0.5 to 2.0 mg are injected with Freund's incomplete adjuvant on at least three separate occasions. About one to two weeks after the last immunization, sera can be collected and the antibodies to a polypeptide such as MCRA can be quantitated using a standard ELISA test.

Monoclonal antibodies can be formed using the standard Kohler, Milstein technique. Pursuant to the Kohler, Milstein technique, immunization of the mammalian host is accomplished within the dose parameter by subcutaneous or intraperitoneal injection of the immunogen compound in adjuvant. Administration is repeated periodically and preferably for at least three injections. Three days before the spleen is removed, a priming injection of the immunogen compound is again administered. After their separation, the spleens are fused with the immortal mammalian cells such as mouse myeloma cells using the techniques outlined by Kohler and Milstein. Polyethylene glycol (PEG) or electrical stimulation will initiate the fusions. The fused cells are then cultured in cell wells according to culture techniques known in the art. Cellular secretions in the culture medium are tested after an appropriate time for the presence of the desired monoclonal antibodies.

The selection technique for identifying the appropriate monoclonal antibodies is an important aspect for determining the immunospecificity of the monoclonal antibody. The selection techniques call for determining the binding affinity of the hybridoma cellular products for polypeptides such as the MCRA and against cross-reactive controls. In particular, hybridoma culture fluid is tested in screening assays for immunoreactivity with the polypeptide MCRA and lack of immunoreactivity with bovine serum albumin.

Screening assays can be performed by immunoenzymatic assay, immunofluorescence, fluorescence activated cell sorter, radioimmunoassay, immunoprecipitative assay or inhibition of biological activity. The hybridoma culture selected will exhibit strong binding characteristics to a polypeptide such as the MCRA polypeptide and exclude binding with a variety of controls including bovine serum albumin and a polypeptide encoded with the mcrB gene.

Following the identification of cell cultures producing the desired monoclonal antibodies, subcloning to refine the selected culture can be performed. These techniques are known to those skilled in the art. See, for example, Goding, James Goding, *Monoclonal Antibodies: Principles and Practice*, 2nd Edition, academic Press, San Diego, Calif. (1986).

F. Methods for Identifying Agents that Inhibit Resistance of a Cell to a DNA Bioreductive Alkylating or Cleaving Agent The invention also provides for methods of identifying agents that inhibit the resistance of cells to a DNA bioreductive alkylating or cleaving agent. Applications of such methods include identification of drugs or agents that might be useful to combat development of tumor drug resistance and design of analogs of the DNA bioreductive alkylating or cleaving agents that resistant cells are sensitive to.

One method of identifying agents that inhibit resistance of cells to a DNA bioreductive alkylating or cleaving agent involves the use of a transformed cell. A step of the method involves providing a transformed cell that is resistant to the DNA bioreductive alkylating or cleaving agent. The transformed cell comprises an expression cassette having a DNA sequence that provides resistance to a cell to a DNA bioreductive alkylating or cleaving agent, preferably the DNA sequence that substantially corresponds to the DNA sequence for the mcrA and mcrB genes, operably linked to a promoter functional in the cell. The transformed cell is incubated with an effective amount of an agent suspected to inhibit resistance of the cell to the DNA bioreductive alkylating or cleaving agent and an effective amount of the DNA bioreductive alkylating or cleaving agent. After suitable incubation, it can be determined whether the suspected agent inhibited the resistance of the cell to the DNA bioreductive alkylating or cleaving agent.

The transformed cell can be obtained as described herein. A preferred transformed cell is *S. lividans* carrying the pDHS3005 plasmid encoding the mcrA and mcrB genes. The DNA bioreductive alkylating or cleaving agent is preferably a mitomycin and the especially preferred agent is mitomycin C.

The agent suspected to inhibit resistance to mitomycin C can be agents that inhibit polypeptides such as the MCRA polypeptide or it can be analogs of the DNA alkylating or cleaving agents. Preferred examples of several analogs of mitomycins and methods for synthesizing such analogs are disclosed by Kasai et al., cited supra.

Effective amounts of the DNA bioreductive alkylating or cleavage agent or the agent suspected of inhibiting resistance to the DNA alkylating or cleaving agent are those amounts of the agent that would typically inhibit the growth of a sensitive cell. Effective amounts of mitomycin are known to those of skill in the art and preferably are 1 to 1,000 µg/ml and more preferably about 25 to 100 µg/ml. Effective amounts of an agent suspected to inhibit resistance are preferably within the same range and can be determined using standard dose response methodology.

Transformed cells are incubated in the presence of the DNA alkylating or cleaving agent and the agent suspected of inhibiting resistance of the cell to the DNA alkylating or cleaving agent. The incubation period depends on the assay used to determine whether there has been a change in the resistance of the cell to the DNA alkylating or cleaving agent. If the change in resistance of the cell is measured by DNA-DNA crosslinking as described by Masuda et al., cited supra, incubation can be as short as one hour. If the change in resistance of the cell is determined by growth of the transformed cells, the incubation period is about 1 to 10 days. An inability of the transformed cell to grow during the incubation period indicates that resistance of the cell to the DNA bioreductive alkylating or cleaving agent has been inhibited.

Determining whether the suspected agent inhibits resistance of the cell to a DNA alkylating or cleaving agent can be accomplished by several methods. As described herein, if the transformed cell's resistance to the DNA alkylating or cleaving agent is inhibited, its growth is inhibited about 10 to 100-fold. If the transformed cell's resistance is inhibited, DNA-DNA alkylation or crosslinking is increased about 2 to 20-fold over that of resistant cells.

In an alternative version, an agent suspected of inhibiting resistance of a cell to a DNA bioreductive alkylating or cleaving agent can be identified by determining if the suspected agent inhibits the function of a polypeptide encoded by a DNA sequence that provides resistance to the agent. The steps of this method involve providing a substantially pure MCRA polypeptide and a sample of a DNA containing CpG residues. The MCRA polypeptide and the sample of DNA are then incubated with an agent suspected to inhibit the function of the MCRA polypeptide and the DNA bioreductive alkylating and cleaving agent. After incubation, it is determined whether the suspected agent can inhibit the function of the MCRA polypeptide.

Substantially pure MCRA polypeptide can be obtained from a transformed cell line as described herein. A substantially pure polypeptide is a polypeptide that does not contain other polypeptides as determined by SDS-PAGE. See FIG. 10. A sample of DNA containing CpG residues can be obtained commercially or synthesized by automated DNA synthesis or isolated from a microorganism such as *S. lividans*. The agent suspected of inhibiting the MCRA polypeptide can bind to and block the function of MCRA. Such an agent could be an antibody to MCRA, an analog or derivative of mitomycin or a polypeptide designed to inhibit the binding or function of the FAD cofactor, e.g., a compound that covalently binds to or otherwise alters the $His^{64}$ residue of MCRA.

The function of the MCRA is predicted to include deactivation of the DNA alkylating or cleaving agent so that the DNA alkylating or cleaving agent can no longer bind to and/or cleave or alkylate DNA. An inhibition of the function of the MCRA polypeptide can be determined by whether the DNA bioreductive or alkylating or cleaving agent can bind to DNA and/or catalyze DNA crosslinks or breaks. Binding of the DNA alkylating or cleaving agent to the DNA and crosslinking or cleaving of DNA can be determined by standard methods. If the suspected agent inhibits the MCRA polypeptide, binding of the DNA alkylating or cleaving agent to DNA will increase about 2 to 10 fold or the DNA-DNA crosslink formation will increase about 2 to 20 fold.

G. Methods for Identifying DNA Sequences in Other Organisms that are Homologous to the mcr and mrd Gene Loci The invention also provides a method for identifying DNA sequences of other organisms that are homologous to the mcr and mrd gene loci that provide resistance to mitomycins. Homologous sequences in other organisms or cells, especially tumor cells, can be involved in the development of tumor drug resistance to DNA bioreductive alkylating or cleaving agents such as mitomycins. A preferred method involves generating a DNA library from cells of the organism using standard methods, followed by amplifying DNA sequences of the library using polymerase chain reaction. The polymerase chain reaction (PCR) includes the use of oligonucleotide primers that are complementary to portions of the mcr or mrd DNA sequences. The amplified products are isolated and analyzed for homology to mcr and mrd DNA sequence by hybridization to a DNA probe complementary to all or a portion of the mcr or mrd DNA sequence.

A DNA library from the cells of the organism can be generated using standard methods. The organism is preferably mammalian and the cells are preferably mitomycin C or multidrug-resistant tumor cells.

The DNA sequences in the DNA library are amplified by standard PCR techniques as described by Sambrook et al., cited supra. Oligonucleotide primers are preferably about 20 to 30 nucleotides in length. The sequence of the primers is selected to be complementary to the DNA coding sequence of the mcr gene locus or the mrd gene locus. Preferably, two different primers can be used in a single PCR reaction. The preferred primers are complementary to DNA sequences of the mcrA gene that encode amino acids 171 to 177:

```
CCT GTT CTG GGC GGT CCG CGG (SEQ ID NO:8)
 L   F   W   A   V   R   G  (SEQ ID NO:14)
``` and the DNA sequence of the mcrA gene that encodes the amino acids 429 to 436.

```
TAC GAC CCG GAC AAC ATG TTC CGA (SEQ ID NO:9)
 Y   D   P   D   N   M   F   R
```

Other primers can be selected from other sequences by identifying regions of the DNA sequence of the mcr or mrd locus that encode amino acids that are shared by several related proteins such as 6-hydroxy-D-nicotine oxidase. Amino acids 171 to 177 and 429 to 436 of the MCRA polypeptide are very similar to the amino acids found in 6-hydroxy-D-nicotine oxidase. Primers can be prepared by standard methods such as automated DNA synthesis.

Once primers are selected, they can be synthesized and combined with DNA sequences of the DNA library of the organism in a polymerase chain reaction. Conditions and amounts of material required for the polymerase chain reaction are known to those of skill in art and are described in Sambrook et al., cited supra. The polymerase chain reaction results in amplified products complementary to DNA sequences found in the source organism's genome.

The amplified products are then isolated and it is determined whether the amplified products are substantially homologous to the mcr or mrd gene loci. Homologous amplified products can be identified by hybridization under low stringency conditions to a DNA probe by standard methods. Hybridization conditions and DNA probes have been described herein. An amplified product is substantially homologous if it hybridizes to a DNA probe complementary to a portion of the mcr or mrd gene locus under low stringency conditions and preferably shares about 75–100% DNA sequence identity and more preferably, shares about 90–100% DNA sequence identity.

The preferred probes are those that are complementary to all or a portion of the 2.2 kb BlII-SphI DNA sequence from pDHS3005 encoding the mcrA and mcrB genes and the 4.2 kb BclI fragment of the pDHS30001 encoding the mrd locus.

Hybridization can be detected under both low and high stringency conditions using standard methods. Identification of such homologous DNA sequences from other organisms or cells can be used to identify agents that can inhibit resistance to DNA bioreductive alkylating or cleaving agents as described herein. Sequences that hybridize to the probes can be analyzed by standard methods such as restriction endonuclease mapping and DNA sequencing.

Polypeptides that are homologous or related to MCRA can also be detected in other types of resistant cells using antibodies specific for MCRA. For example, antibodies specific for MCRA can be used to identify homologous or related polypeptides in mitomycin resistant tumor cell lines using ELISA assays. The antibodies can also be used to isolate and purify related polypeptides using affinity chromatography.

H. Methods of Screening for Novel DNA Bioreductive Alkylating or Cleaving Agents The invention also provides methods for screening for novel DNA bioreductive alkylating or cleaving agents. A method involves incubating cells that are resistant to a DNA bioreductive alkylating or cleaving agents and detecting induction of expression of a DNA sequence that imparts resistance to a DNA bioreductive alkylating or cleaving agent such as mitomycin C. The cells can be naturally occurring resistant cells such a S. lavendulae or the cells can be transformed with an expression cassette including a DNA sequence that provides resistance to a cell to a DNA bioreductive alkylating or cleaving agent.

In a perfered version, a cellular extract from a resistant Streptomyces spp is incubated with a transformed cell such S. lividans carrying plasmid pDHS3000 and the cells are grown in the presence of the cellular extract for 48 hours to stationary phase. After 48 hours induction of mcrA is monitored. Induction of mcrA can be detected by detecting the presence of mcrA using ELISA as discussed in Example 3. All extracts exhibiting the ability to induce expression of mcrA or mrd can be further fractionated to identify the compounds that act as inducers of expression of resistance. These compounds can include novel DNA bioreductive alkylating or cleaving agents which could be useful as anticancer agents.

EXAMPLE 1

Cloning of Mitomycin C Resistance Genes

Genes encoding resistance to mitomycin C were identified and cloned from S. lavendulae DNA. Two gene loci were identified and designated mcr and mrd. The gene locus designated mcr encodes mcrA, mrd and ORF3. The gene locus designated mrd was also identified and isolated.

Bacterial Strains and Plasmids

The *E. coli* strain used was DH5αF'. The *S. lividans* strain used was 1326 (John Innes strain *S. lividans* 66). Streptoverticillium spp. used in this study have been identified as *Streptomyces lavendulae* in accordance with the proposition that the genus Streptoverticillium be unified with the members of the genera Streptomyces, in the species lavendulae (Witt et al., *System. Appl. Microbiol.*, 13:361 (1990)). *S. lavendulae* strains used in this study were B619, NRRL 2564, KY681, and PB1000. Strain B619 was a gift from Abbott Laboratories. Strain PB1000 was derived from strain B619 as described below. Strain NRRL 2564 was obtained from the American Type Culture Collection (ATCC 27422). Strain KY681 was kindly provided by Kyowa Hakko Kogyo, Co., Ltd.

Strain PB1000 is a highly resistant MMC mutant. Mycelia of *S. Lavendulae* B619 was plated on MMC gradient plates. Mutants resistant to 250 μg/ml of mitomycin C were obtained. After several rounds of replating, selected mutants were identified with resistance to greater than 1000 μg/ml of MMC. One such mutant designated PB1000 was highly resistant to MMC and had a normal morphological phenotype.

The high copy Streptomyces plasmid pIJ702 available from John Innes Institute, Norwich, England was used for all cloning work performed in *Streptomyces lividans*. pBR322 and pUC119 were used for all cloning work performed in *E. coli* and these can be obtained from commercially available sources.

Plasmids used to clone mitomycin C resistance genes were isolated and constructed using standard methods as follows. pDHS3000 and pDHS3001 were isolated from MMC resistant colonies obtained as described on pages 33–34. Plasmid preparations of MMC resistant colonies revealed two distinct DNA fragments. Some clones possessed pDHS3000 which contained a 6.7 kb insert (mcr) and conferred high level resistance (>100 μg/ml). Clones possessing pDHS3001 contained a 4.2 kb insert (mrd) and conferred lower levels of MMC resistance (25 μg/ml) in liquid culture. See Table I.

pDHS3002 was constructed by the digestion of pDHS3000 with PvuII and ClaI, Klenow treatment of the total digestion products, and ligation into the blunt-ended BglII site of pIJ702. pDHS3003 was constructed by the digestion of pDHS3000 with BamHI and ClaI, Klenow treatment of the total digestion products, and ligation into the blunt-ended BglII site of pIJ702. pDHS3004 was constructed by the digestion of pDHS3003 with BglII and PstI, Klenow treatment of the total digestion products, gel purification of the 3.5 kb fragment, and ligation of the purified fragment into the blunt-ended BglII site of pIJ702. pDHS3005 was constructed by the digestion of pDHS3003 with BglII and SphI, Klenow treatment of the total digestion products, gel purification of the 2.2 kb fragment, and ligation of the purified fragment into the blunt-ended BglII site of pIJ702. pDHS3006 was constructed by the digestion of pDHS3003 with FspI and StuI, Klenow treatment of the total digestion products, gel purification of the 1.9 kb fragment, and ligation of the purified fragment into the blunt-ended BglII site of pIJ702. pDHS3007 was constructed by the digestion of pDHS3003 with NcoI and SphI, Klenow treatment of the total digestion products, gel purification of the 0.8 kb fragment, and ligation of the purified fragment into the blunt-ended BglII site of pIJ702. pDHS3008 was constructed by the digestion of pDHS3003 with PstI and StuI, Klenow treatment of the total digestion products, gel purification of the 1.8 kb fragment, and ligation of the purified fragment into the blunt-ended BglII site of pIJ702. pDHS3009 was constructed by the digestion of pDHS3003 with PstI and NcoI, Klenow treatment of the total digestion products, gel purification of the 2.2 kb fragment, and ligation of the purified fragment into the blunt-ended BglII site of pIJ702. pDHS3010 was constructed by the digestion of pDHS3000 with BclI, Klenow treatment of the total digestion products, and ligation into the BamHI site pBR322. See Table I.

TABLE I

Bacterial strains and plasmids

| Strains or Plasmids | Relevant Characteristics | Source or Reference |
|---|---|---|
| STRAINS | | |
| *Streptomyces lividans* | | |
| 1326 | mmc−, mc$^s$ | Hopwood et al. cited supra. |
| *Streptomyces lavendulae* | | |
| B619 | mmc+, mc$^r$ | Abbott Laboratories |
| NRRL 2564 | mmc+, mc$^r$ | ATCC |
| KY681 | mmc+, mc$^r$ | Kyowa Hakko Kogyo Inc. |
| PB1000 | mmc+,mc$^r$ | This work |
| *Escherichia coli* DH5αF' | | BRL |
| PLASMIDS | | |
| pIJ702 | tsr, hyg, mel | Hopwood et al., cited supra. |
| pDHS3000 | pIJ702 with 6.7 kb BclI DNA insert from *Streptomyces lavendulae* B619; contains mcr locus | This work |
| pDHS3001 | pIJ702 with 4.2 kb BclI DNA insert from *Streptomyces lavendulae* B619; contains mrd locus | This work |
| pDHS3002 | pIJ702 with 5.0 kb PvuII-ClaI subclone from pDHS3000 | This work |
| pDHS3003 | pIJ702 with 3.0 kb BamHI-ClaI subclone from pDHS3000; contains mcrA, mcrB, and orf 3 | This work |
| pDHS3004 | pIJ702 with 3.5 kb BglII-PstI subclone from pDHS3003; contains mcrA, mcrB, and orf 3 | This work |
| pDHS3005 | pIJ702 with 2.2 kb BglII-SphI subclone from pDHS3003; contains mcrA and mcrB | This work |
| pDHS3006 | pIJ702 with 1.9 kb FspI-StuI subclone from pDHS3003; contains mcrA | This work |
| pDHS3007 | pIJ702 with 0.8 kb NcoI-SphI subclone from pDHS3003; contains mcrB | This work |
| pDHS3008 | pIJ702 with 1.8 kb PstI-StuI subclone from pDHS3003; contains orf 3 | This work |
| pDHS3009 | pIJ702 with 2.2 kb PstI-NcoI subclone from pDHS3003; contains mcrB and orf 3 | This work |

TABLE I-continued

Bacterial strains and plasmids

| Strains or Plasmids | Relevant Characteristics | Source or Reference |
|---|---|---|
| pDHS3010 | pBR322 with 8.3 kb BclI subclone from pDHS3000 | This work |
| pBR322 | lacZ, bla, tet | BRL |

Media and Growth Conditions.

Streptomyces spp. were grown in tryptic soy broth (TSB) for DNA isolation, or in yeast extract malt extract (YEME) broth supplemented with 5 mM $MgCl_2$ and 5 mM glycine for transformation. Streptomyces were grown on R2YE agar medium and E. coli was grown on LB agar medium. Growth media were supplemented with the appropriate antibiotics at the following concentrations: Agar plate; ampicillin, 50 µg/ml; mitomycin C, 20 µg/ml; thiostrepton, 20 µg/ml: Luria Broth; ampicillin, 50 µg/ml; mitomycin C, 5 µg/ml; thiostrepton, 5 µg/ml.

Bacterial Transformations.

Preparation of S. lividans 1326 protoplasts and their subsequent transformations were performed as described in Hopwood et al., *Genetic Manipulations of Streptomyces. A Laboratory Manual*, John Innes Foundation, Norwich U.K. (1985). Competent E. coli DH5αF' were prepared and transformed according to Sambrook et al., *Molecular Cloning: A Laboratory Manual*, Cold Spring Harbor, N.Y. (1985).

DNA Manipulations and Sequencing.

Isolation and purification of DNA was performed according to Sambrook et al., cited supra. Restriction enzymes were obtained from Gibco/BRL (Gaithersburg, Md.), and digestions were performed according to the manufacturer's instructions. Genomic DNA was isolated from *Streptomyces lavendulae* B619 using the Kirby protocol described in Hopwood et al., cited supra. $^{32}$P-labeled DNA probes were generated by nick-translation as described by Sambrook et al., cited supra., and Southern blot hybridizations were performed as described by Hopwood et al., cited supra., using low stringency conditions. For example, after hybridization in 50% formamide, 5×SSC, 25 mM sodium phosphate, 0.1% sodium pyrophosphate, and 1×Denhardt's solution, washing at 55° will remove any hybridized probe with less than about 76% penology to the bound sequences.

To determine the nucleotide sequence of mcr locus, the 3.2 kb BamHI/ClaI fragment from pDHS3003 was cloned into pUC119. The internal 2.5 kb ApaI fragment was purified using the GeneClean II kit (BIO 101, La Jolla, Calif.) according to the manufacturer's instructions. Different allotments of this fragment were digested with SalI, BstEII, and RsaI. In addition, the fragment was double digested with XhoI and NcoI. The digestion products were blunt-ended using Klenow as described by Sambrook et al., cited supra. These products were cloned into the SmaI site of pUC119. Single-stranded DNA was isolated from clones containing inserts using the helper phage MK037. Single-stranded DNA sequencing was performed using the dideoxy chain termination method. (Sequenase kit, version 2.0; deazaguanosine dinucleotides, United States Biochemical; and [α-$^{35}$S] dATP.) DNA sequence analysis was performed using the Intelligenetics, and the Wisconsin Genetics Computer Group software programs version 7.0 (Madison, Wis.). "FRAME" analysis was performed using the Intelligenetics Geneworks codon composition DNA algorithm with the nucleotide range set at 25 base pairs 5' and 3' of the DNA sequence analyzed. The sequence is shown in FIG. 2.

To determine the sequence for mrd, a 5.5 kb BclI fragment from plasmid pDHS3001 was isolated and subjected to shotgun cloning into pUC119. Briefly, the BclI generated fragments were ligated using T4 DNA ligase. The ligated product was disrupted using sonication to generate randomly sized fragments. Selected fragments ranging in size from 500 to 1000 bp were isolated via agarose gel electrophoresis. Fragments were cloned into SmaI site in pUC119. Single stranded DNA was produced and sequenced via the dideoxy chain termination method of Sanger et al. Analysis of sequencing gel is being conducted with the aid of computer software "GeneWorks®" by Intelligenetics, Mountain View, Calif., and Frame by GeneWorks from Intelligenetics. The sequence for the mrd (formerly mcrB) locus of S. lavendulae is shown in FIG. 11. The sequence has two complete and two partial open reading frames (ORF) as follows: from the 5' end an incomplete reading frame at 1–320 nucleotides; an open reading from 1055–1519 nucleotides; an open reading frame from 1871–3376; and an incomplete reading frame from 3376–4052. The current map of the mrd locus is shown in FIG. 12. The translation product of the ORF at the 3' end of the clone aligns with mycinamicin IV hydroxylase from *Micromonospora griseorubida*. A polypeptide having the predicted amino acid sequence encoded by this ORF shows a strong similarity to mycinamicin hydroxylase.

Identification, Cloning and Sequencing of Mitomycin C Resistance Genes

In order to identify and characterize S. lavendulae DNA that confers resistance to MMC, a S. lavendulae DNA library was constructed by isolating total chromosomal DNA, digesting completely with BclI, and ligating into the BglII site in the high copy Streptomyces vector pIJ702 as described by Hopwood et al., cited supra. Protoplasts of S. lividans (S. lividans determined to be suitable hosts because of their high sensitivity to MMC in liquid culture, and on agar medium (total inhibition of growth was observed at 10 µg/ml)) were generated and transformed using standard methodology.

The sensitivity of S. lividans 1326 was tested for its resistance to MMC by plating spores onto plates containing 1, 10, and 25 µg/ml MMC. Some growth was observed at 10 µg/ml MMC, however, growth was not observed at 25 µg/ml MMC. B619 genomic DNA was digested with BclI to completion and ligated into the BglII site pIJ702. S. lividans protoplasts were transformed with the ligation mixture and plated onto R2YE agar. After 24 hours, regenerated protoplasts were overlaid with 25 µg/ml thiostrepton. Approximately 8000 mitomycin C resistant colonies appeared several days later. After the colonies began to sporulate they were replica-plated onto R2YE containing 25 µg/ml thiostrepton and MMC.

Screening for MMC resistant colonies was accomplished by overlaying the regenerated S. lividans protoplasts with thiostrepton to select for colonies containing recombinant pIJ702 plasmids. Following several days of growth and sporulation, colonies were replica-plated onto medium containing 25 µg/ml MMC. Two types of drug resistant colonies were obtained; the first appeared after 24–48 hours and grew at a normal rate, whereas the second type appeared at the same time but grew at a significantly slower rate.

Plasmid preparations of MMC resistant colonies revealed two distinct DNA fragments. The clones that grew at a normal rate possessed pDHS3000, which contained a 6.7 kb fragment (mcr) and conferred high levels of resistance (>100 µg/ml) in liquid medium. The clones that grew at a reduced rate possessed pDHS3001, which contained a 4.2 kb DNA insert (mrd) and conferred lower levels of MMC resistance (25 µg/ml) in liquid culture (Table I).

Both plasmids were purified and used individually to re-transform *S. lividans*, confirming the MMC resistant phenotype. Transformation of pIJ702 as a control resulted in MMC sensitive *S. lividans*, establishing that in each case, cloned DNA alone was responsible for conferring MMC resistance. These results established that *S. lavendulae* possesses at least two genetic loci that confer differential levels of MMC resistance to *S. lividans*.

DNA sequencing of mcr (FIG. 2) was performed on a 3.2 kb subclone (pDHS3003) of pDHS3000 shown to confer high levels of MMC resistance in *S. lividans*. Analysis of the sequence using the Geneworks codon composition algorithm revealed three open reading frames (ORFs designated mcrA, mcrB, and ORF3). The predicted direction of transcription for mcrA and mcrB is left to right, while ORF3 would be transcribed divergently. The predicted start site for mcrA is an ATG codon at nucleotide position 131. The predicted stop codon for mcrA is located at nucleotide position 1475 and a non-coding region of 49 bp separates it from mcrB. The putative translational start site for mcrB is a GTG codon at nucleotide position 1527, preceded by a ribosome-binding site centered ~8 nucleotides upstream. A characteristic stem loop structure suggests the presence of a rho-dependent terminator at the 3'-end of mcrB. The 3' end of ORF3 is separated by a 112 bp non-coding region from the 3' end of mcrB. The predicted start site of ORF3 is an ATG codon at nucleotide position 2862.

For sequencing of the mrd locus a 4.2 kb BclI fragment from plasmid pDHS3001 was isolated and subjected to shotgun cloning into pUC119 for single stranded DNA sequencing via the dideoxy chain termination method of Sanger et al. as described at pages 12–13. Analysis of sequencing gels made with the aid of "Geneworks®" by Intelligenetics, Mountainview, Calif. See FIGS. 11 and 12. Sequence Similarity of mcrA to the Hydroxy-D-nicotine Oxidase from Arthrobacter Oxidans.

Figure 4:
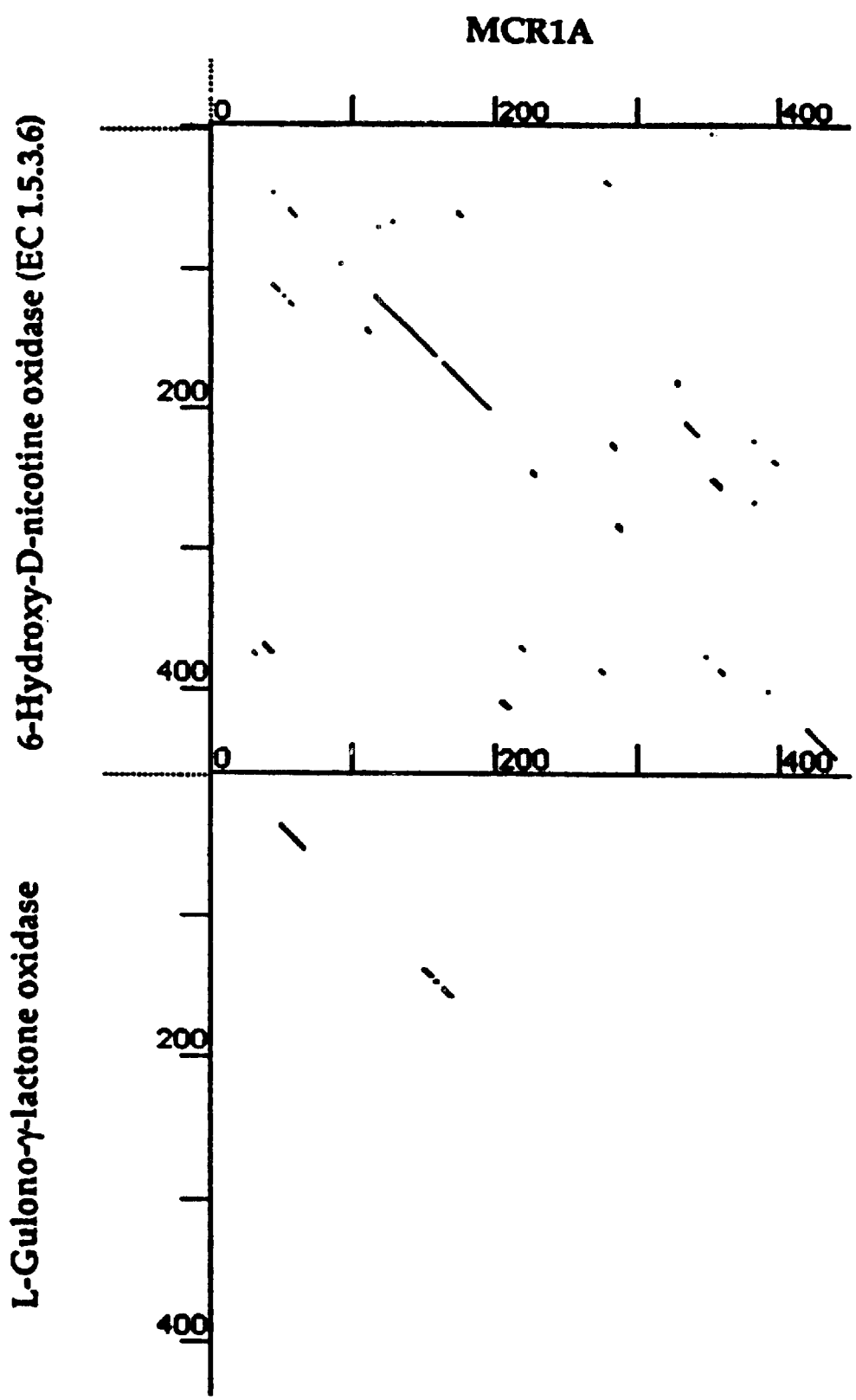
FIG. 4. Dot plot comparisons of the mcrA deduced protein sequence with 6-hydroxy-D-nicotine oxidase (6HDNO) and L-gulono-γ-lactone oxidase. (A) mcrA (horizontal axis) and 6-hydroxy-D-nicotine oxidase; (B) mcrA (horizontal axis) and L-gulono-γ-lactone oxidase. Analysis was performed using a stringency of 33% identity with the range set at 10 amino acids.

Computer-assisted comparison of the deduced product of mcrA with other proteins revealed significant similarity with the amino-terminal half of 6-hydroxy-D-nicotine oxidase (6HDNO) from *Arthrobacter oxidans*. See FIG. 3. Brandsch et al., *Eur. J. Biochem.*, 167:315 (1987). The 6HDNO operates in the catabolism of nicotine by catalyzing a two electron oxidation of the pyridine ring system, and the stereospecific hydroxylation of the carbon atom adjacent to nitrogen. Significantly, alignment with the deduced mcrA protein sequence includes a co-linear arrangement with the known FAD-binding site centered at His$^{71}$ of the 6HDNO polypeptide chain (Brandsch et al., cited supra.). The His$^{71}$ residue of 6HDNO has been shown to bind FAD covalently, as opposed to the 6-hydroxy-L-nicotine oxidase, which involves a noncovalent FAD-binding site (Mohler et al., *Eur. J. Biochem.*, 32:1364 (1972). Another significant comparison was found with the L-gulonolactone oxidase (L-GLO) from liver microsomes, which involves FAD-mediated oxidation as well (FIG. 4). Interestingly, there is considerable sequence divergence at the carboxy-terminal half of the mcrA, and 6HDNO, and L-GLO protein sequences.

EXAMPLE 2

Genomic and Transcriptional Analysis of the mcr loci Conferring Resistance to MMC Hybridization of mcr and mrd to Genomic DNA of Independent Isolates of MMC-producing *S. lavendulae*.

In order to establish that mcr and mrd were present in MMC-producing *S. lavendulae*, we performed Southern blot analyses of genomic DNA from four MMC producing *S. lavendulae* strains (B619, PB1000, NRRL 2564, KY681), *S. lividans* 1326 (negative control), using 6.7 kb BclI fragment containing mcr from pDHS3000 and using 4.2 kb BclI fragment containing mrd from pDHS3001 as hybridization probes. See FIG. 5. Distinct DNA bands were observed in each of the MMC-producing *S. lavendulae* strains. In contrast, *S. lividans* showed no hybridization signals with either probe. Interestingly, the copy number of mcr showed variability in the MMC-producing strains of *S. lavendulae*, and corresponded to the level of MMC resistance exhibited by the specific MMC-producing strains. This is particularly evident in *S. lavendulae* strain PB1000, which expressed the highest level of resistance to MMC and has the highest copy number of mcr. PB1000 was generated specifically as a highly resistant variant, which was isolated after a strain development protocol using high level exposure to MMC.

Figure 5B:
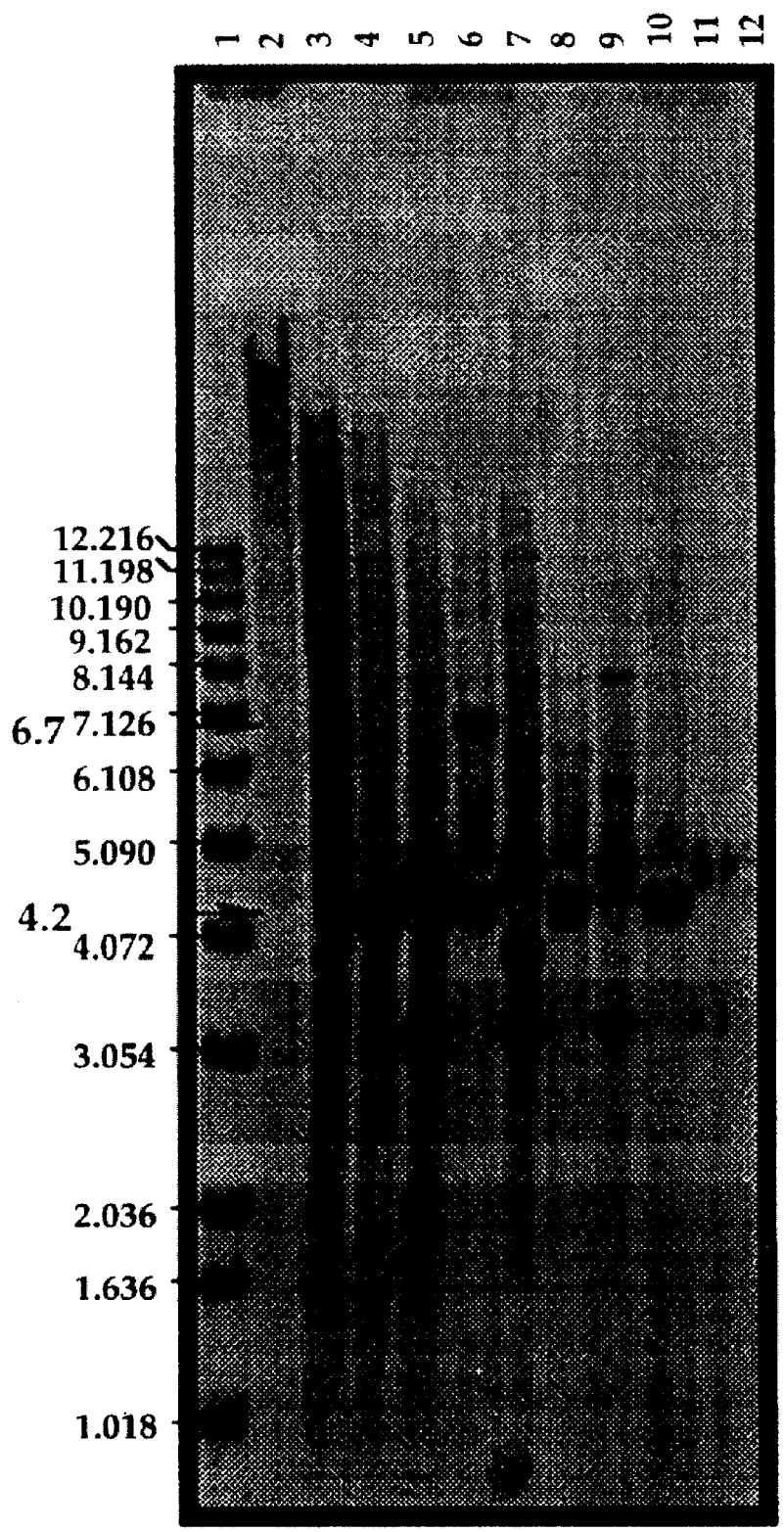
FIG. 5B: *S. lavendulae* probed with a 4.2 kb BclI insert of pDHS3001 encoding mrd. Lanes: 1, 1 kb ladder; 2, BclI *S. lividans* 1326; 3, BamHI *S. lividans* 1326; 4, BclI *S. lavendulae* B619; 5, BamHI *S. lavendulae* B619; 6, BclI *S. lavendulae* PB1000; 7, BamHI *S. lavendulae* PB1000; 8, BclI *S. lavendulae* NRRL 2564; 9, BamHI *S. lavendulae* NRRL 2564; 10, BclI *S. lavendulae* KY681; 11, BamHI *S. lavendulae* KY681; 12, λHindIII DNA ladder.

When mrd was used as a probe in the Southern blot described above, hybridizing DNA was observed in each of the MMC-producing *S. lavendulae* strains. However, in contrast to mcr, the copy number of mrd appeared invariant among the MMC producing strains of *S. lavendulae*. Notably, there is low but significant hybridization between mcr and mrd, which is easily observed in the lanes containing pDHS3001 and pDHS3000 (FIG. 5), and in the lane containing PB1000 probed with mrd (FIG. 5B).

With the mcr sequence available, it was possible to determine which of the three genes were involved in conferring resistance to MMC in *S. lividans*. A series of subclones were constructed in pIJ702, and the results showed that mcrA and mcrB together were required (FIG. 6). The minimum amount of DNA sequence derived from mcrA and mcrB determined to confer resistance is defined by about a 2.2 kb BglII/SphI fragment generated from pDHS3005 plasmid. Levels of resistance in the construct containing these two genes were identical to that shown for pDHS3000 and pDHS3003 (>100 µg/ml).

A series of subclones from mrd locis have been prepared. Briefly, the 4.2 kb BclI fragment from pDHS3001 has been subcloned into p1J702 (plasmid) as shown in FIG. 12. The subclones have been introduced into *S. lividans* and resistance to MMC evaluated as described previously. A 3280 bp AflIII/AscI fragment. did confer resistance as well as a 3152 bp Not I fragment. A 1696 bp PvuI/AscI fragment and 1032 bp Not I/PvuI fragment are being evaluated. Resistance was conferred at 25 µg/ml.

RNA Isolation and Transcriptional Start Point Determination.

In order to determine the transcriptional start point for the putative mcrA-mcrB operon, a primer extension experiment was performed. RNA was extracted from *S. lividans* 1326 containing pDHS3000 grown in YEME medium with the addition of glycine to 5 mM and mitomycin C or thiostrepton to a concentration of 5 µg/ml. The cultures were allowed to grow for 72 hours. Additional drug was added to the mitomycin C induced culture at 5 µg/ml 35 minutes before RNA extraction. RNA was isolated using the Kirby protocol (from Hopwood et al., cited supra.). Primer extension was performed using the primer extension system of Promega Biotech (Madison,. Wis.) according to the instructions of the manufacturer. The oligonucleotide used for the extension reaction was 5'-CCACCTCCTGCTCGTCGGCC-3' (SEQ ID NO: 10), synthesized by Keystone Laboratories, Inc. (Menlo Park, Calif.).

RNA was isolated and the Northern blot was performed according to Hopwood et. al., cited supra. The RNA gel and electrophoresis was performed according to the formaldehyde method described by Current Protocols (Ausubel et. al., (1989)). The DNA probe used for the hybridization was a BglII/StuI fragment of pDHS3003. It was gel purified using the BIO 101 GeneClean II kit and radiolabeled using the Gibco/BRL random primers labeling system (Gaithersburg, Md.).

The primer extension protocol resulted in two primer extension products designated P1 and P2. The primer extension products were sequenced using dideoxy chain termination method. The results established the presence of two transcriptional start points, P1 and P2 with an expression ratio of ~5:1. The transcriptional start point for P1 is also the first nucleotide (bp 131) of the translational start codon. Thus, the mcrA transcript represents a leaderless mRNA, a phenomenon that has been described for several other Streptomyces resistance genes. The second, weaker primer extension product (P2) was observed that represents an mRNA with a transcriptional start point at nucleotide 170. This transcriptional start point may ensure basal levels of mcrA and mcrB mRNA. Hybridization of mcr to a 1.8 kb band in a Northern blot from *S. lavendulae* total RNA provides compelling evidence for a polycistronic mRNA including mcrA and mcrB.

EXAMPLE 3

Studies on Inducible Expression of mcrA

Gene expression of mcrA is induced by low levels of MMC. Completion of the DNA sequence for mcr suggested strongly that the mcrA gene product represented the protein induced after addition of the drug. It was determined whether other compounds in the mitomycin class were capable of inducing expression of the mcrA-mcrB operon.

A series of mitomycins and related compounds shown below were kindly provided by Dr. Hiromitsu Saito of Kyowa Hakko Kogyo, Co., Ltd.

| Mitomycin | X | Y | Z |
|---|---|---|---|
| Mitomycin A | OMe | OMe | H |
| Mitomycin B | OMe | OH | Me |
| Mitomycin C | $NH_2$ | OMe | H |
| Mitomycin D | $NH_2$ | H | Me |
| Mitomycin F | OMe | OMe | Me |
| Mitomycin H | OMe | H | Me |
| Porfiromycin | $NH_2$ | OMe | Me |

Individual drugs were added to fermentation flasks of *S. lividans* containing pDHS3000 (see Table 1) at t=0, and growth of the culture was allowed to proceed for 120 hours. The mycelium was harvested, and a cell extract prepared by sonication. Expression of mcrA was determined by detecting the 56,000 dalton polypeptide by SDS-PAGE method. The results showed that only mitomycin A (MMA) and MMC were capable of inducing expression of mcrA at 1 µg/ml. The other mitomycins induced expression of mcrA at concentrations of 5 µg/ml or greater.

Induction and expression of MCRA was evaluated for dose response to mitomycin C and the other mitomycins as well by detecting the presence of MCRA using antibodies to MCRA and an ELISA assay. The ELISA assay was conducted as follows. About 100–200 ul of 1.0–0.5 ug/ml antigen (MCRA) was added to Corning 96 well ELISA plates (cat no. 25801) and incubated at 37° C. for 2 hrs or 4° C. overnight. The contents were decanted and the plates were shaken dry. The wells were washed with 1× with PBS Tween 20 (0.05% T20). To the wells, 100–200 ul of 0.5% nonfat dry milk in PBS was added as a blocking agent. The plates were incubated for 1 hour at 37° C., the contents were decanted and the plates were shaken dry. The wells were washed four times with PBS-T20 and were shaken dry. One hundred microliters of primary antibody, at a dilution of 1:4000 in PBS with 0.5% nonfat dry milk, was added to the wells. The plates were incubated at 37° C. for 1 hour. The wells were washed four times with PBS-T20 and were shaken dry. One hundred microliters of secondary antibody (goat anti-rabbit HRP), at a dilution of 1:3000 in PBS-T20, was added to the wells and incubated at 37° C. for 1 hr or RT for 2 hrs. The contents were decanted and the plates were shaken dry. The wells were washed four times with PBS-T20 and were shaken dry. One hundred microliters of OPD solution was added to each well. The plates were agitated for 15 minutes at room temperature.

Figure 13A:
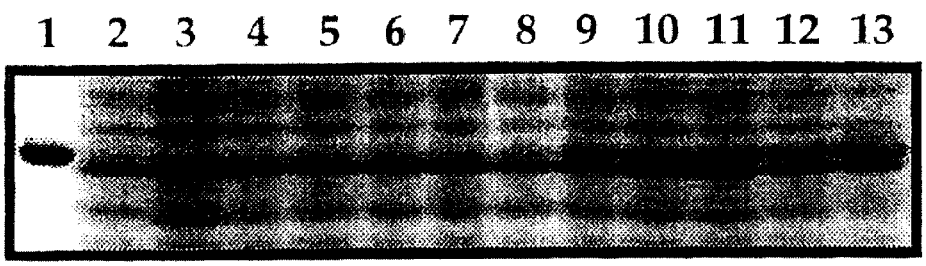
FIG. 13. MMC induction of MCRA expression in *S. lividans*/pDHS3000. Panel A shows Commassie blue stained SDS-PAGE gel of extracts from *S. lividans*/pDHS3000 grown with varying concentrations of MMC. Lane 1, purified MCRA control; Lane 2, *S. lividans*/pIJ702 grown with 1 µg/ml MMC; 3, *S. lividans*/pIJ702 grown with 0 µg/ml MMC; 4, *S. lividans*/pDHS3000 grown with 0 µg/ml MMC; 5, *S. lividans*/pDHS3000 grown with $1\times10^{-5}$ µg/ml MMC; 6, *S. lividans*/pDHS3000 grown with $1\times10^{-4}$ µg/ml MMC; 7, *S. lividans*/pDHS3000 grown with $1\times10^{-3}$ µg/ml MMC; 8, *S. lividans*/pDHS3000 grown with $1\times10^{-2}$ µg/ml MMC; 9, *S. lividans*/pDHS3000 grown with $1\times10^{-1}$ µg/ml MMC; 10, *S. lividans*/pDHS3000 grown with 1 µg/ml MMC; 11, *S. lividans*/pDHS3000 grown with 5 µg/ml MMC; 12, *S. lividans*/pDHS3000 grown with 10 µg/ml MMC; 13, *S. lividans*/pDHS3000 grown with 50 µg/ml MMC; Panel B shows Western blot of SDS-PAGE using anti-MCRA antibodies; Panel C shows MCRA expression as a function of MMC concentration.
Figure 13B:
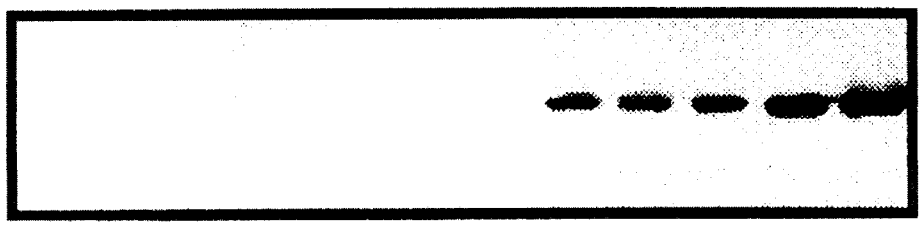
Figure 13C:
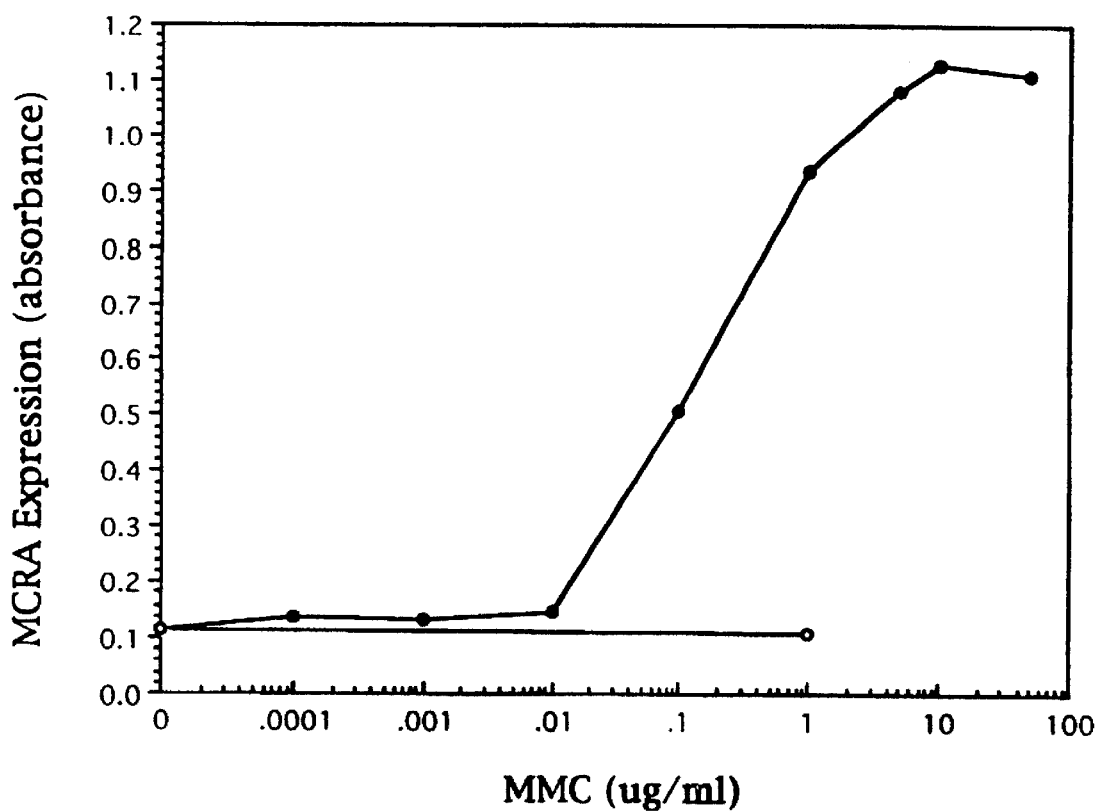

The results for induction with different amounts of mitomycin C are shown in FIG. 13. The expression of MCRA was MMC concentration dependent and maximum expression of MCRA occurred at concentrations of MMC greater than 10 ug per ml (FIG. 13). Concentrations of MMC above this level result in a decreased growth rate of the MMC producer *S. lavendulae* when it is grown in MMC, which indicates that the mechanism of resistance conferred by MCRA can be physiologically saturated (data not shown). Significantly, MCRA is induced by concentrations of MMC as low as 0.01 ug per ml (30 nM). The induction of MCRA may be induced at a much lower concentration physiologically in *S. lavendulae*.

Figure 14:
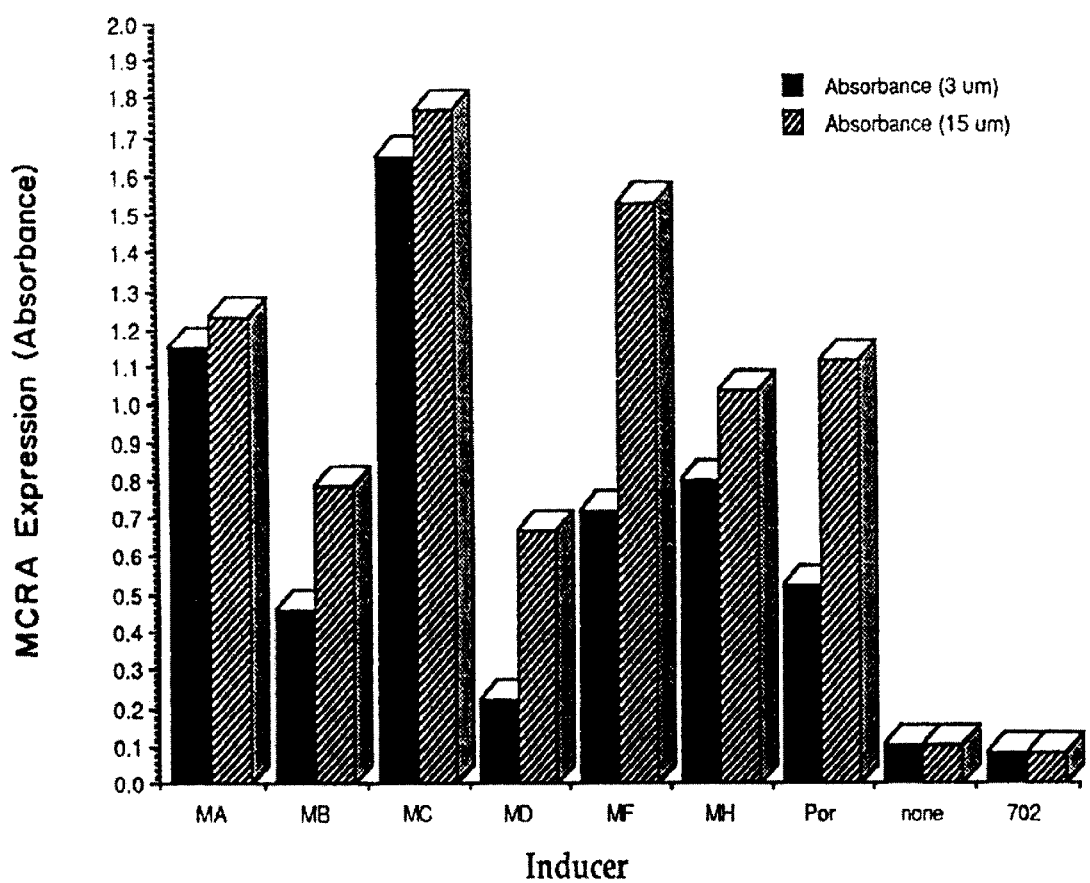
FIG. 14. Mitomycin induction of MCRA expression in *S. lividans*/pDHS3000. ■ represents cells incubated with 3 µm (1 µg/ml) of the mitomycins. □ represents cells incubated with 15 µM of the mitomycins. MA=mitomycin A; MB=mitomycin B; MC=mitomycin C; MD=mitomycin D; MF=mitomycin F; MH=mitomycin H; Por=porfiromycin; none control; 702=pIJ702.

Since MCRA appeared to provide resistance against other mitomycins, we evaluated those molecules for their ability to induce MCRA expression. Surprisingly, 3 uM of MMA or MMC were the only compounds to induce expression of MCRA that was visible by SDS-PAGE. However, ELISAs revealed that MCRA expression was induced by other mitomycins but to a lesser degree (FIG. 14). Higher concentrations of the mitomycins increased the level of MCRA expression.

This result is significant in view of the structural and biosynthetic relationship between MMA and MMC. Indeed, MMA is a precursor, and perhaps the earliest isolatable molecule in the pathway. Thus, it is reasonable that MMA would provide a primary induction signal for mcrA-mcrB expression in *S. lavendulae*.

Figure 15:
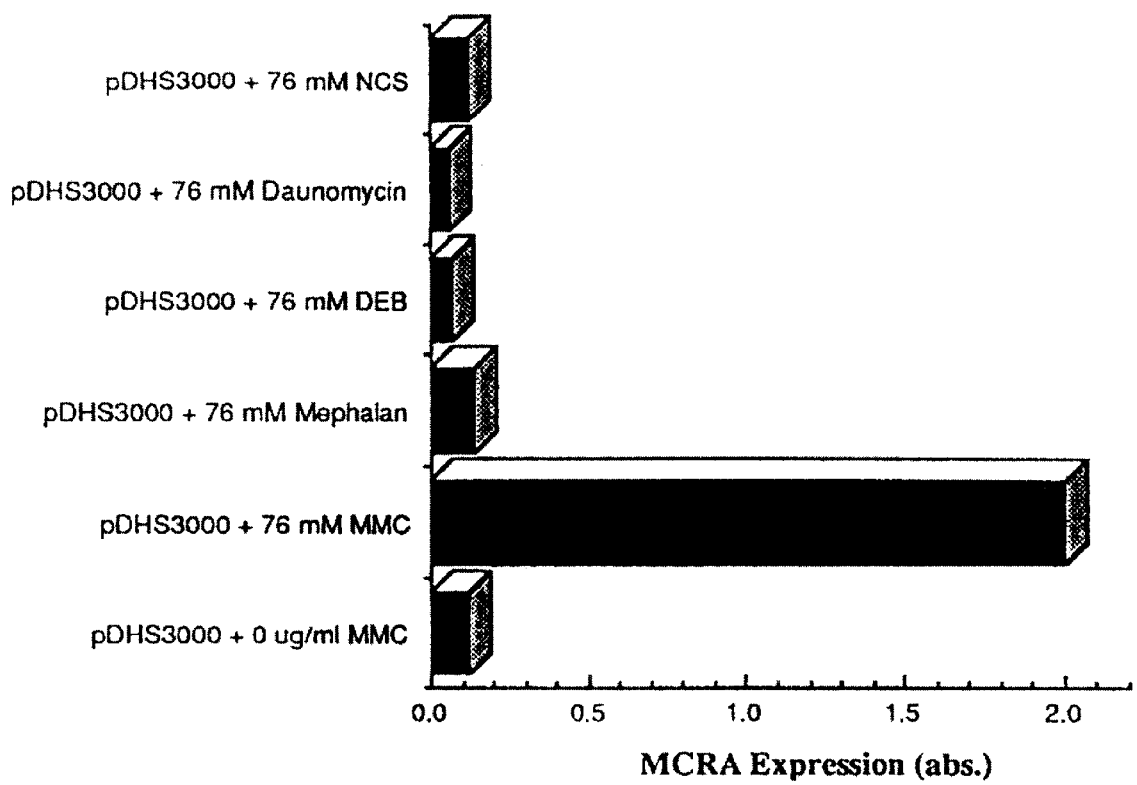
FIG. 15. Induction of MCRA expression as measured by ELISA assay in *S. lividans* cells containing pDHS3000. Cells were treated with 76 mM neocarzinostatin (NCS), mephalan, (±) −1,2:3,4 diepoxybutane (DEB), daunomycin and mitomycin C.

Experiments were performed to evaluate the ability of DNA alkylating agents to activate MCRA expression in order to determine whether induction of MCRA could be due to DNA damage as a result of DNA alkylation. As seen in FIG. 15, neocarzinostatin (NCS), mephalan, (±)-1,2:3,4-diepoxybutane (DEB), and daunomycin did not induce MCRA expression at 76 mM.

The ability of mcr locus to confer resistance to other mitomycins was examined. To determine whether resistance to other mitomycins and mitosanes is conferred by MCRA, we examined the ability of *S. lividans*/pDHS3000 to grow in the presence of MMC related molecules. As shown in Table II, resistance against all the compounds tested was conferred by pDHS3000. However, mitomycin D and H were not lethal to the control culture, *S. lividans* pIJ702. The non-lethality of mitomycins D and H does not reflect an inability of mitomycin D and H to penetrate cell barriers since these compounds were able to induce MCRA expression.

TABLE II

Mitomycin resistance conferred by pDHS3000

| Mitomycin (50 ug/ml) | *S. lividans* pIJ702 | *S. lividans* pDHS3000 |
|---|---|---|
| None | + | + |
| A | − | + |
| B | − | + |
| C | − | + |
| D | + | + |
| F | − | + |
| H | + | + |
| Porfiromycin | − | + |

EXAMPLE 4

Purification of MCRA

Due to the potential significance of MCRA as a novel resistance protein, the biochemical mechanism of action of the gene product will be investigated. The protein was purified to confirm its identity, and to perform a series of in vitro experiments concerning its precise biological function.

A purification scheme has been developed for MCRA. *S. lividans* containing pDHS3000 was grown to stationary phase in the presence of 5 μg/ml MMC. The mycelia was harvested after 54 hours of growth, centrifuged at 5,000 rpm for 10 minutes. The supernatant was decanted and the mycelial pellet resuspended in two volumes of protein extraction buffer (50 mM Tris.HCl pH 8.0, 10% glycerol, 2 mM EDTA pH 8.0). One half of the total mycelia was frozen at −80° C. while the other half was processed to isolate MCRA. All of the subsequent steps were performed at 4° C. The mycelia were disrupted by passing twice through a French press at 1500 psi. The homogenate was centrifuged at 10,000 rpm for 1 hour.

The homogenate supernatant was removed and proteins precipitated from it by the gradual addition of ammonium sulfate until 100% saturation. The saturated ammonium sulfate solution was allowed to stir overnight and then centrifuged at 10,000 rpm for 30 minutes. The supernatant was discarded and the pellet was resuspended in protein extraction buffer precooled to 4° C. The solution was dialyzed against 4 liters of protein extraction buffer five times over two days. The dialysis tubing was placed in a tray containing 200 g of PEG 6000 for 6 hours. Dialysis was performed against 4 liters of protein extraction buffer for 4 hours. The protein solution was removed from the dialysis tubing and centrifuged at 5,000 rpm for 10 minutes. The supernatant was removed and ammonium sulfate added to a concentration of 50%. The solution was allowed to stir for one hour and then centrifuged at 7,000 rpm for 10 minutes. The supernatant was removed and ammonium sulfate was added to bring the concentration up to 70%. The solution was allowed to stir for one hour and then centrifuged at 7,000 rpm for 10 minutes. The supernatant was removed and the pellet was resuspended in protein extraction buffer followed by dialysis against 4 L of buffer twice for 12 hours. The dialysis tubing was placed in a tray containing 100 g of PEG 6000 for 6 hours. The dialysis tubing was washed with distilled water and dialyzed overnight against 2 L of 50 mM phosphate buffer, pH 7.0. The dialysate was centrifuged at 5,000 rpm for 5 minutes. The supernatant was removed and sterile filtered.

This protein solution was loaded onto a DEAE column equilibrated with 50 mM phosphate buffer pH 7.0 using an Econosystem (BIORAD). A distinct yellow band could be seen at the head of the column. The column was washed with 1 L of the same buffer. The column was eluted with 1 L of 0 to 0.3 mM KCl gradient; 4 ml fractions were collected. Fractions were run on SDS-PAGE evaluated for a protein with the ability to co-migrate with the MC inducible protein from *S. lividans* 1326/pDHS3000 MMC induced cell extracts. Fractions containing the MCRA protein were concentrated using Centriprep (Amicon, Beverly Mass.) with a MW cut off of 30,000 according to instructions from the manufacturer. The concentrated protein solution was a bright yellow color. Gel filtration (Sephadex HR200, Pharmacia) was performed to further purify MCRA. The column (size) was washed with 50 mM phosphate buffer, pH 7.0 and loaded with 2 mls of the protein solution. The column was run at a flow rate of 0.2 mls/min. and 4 ml fractions collected. Fractions were analyzed by SDS-PAGE and revealed that the protein co-migrating with the MC inducible protein was substantially pure.

In an effort to isolate highly purified MCRA, a BIORAD prep cell employing SDS-PAGE was used. A 10% resolving gel (Gibco/BRL) was poured and the protein eluted using running buffer (Gibco/BRL). Fractions were collected and analyzed for the protein MCRA. Fractions containing pure MCRA were pooled and concentrated to 0.5 milliliter using centriprep 30. The buffer of the solution was changed by diluting the protein solution in PBS and concentrating. This was repeated twice. This protein solution was used for the production of polyclonal antibodies, N-terminal sequencing, mass and ultraviolet spectroscopy.

Figure 10:
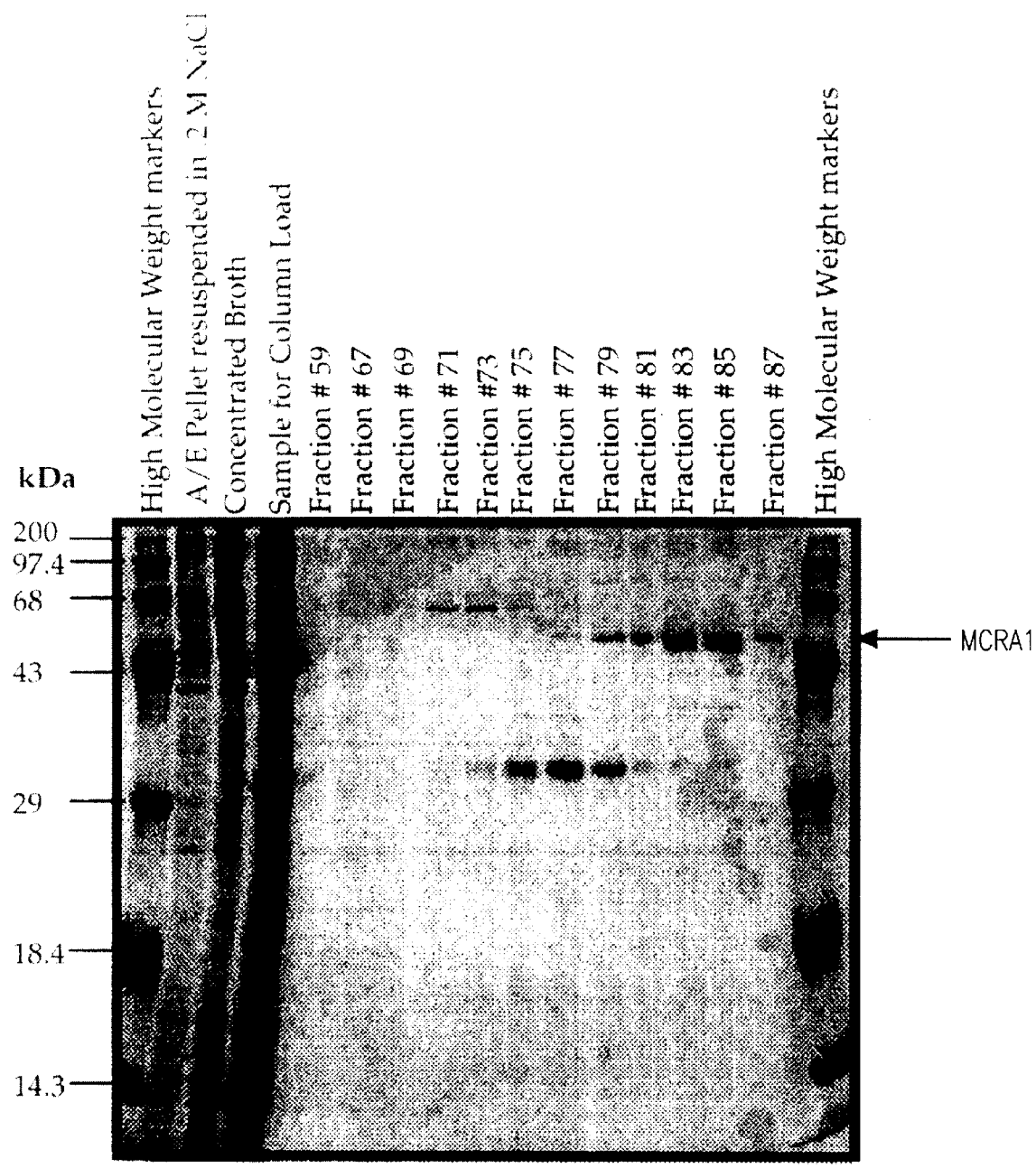
FIG. 10. SDS-PAGE of purified MCRA. MCRA was purified as described in Example 4.

The purified MCRA protein is about a 56,000 dalton protein on SDS-PAGE as shown in FIG. 10.

N-terminal sequence analysis of the MCRA protein was conducted by standard methods using an Applied Biosystems, Inc. 476 Sequencer (pulse liquid mode). Data analysis was done with the AB1 610 Sequence Analysis Software. The analysis shown below shows that the sequence of the isolated MCRA polypeptide agrees with the predicted amino acid sequence from the nucleotide sequence:

Predicted MCRA Sequence: MSTQWGWALEPDQPGY (SEQ ID NO: 12)

N-terminal Sequence Analysis MCRA: MSTQWG-WALEPD (SEQ ID NO: 16)

Figure 16:
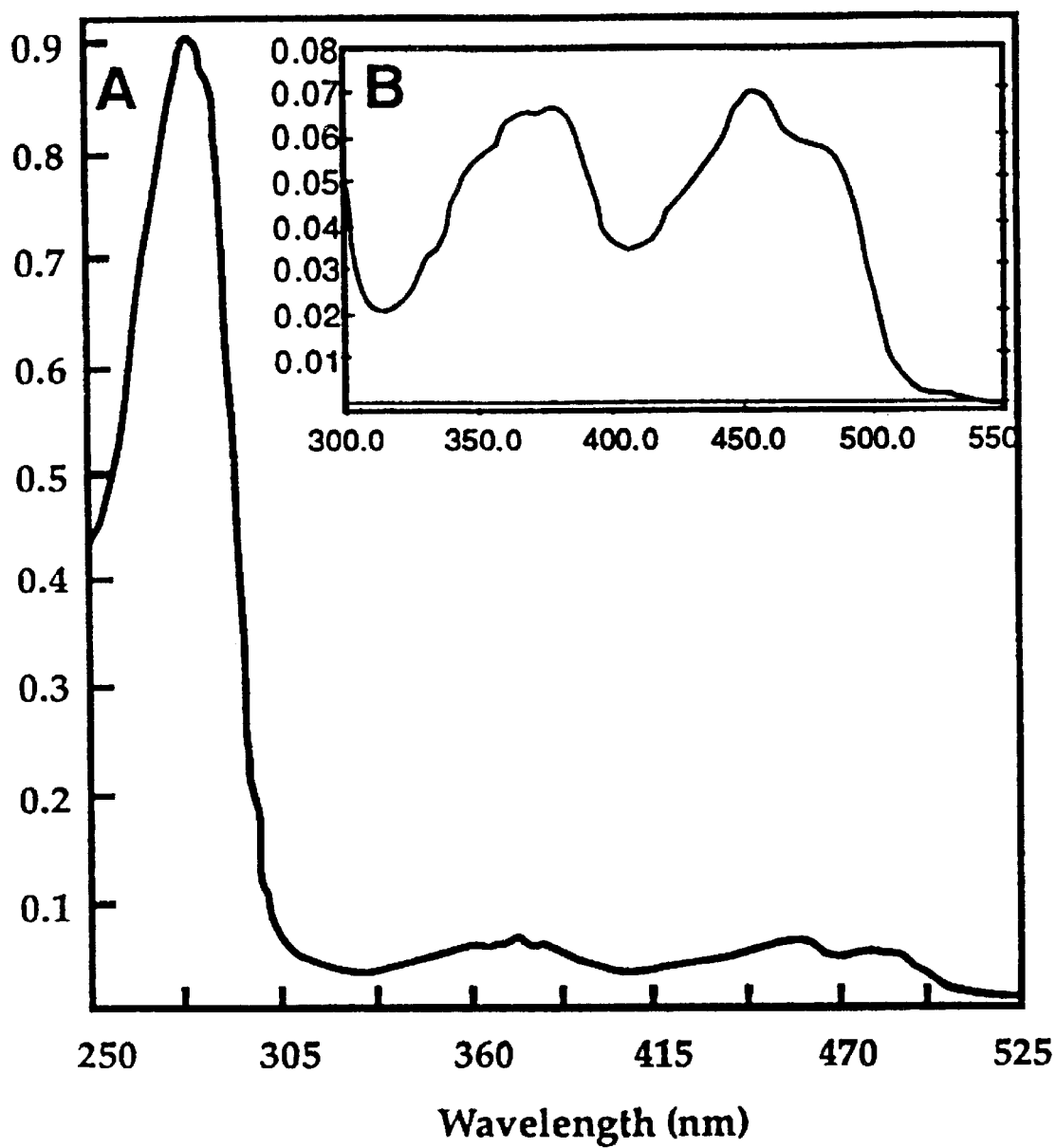
FIG. 16. Panel A UV spectrum of purified MCRA. Panel B=amplified spectrum from panel A between 300–500 nm.

Final purification of MCRA yielded a yellow protein, the UV spectrum of which suggested that the protein was covalently modified by the co-factor FAD (FIG. 16).

Covalent attachment of FAD was verified using several methods. The last step in the purification strategy for MCRA made use of a preparative SDS-PAGE cell which consequently denatured MCRA. If the co-factor FAD was non-covalently bound it would dissociate from the protein during this procedure. The results show that the molecular weight of the polypeptide was not altered by denaturation. These results indicate that FAD is covalently bound to MCRA.

In order to further verify that FAD was covalently bound to MCRA, linear time of flight and electrospray mass spectroscopy were performed on the modified MCRA protein. For linear time of flight mass spectroscopy, MCRA was dissolved in a solution of 50 nmol sinapinic acid in a 1:1 water ethanol mix (vol./vol.) with 0.1% Trifluoroacetic acid (TFA) at a final concentration of 0.3 pmol. The solution was dried on a sample slide and allowed to form a matrix. The matrix containing MCRA was analyzed by a Kratos (Manchester, UK) Komapact Maildi III using high power and 81 laser shots. Electrospray mass spectroscopy was performed by Cedric H. L. Shackleton, Ph.D., D.Sc. at the Mass Spectrometry Facility of the Children's Hospital Medical Center of Northern California.

The time of flight data revealed that the protein solution contained a single protein with the molecular weight of 49,244-Sinapinil acid (207)=49,037. While the electrospray data revealed a protein with molecular weight, 49,005 plus the exact mass of FAD. Both of these results clearly demonstrate that the MCRA protein with the N-terminal methionine removed, is covalently modified by FAD.

EXAMPLE 5

Development of Antibodies to MCRA

Once MCRA was isolated and purified, polyclonal antibodies were prepared. Monoclonal antibodies can be prepared by standard methods as described below.

Anti-MCRA polyclonal antibodies were produced as follows. 500 ug of purified MCRA was mixed in a ratio of 1:2 with complete Freunds adjuvant to homogeneity. The mixture formed an emulsion when passed back and forth through two connected syringes. Two New Zealand white rabbits were each inoculated with a suspension containing 500 ug of MCRA. After two weeks they were inoculated again and one month later they were reinoculated. After seven days, blood was removed from the rabbits and the serum was titered for antibodies against MCRA by ELISA assay. The polyclonal antibody titer was 1:8000. The ELISA assay was conducted as described in Example 3.

Monoclonal antibodies can be formed using the standard Kohler, Milstein technique. Pursuant to the Kohler, Milstein technique, immunization of the mammalian host is accomplished within this dose parameter by subcutaneous or intraperitoneal injection of the immunogen compound in adjuvant. Administration is repeated periodically and preferably for at least four injections. Three days before the spleen is removed, a priming injection of immunogen compound is again administered. After their separation, the spleen cells are fused with immortal mammal cells such as mouse myeloma cells using the techniques outlined by Kohler and Milstein. Polyethylene glycol (PEG) or electrical stimulation will initiate the fusions. The fused cells are then cultured in cell wells according to culture techniques known in the art. Cellular secretions in the culture medium are tested after an appropriate time for the presence of the desired cellular products.

The selection technique for identifying the appropriate monoclonal antibody is an important aspect for determining the immunospecificity of the monoclonal antibody. The selection techniques call for determining the binding affinity of the hybridoma cellular products for the mitomycin C resistance polypeptide MCRA and against cross-reactive controls. In particular, hybridoma culture fluid is tested in screening assays for reactivity with mitomycin C resistance polypeptide MCRA and lack of immunoreactivity with bovine serum albumin.

Screening assays can be performed by immunoenzymatic-assay, immunofluorescence, fluorescence-activated cell sorter, radioimmunoassay, immuno-precipitative assay or inhibition of biological activity. The hybridoma cultures selected will exhibit strong binding characteristics to the MCRA polypeptide and exclude binding with a variety of controls, including BSA and mcrB.

Following the identification of cell cultures producing the desired monoclonal antibodies, subcloning to refine the selected culture can be performed. These techniques are known to those skilled in the art. See, for example, Goding, James Goding, *Monoclonal Antibodies: Principles and Practice*, 2 nd Edition, Academic Press, San Diego, Calif. (1986), the disclosure of which is incorporated herein by reference.

Briefly, the appropriately selected cell culture is separated into one-cell units which are then recultured. The subclone cultures are then again tested for specific immunoreactivity, lack of cross-reactivity, and the amount of monoclonal antibody secreted. Those subcultures exhibiting the highest amounts of secreted monoclonal antibody are chosen for subsequent pilot development.

The antibodies specific for MCRA can be used in a variety of assays including ELISA assays and Western blot assays. The antibodies are useful for analyzing induction of MCRA in cells and identifying other related mitomycin resistance proteins and to analyze the functional domains of MCRA.

Western blots of cells expressing MCRA were conducted as follows. Completely dry filter with protein. Dip the filter for 2 sec into 100% Methanol and then soak in 1×TBS (Tris buffered saline) (20 mM Tris.HCl pH 7.5, 150 mM NaCl) for 2 minutes. Gently shake at room temperature in blocking solution (5% non-fat dry milk in TBS). Wash 3×10 minutes wash solution (0.1% non-fat dry milk in TBS). Add primary antibody to antibody incubation solution (1% non-fat dry milk, 0.05% Tween-20 in TBS) at 1:8000 and incubate for 2 hours at room temperature on orbital shaker. Wash 3×10 minutes wash solution. Add secondary antibody conjugate in TBS +0.05% Tween-20 (1:2000 goat anti-rabbit HRP Zymed). Incubate 2 hours on gentle shaker. Wash 3×10 minutes wash solution. Incubate with color development solution 25 mM Tris.HCl pH 7.5, 4-Chloro-1-napthol (3 mg/ml MeOH) 30% H2O2). Rinse with distilled $H_2O$ and blot with Whatman paper to dry and store.

EXAMPLE 6

Figure 7:
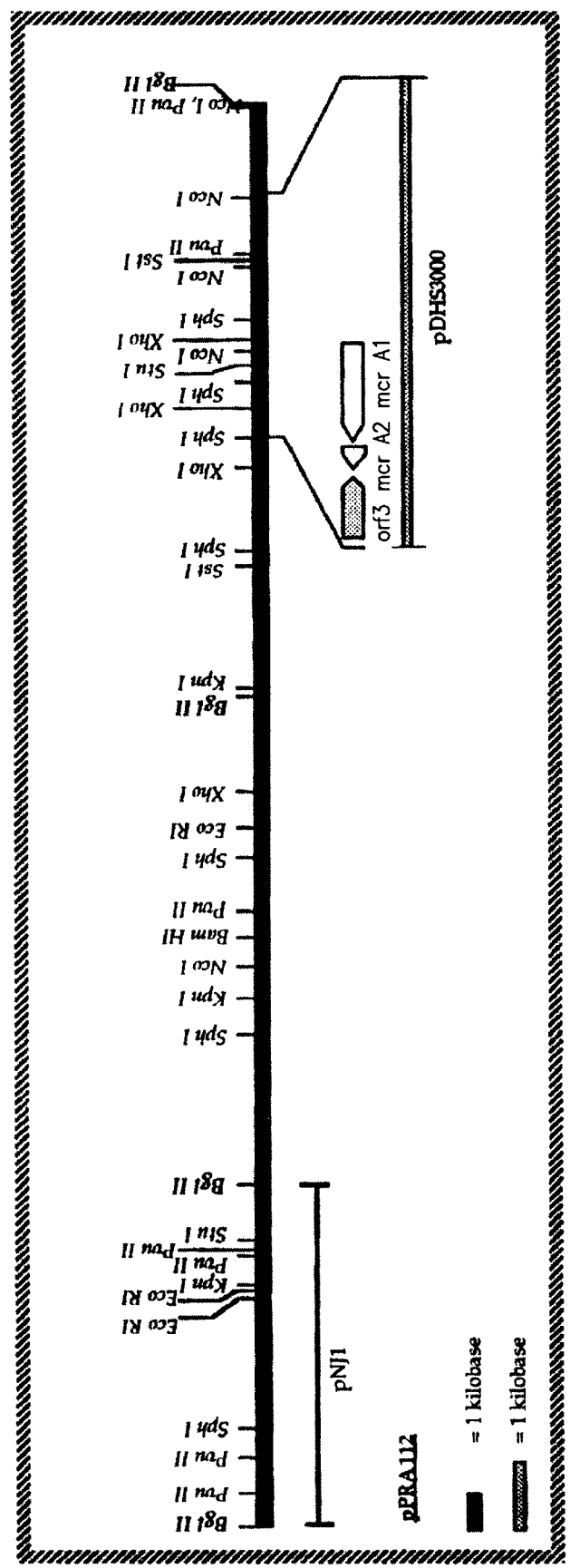
FIG. 7. Restriction-enzyme map of the pPRA112 cosmid clone containing *S. lavendulae* DNA adjacent to the mcr locus.
Figure 8:
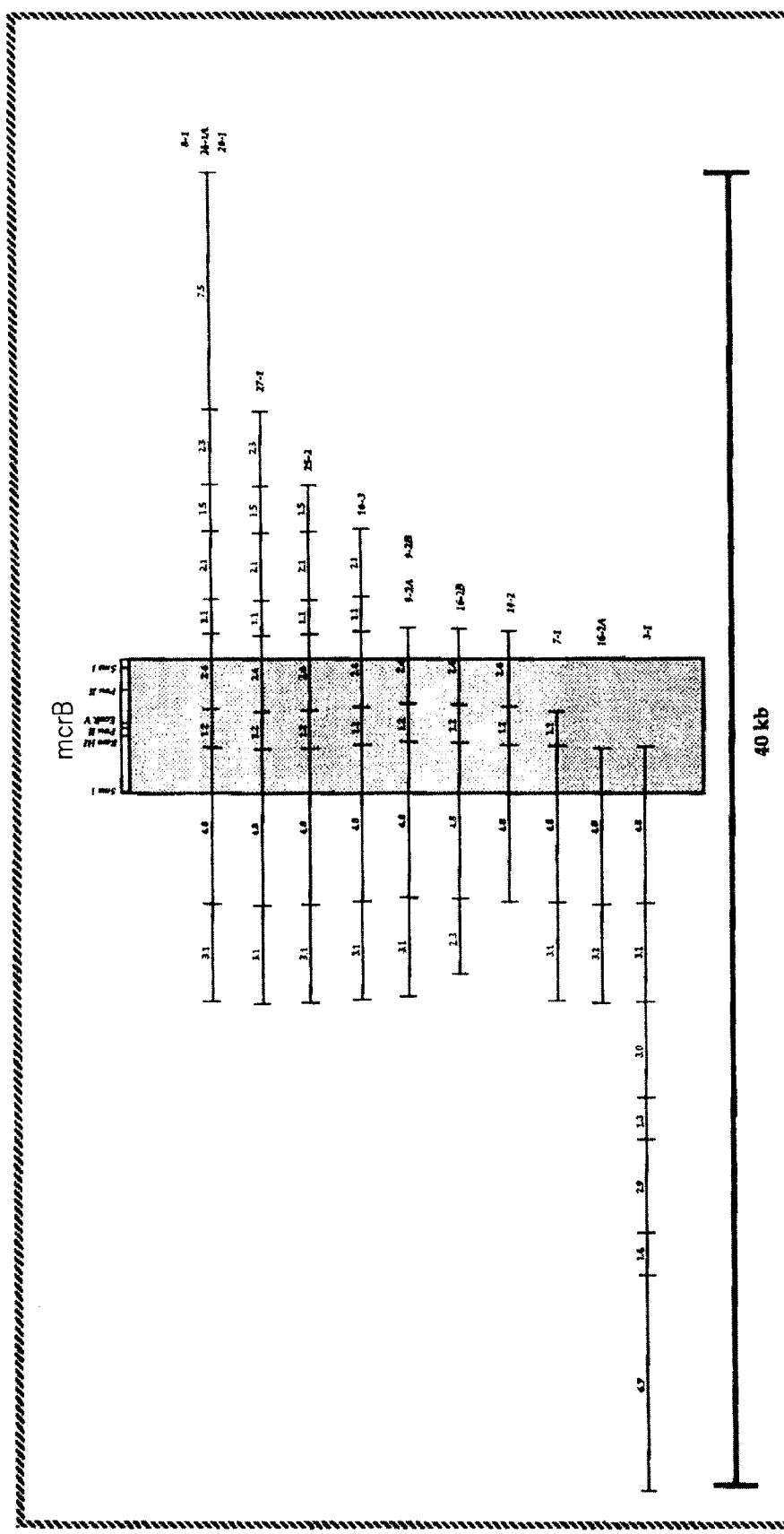
FIG. 8. Restriction enzyme maps of the cosmid clones containing *S. lavendulae* DNA adjacent to the mrd locus. The central shaded region denotes the boundaries of the mrd locus.

Cloning and Analysis of Cosmids Containing DNA Adjacent to mcrA and mcrB; Generation of Mutants of mcrA Blocked in MMC Resistance In order to establish whether DNA adjacent to one or both MMC resistance genes includes a cluster of biosynthetic genes for the metabolite, we have generated a *S. lavendulae* genomic library using the Streptomyces-*E. coli* shuttle vector, pNJ1 (Tuan et. al., 1990). High molecular weight genomic DNA was subjected to partial digestion to generate fragments about 30–40 kb in length. The library was subsequently screened with $^{32}$p-labeled mcr or mrd. A single cosmid clone (encompassing ~25 kb) was identified using mcr as a probe, and its map is shown in FIG. 7. For mrd, a series of overlapping cosmid clones (encompassing ~40 kb) were identified and mapped, as shown in FIG. 8. It will now be possible to choose specific regions of the cosmid clones surrounding the resistance gene mcr or mrd to begin probing for genes involved in biosynthesis of MMC.

Figure 9:
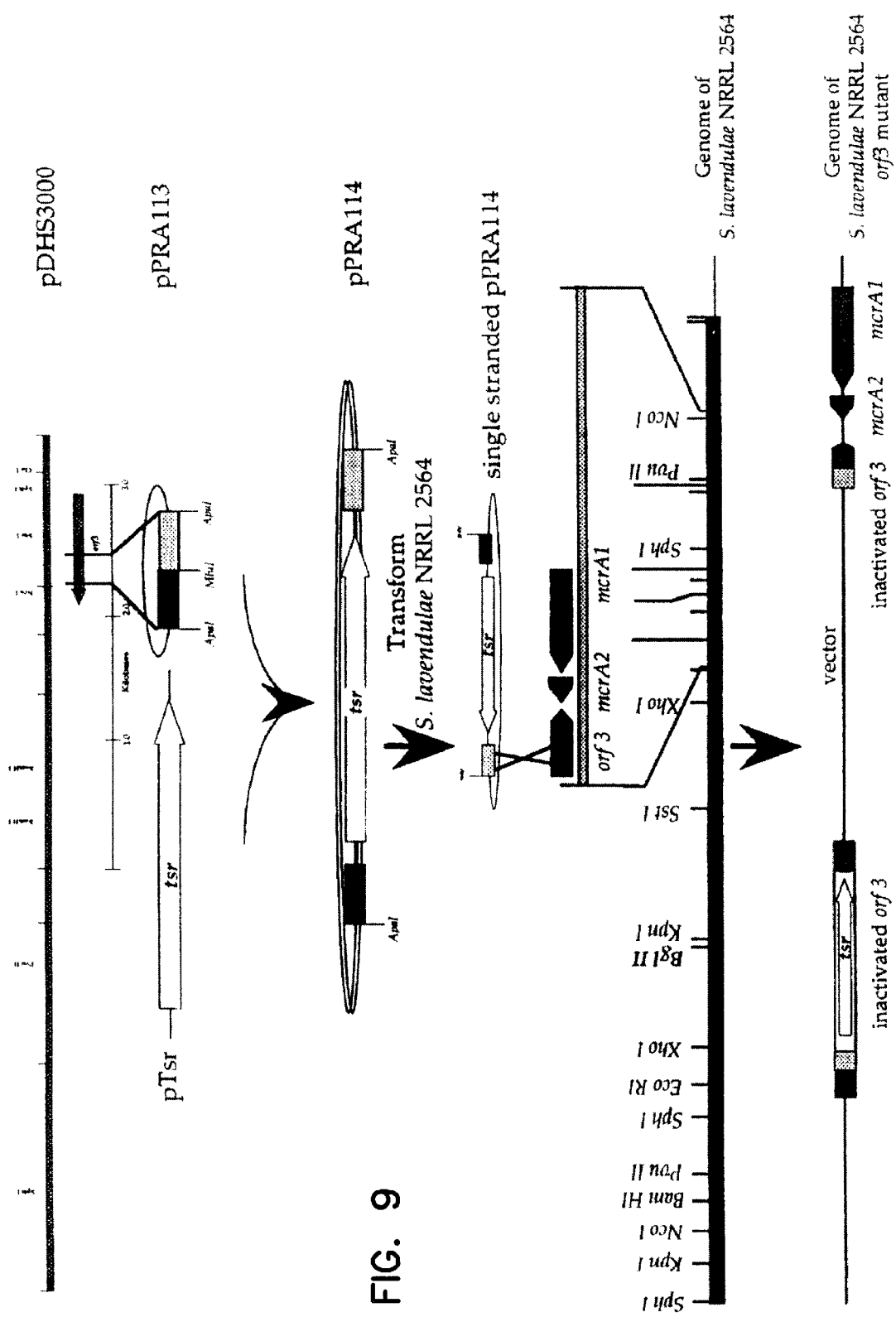
FIG. 9. Strategy for gene-disruption by homologous recombination. The thiostrepton resistance gene (tsr) was used for selection by cloning into the middle of mcrORF3. Single-stranded DNA was then used to transform *S. lavendulae*, followed by selection with thiostrepton to obtain recombinant organisms.

Analysis of *S. lavendulae* DNA involved in MMC biosynthesis involves the method of gene disruption. In order to determine whether mcrORF3 is involved in a biosynthetic step for MMC biosynthesis, we decided to generate a clone to test functional activity by gene disruption. Therefore, mcrORF3 was used to generate a clone in pUC119 useful for gene disruption in *S. lavendulae*. The thiostrepton resistance gene (tsr) was inserted into the middle of a fragment internal to the predicted mcrORF3 reading frame. Single-stranded DNA generated from this construct was used to transform *S. lavendulae* protoplasts. Selection for thiostrepton resistance allowed convenient identification of several clones that are currently under analysis (FIG. 9). Initially these clones will be screened for the presence of tsr in the chromosome and integration of the construct used for gene disruption. Fermentation and analysis of MMC production will then be performed on clones of *S. lavendulae* in which the mcrORF3 gene is inactivated.

A similar strategy will be followed for DNA adjacent to mcr and mrd contained on cosmid clones. Clones with these inserts in pUC119 are identified and used to transform *S. lavendulae*. Transformants will be screened for loss of production of MMC by identifying clones that no longer exhibit biological activity and then performing HPLC analysis to show loss of production of MMC.

Another strategy for obtaining *S. lavendulae* mutants blocked in MMC production includes transposon mutagenesis method for Streptomyces spp. This approach involves use of a hypertransposing element Tn5099-10 and a-temperature sensitive delivery system from pGM160. Briefly, the vector containing Tn5099-10 will be transformed into the MMC-producing *S. lavendulae* wild-type strain. Incubation at elevated temperatures induces transposition randomly into the chromosome. Transposon mutants blocked in MMC production will be identified using a biological assay as described previously. Loss of MMC production will be confirmed by analysis of extracts by HPLC.

These methods should provide MMC blocked mutants.

EXAMPLE 7

Method for Identifying Agents that Can Inhibit Resistance of a Cell to a DNA Alkylating or Cleaving Agent A method for identifying agents that inhibit resistance of a cell to a DNA alkylating or cleaving agent can be conducted as described below.

Transformed cultures of *S. lividans* carrying plasmid pDHS3005 can be cultured in the presence of 0, 1, 10, 25, 100, 500, or 1000 $\mu$g/ml of mitomycin C and in the presence or absence of a suspected inhibitory agent. The transformed cells can be incubated for about 7 days. After incubation, growth of the transformed cells is determined by dry cell weight or plate count method. Cells that are resistant to mitomycin C will grow in the presence of at least about 10 $\mu$g/ml of mitomycin C. Inhibition of resistance of cells to mitomycin is seen when cells cannot grow in the presence of about 10 to 100 $\mu$g/ml of mitomycin C. A sensitive cell will preferably not show any growth at 25 $\mu$g/ml of mitomycin C. It is likely that an inhibitory agent will prevent or inhibit growth of the transformed *S. lividans* in the presence of concentrations of mitomycin of 10 $\mu$g/ml or greater, preferably growth is inhibited at least about 10-fold.

EXAMPLE 8

Determination of Mechanism of Action of MCRA

An assay for catalytic activity and to ascertain the mechanism of resistance toward MMC was developed. A UV spectrophotometric assay has been developed using the absorbance of MMC at 363 nm to determine whether reduction of MMC is prevented by MCRA. In this assay, freshly prepared extracts of *S. lividans*/pDHS3000 containing overexpressed MCRA were used in a reaction mixture containing MMC and the chemical reducing agent sodium dithionite. Oxidation state of MMC is assessed at 363 nm. The results show clearly that MMC is reduced to the hydroquinone in the absence of MCRA by a 100% loss of 363 nm (change) in absorbance of MMC. However, when an extract containing overexpressed MCRA is added to the reaction mixture, no change in absorbance (363 nm) of MMC is observed. These experiments indicate that MCRA acts in vivo by protecting *S. lavendulae* from the adverse affects of MMC through maintaining the non-activated oxidative state of the molecule.

EXAMPLE 9

Determining Expression of MCRA in a *S. lavendulae*, a Naturally Resistant Host Cell The expression of MCRA in *S. lavendulae* was detected using an ELISA assay on cell lysates taken at various time points during growth of the cells in culture.

Large scale fermentation of *S. lavendulae*. *S. lavendulae* was inoculated into production media IM-1 as previously described with the exception that the glycerol concentration was doubled. Bioreactor pH was controlled by the addition of 6M NaOH and 50% phosphoric acid. Foaming was controlled by the addition of 10% antifoam when necessary. Bioreactor pressure was maintained at 4 atm. and sparged at 45 psi at 4 L/min. The impeller speed was initially 350 rpm at inoculation and increased to 500 rpm after 24 hours. 50 milliliter samples were taken from the reactor for dry weight, MC production, and MCRA expression measurements every 12 hours. 30 milliliters of the sample was processed to isolate the fermentation broth and mycelia. Two, 10 milliliter aliquots of the original sample were processed for dry weight determinations.

Samples were centrifuged at 5K for 10 minutes. For dry weight determinations the pellets were washed 4 times with 5 volumes of distilled water to remove salts and calcium carbonate. Mycelia for protein isolation was washed 4 times with phosphate buffered saline (PBS). Samples for dry weights were resuspended in 1 volume of distilled water and poured into pre-weighed aluminum cupcake tins which were dried at 80° C. for 24 hrs after which they were re-weighed and the dry mass determined. Fermentation broth was sterile filtered at room temperature and the presence of MMC was assayed by HPLC immediately. Samples for protein isolation were resuspended in one volume of PBS. The mycelia were incubated on ice for 15 minutes and then sonicated as described. The cell extract was centrifuged at 4° C. at 10K for 30 minutes. The supernatant was removed and sterile filtered through a 0.2 uM filter. These extracts were frozen at −80° C. The cell extracts were analyzed for the presence of MCRA.

Figure 17:
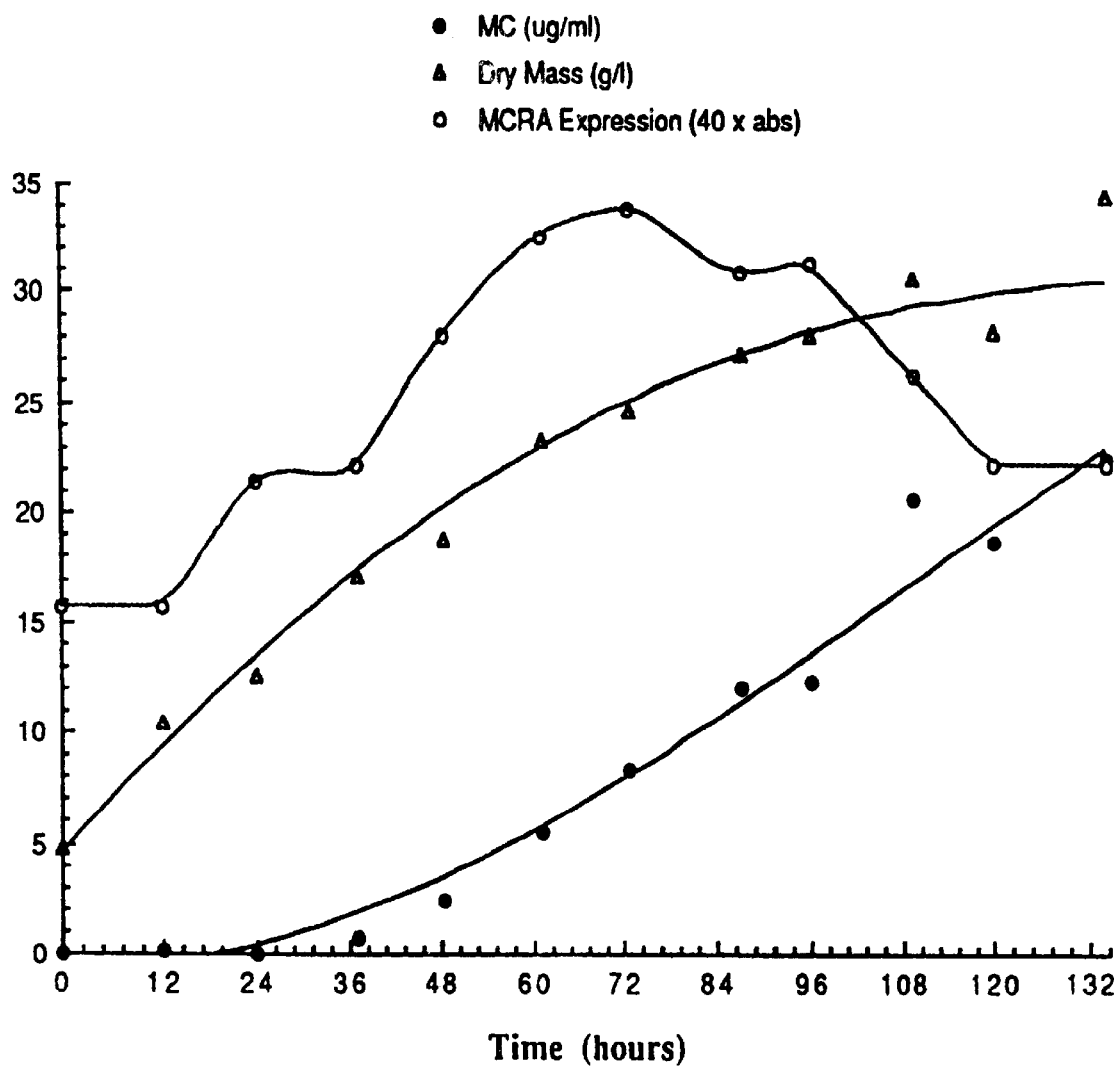
FIG. 17. 15 L fermentation of *S. lavendulae* showing MMC production, dry mass and MCRA expression over the course of a 240 hr culture.

*S. lavendulae* has the ability to produce MMC at high concentrations when it is grown in the proper fermentation medium. Given this ability it is expected that it would be resistant to MMC at high levels. Additionally, if MCRA confers MMC resistance then it should be detected in cells producing MMC. As shown in FIG. 17, *S. lavendulae* was grown to stationary phase and produced MMC as determined by HPLC analysis. In addition, ELISA assays revealed that MCRA was expressed. MCRA was expressed at a low level prior to MMC production, and was strongly expressed just prior to MMC biosynthesis. Most likely the induction is due to the presence of MMC produced which is below the limit of our ability to detect MMC. Thus, MCRA is produced in the naturally resistant host cell that produces MMC and is inducibly expressed by MMC as has been observed in *S. Lividans* pDHS3000.

EXAMPLE 10

Assay to Identify Polypeptides Related to MCRA Present in MMC Resistant Tumor Cells Polyclonal and monoclonal antibodies can be used to identify and/or isolate polypeptides related to MCRA present in MMC resistant tumor cells.

MMC resistant tumor cell lines have been described by Pan et al. Dr. SuShu PAN, University of Maryland Cancer Center, The New Frank Bressler Research Laboratories, Baltimore, Md. 21201 and are available from her laboratory. Tumor cells can be exposed to varying concentrations of MMC and then cell extracts containing cytoplasmic proteins can be obtained. The cell extracts can be screened for polypeptides reactive with polyclonal and/or monoclonal antibodies specific for MCRA in an ELISA as described previously for *S. lavendulae* cell extracts in Example 3. Cell lines exhibiting positive reactivity with antibodies to MCRA can be further analyzed using affinity chromatography and/or Western blots using standard methods. It is expected that the antibodies to MCRA would identify mammalian polypeptides related to MCRA. These antibodies can be used to isolate these polypeptides with affinity chromatography.

These antibodies could be useful in isolation and identification of DNA or cDNA sequence coding for a polypeptide related to MCRA using methods known to those of skill in the art, such as dot blot, mammalian cDNA library generation, and sequence analysis.

All publications and patent applications in this specification are indicative of the level of ordinary skill in the art to which this invention pertains. All publications and patent applications are herein incorporated by reference to the same extent as if each individual publication or patent application was specifically and individually indicated by reference.

While the present invention has been described in connection with the preferred embodiment thereof, it will be understood many modifications will be readily apparent to those skilled in the art, and this application is intended to cover any adaptations or variations thereof. It is manifestly intended this invention be limited only by the claims and equivalents thereof.

What is claimed is:

1. An isolated expression cassette comprising: a promoter operably linked to a DNA sequence of *S. lavendulae* which encodes resistance to mitomycin, wherein the DNA sequence is selected from the group consisting of SEQ ID NO:1 and SEQ ID NO:11.

2. An isolated expression cassette comprising: a promoter operably linked to a DNA sequence of *S. lavendulae* which, when expressed in a cell, confers mitomycin resistance to the cell at greater than 100 mg/ml mitomycin, wherein the DNA sequence is SEQ ID NO:1.

3. An isolated expression cassette comprising: a DNA sequence that encodes a polypeptide comprising SEQ ID NO:5.

4. An isolated expression cassette comprising: a promoter operably linked to SEQ ID NO:1, SEQ ID NO:2 or SEQ ID NO:11.

5. An isolated expression cassette comprising: a promoter operably linked to a DNA sequence of *S. lavendulae* which encodes resistance to mitomycin, wherein the DNA sequence encodes a protein encoded by SEQ ID NO:11.

6. The expression cassette of claim 1 or 2 wherein SEQ ID NO: 1 encodes a polypeptide having a molecular mass of about 56,000 daltons on Sodium dodecyl sulfate-Polyacrylamide gel electrophoresis (SDS-PAGE).

7. The expression cassette of claim 1, 2, or 3 wherein the promoter is heterologous to *S. lavendulae*.

8. A plasmid comprising the expression cassette of claim 1.

9. A plasmid comprising the expression cassette of claim 2 or 3.

10. A plasmid comprising the expression cassette of claim 4.

11. A plasmid comprising the expression cassette of claim 5.

12. A probe comprising an isolated nucleic acid sequence comprising at least 50 contiguous nucleotides of SEQ ID NO: 1 or SEQ ID NO: 11, wherein the probe detects DNA complementary to DNA encoding mitomycin resistance.

13. A probe comprising an isolated nucleic acid sequence comprising at least 50 contiguous nucleotides of the complement of SEQ ID NO: 1 or SEQ ID NO: 11, wherein the probe detects DNA encoding mitomycin resistance.

14. The probe of claim 12 or 13 wherein the probe is detectably labeled.

15. The probe of claim 12 wherein the contiguous nucleotides include nucleotides 310 to 330, nucleotides 1415 to 1438, or nucleotides 641 to 661 of SEQ ID NO: 1.

16. The probe of claim 13 wherein the contiguous nucleotides include the complement of nucleotides 310 to 330, nucleotides 1415 to 1438, or nucleotides 641 to 661 of SEQ ID NO: 1.

17. The probe of claim 12 wherein the nucleic acid sequence is SEQ ID NO:1.

18. The probe of claim 13 wherein the nucleic acid sequence is the complement of SEQ ID NO:1.

19. An isolated transformed cell comprising: a heterologous nucleic acid Sequence comprising a promoter functional in the cell operably linked to a DNA sequence of *S. lavendulae* which encodes resistance to mitomycin, wherein the DNA sequence is selected from the group consisting of SEQ ID NO: 1 and SEQ ID NO: 11.

20. An isolated transformed cell comprising: a heterologous nucleic acid sequence comprising a promoter functional in the cell operably linked to a DNA sequence of *S. lavendulae* which encodes resistance to mitomycin, wherein the DNA sequence is SEQ ID NO: 11.

21. An isolated transformed cell comprising: a heterologous nucleic acid Sequence comprising a promoter functional in the cell operably linked to a DNA sequence of *S. lavendulae* which encodes resistance to mitomycin, wherein the DNA sequence encodes SEQ ID NO: 5.

22. An isolated transformed cell comprising: a heterologous nucleic acid sequence comprising a promoter functional in the cell operably linked to a DNA sequence of *S. lavendulae* which encodes resistance to mitomycin, wherein the DNA sequence encodes a protein encoded by SEQ ID NO:11.

23. An isolated transformed cell comprising: a heterologous nucleic acid Sequence comprising a promoter functional in the cell operably linked to a DNA sequence of *S. lavendulae*, which confers mitomycin resistance to the cell, at greater than 100 mg/ml mitomycin, wherein the DNA sequence is SEQ ID NO: 1.

24. The isolated transformed cell of claim 19, 20, 21, 22 or 23 which is a tumor cell.

* * * * *

UNITED STATES PATENT AND TRADEMARK OFFICE
CERTIFICATE OF CORRECTION

PATENT NO. : 6,524,812 B1
DATED : February 25, 2003
INVENTOR(S) : Michael C. Flickinger et al.

It is certified that error appears in the above-identified patent and that said Letters Patent is hereby corrected as shown below:

Title page,
Item [56], References Cited, OTHER PUBLICATIONS, reference "August et al (1992) Abstract B19...." delete "In," and insert -- In., --.

Column 1,
Line 4, delete "provision" and insert -- prosecution -- therefor.

Column 55,
Line 36, delete "3" and insert -- 5 -- therefor.

Signed and Sealed this

Ninth Day of September, 2003

JAMES E. ROGAN
*Director of the United States Patent and Trademark Office*